(12) United States Patent
Rybicki et al.

(10) Patent No.: US 9,994,859 B2
(45) Date of Patent: Jun. 12, 2018

(54) PLANT PRODUCED HUMAN PAPILLOMAVIRUS PSEUDOVIRION

(71) Applicant: University of Cape Town, Cape Town (ZA)

(72) Inventors: Edward P Rybicki, Cape Town (ZA); Inga Isabel Hitzeroth, Cape Town (ZA)

(73) Assignee: University of Cape Town, Cape town (ZA)

(*) Notice: Subject to any disclaimer, the term of this patent is extended or adjusted under 35 U.S.C. 154(b) by 0 days. days.

(21) Appl. No.: 14/907,323

(22) PCT Filed: Jul. 25, 2014

(86) PCT No.: PCT/IB2014/063411
§ 371 (c)(1),
(2) Date: Jan. 25, 2016

(87) PCT Pub. No.: WO2015/011676
PCT Pub. Date: Jan. 29, 2015

(65) Prior Publication Data
US 2016/0168583 A1 Jun. 16, 2016

(30) Foreign Application Priority Data
Jul. 25, 2013 (ZA) .................. 2013/05650

(51) Int. Cl.
| | |
|---|---|
| C12N 7/00 | (2006.01) |
| C12N 15/82 | (2006.01) |
| A61K 48/00 | (2006.01) |
| A61K 39/12 | (2006.01) |
| A61K 35/76 | (2015.01) |
| A61K 39/00 | (2006.01) |

(52) U.S. Cl.
CPC .......... *C12N 15/8203* (2013.01); *A61K 35/76* (2013.01); *A61K 39/12* (2013.01); *A61K 48/00* (2013.01); *C12N 7/00* (2013.01); *C12N 15/8205* (2013.01); *C12N 15/8257* (2013.01); *C12N 15/8258* (2013.01); *A61K 2039/5258* (2013.01); *A61K 2039/575* (2013.01); *C12N 2710/20023* (2013.01); *C12N 2710/20034* (2013.01); *C12N 2710/20051* (2013.01); *C12N 2750/12043* (2013.01)

(58) Field of Classification Search
None
See application file for complete search history.

(56) References Cited

PUBLICATIONS

Hernandez et al. Human Papillomavirus (HPV) L1 and L1-L2 Virus-Like Particle-Based Multiplex Assays for Measurement of HPV Virion Antibodies. Clinical and Vaccine Immunology. 2012. 19: 1348-1352.*
Buck. et al. Efficient Intracellular Assembly of Papillomaviral Vectors. Journal of Virology. 2004, 78: 751-757.*
Giorgi et al. Human papillomavirus vaccines in plants. Expert Rev. Vaccines, 2010, 9(8):913-924.*
Huang et al. A DNA Replicon System for Rapid High-Level Production of Virus-Like Particles in Plants. Biotechnology and Bioengineering, 2009, 103:706-714.*
Huang et al. A DNA Replicon System for Rapid High-Level Production of Virus-Like Particles in Plants. Biotechnol. Bioeng. 2009;103: 706-714.*
Zhou, Jian et al.: "Expression of Vaccinia Recombinant HPV 16 L1 and L2 ORF Proteins in Epithelial Cells Is Sufficient for Assembly of HPV Virion-like Particles", *Virology*, 185, pp. 251-257 (1991).
Giorgi, Colomba et al.: "Human papillomavirus vaccines in plants", *Expert Review of Vaccines*, 9 (8) (2010) pp. 913-924.
Xu, Y.-F et al.: "Papillomavirus virus-like particles as vehicles for the delivery of epitopes or genes", *Archives of Virology*, (2006) 151, pp. 2133-2148.
Malboeuf, Christine M. et al.: "Human papillomavirus-like particles mediate functional delivery of plasmid DNA to antigen presenting cellsin vivo", *Vaccine*, 25 (2007), pp. 3270-3276.
Windram, Oliver P. et al.: "An investigation into the use of human papillomavirus type 16 virus-like particles as a delivery vector system for foreign proteins: N- and C-terminal fusion of GFP to the L1 and L2 capsid proteins", *Arch Virol*, (2008) 153: pp. 585-589.
Chen, Qiang et al.: "Plant-derived virus-like particles as vaccines", *Human Vaccines & Immunotherapeutics*, vol. 9 Issue 1, Jan. 2013, pp. 26-49.
Regnard, Guy L. et al.: "High level protein expression in plants through the use of a novel autonomously replicating geminivirus shuttle vector", *Plant Biotechnology Journal*, 8, pp. 38-46.
Pastrana, Diana V. et al.: "Reactivity of human sera in a sensitive, high-throughput pseudovirus-based papillomavirus neutralization assay for HPV16 and HPV18", *Virology*, 321 (2004), pp. 205-216.
Fernandez-San Millan, Alicia et al.: "Human papillomavirus L1 protein expressed in tobacco chloroplasts self-assemblies into virus-like particles that are highly immunogenic", *Plant Biotechnology Journal*, (2008), 6, pp. 427-441.
Smidkova, M. et al.: "Transient expression of human papillomavirus type 16 virus-like particles in tobacco and tomato using a tobacco rattle virus expression vector", *Biologia Plantarum*, vol. 54, No. 3, Jun. 23, 2010, pp. 451-460.
Rybicki, Edward P. et al.: "Vaccine farming in Cape Town", *Human Vaccines*, vol. 7, Issue 3, Mar. 2011 pp. 339-348.
Kennedy, Paul: "HPV Pseudovirion Production in Plants", Feb. 2013, published by the University of Cape Town, pp. 1-111.
International Search Reportissued by European Patent Office acting as the International Searching Authority, for PCT/IB2014/063411 dated Jan. 13, 2015.
Bakker et al., 2006. Proc Natl Acad Sci USA 103, 7577-7582.
Biemelt et al., 2003. Journal of virology 77, 9211-9220.
Bird et al., 2008. Journal of virology 82, 9848-9857.
Bousarghin et al., 2002. Journal of clinical microbiology 40, 926-932.
Brondyk., 2009. Methods in enzymology 463, 131-147.
Buck et al., 2008. Journal of virology 82, 5190-5197.

(Continued)

*Primary Examiner* — Nianxiang (Nick) Zou
(74) *Attorney, Agent, or Firm* — Haug Partners LLP

(57) ABSTRACT

The present invention relates to a method of producing HPV pseudovirions in plant cells, the plant produced pseudovirions per se, a neutralization assay using the plant produced pseudovirions and pharmaceutical compositions comprising the plant produced pseudovirions.

17 Claims, 33 Drawing Sheets

(56) References Cited

PUBLICATIONS

Buck et al., 2005a. Methods in molecular medicine 119, 445-462.
Buck et al., 2005b. Journal of virology 79, 2839-2846.
Christensen et al., 1996. Virology 223, 174-184.
Christensen et al., 1990. Journal of virology 64, 5678-5681.
Christensen et al., 1992. The Journal of general virology 73 (Pt 5), 1261-1267.
Chromy et al., 2006. Journal of virology 80, 5086-5091.
Daniell et al., 2009. Trends in plant science 14, 669-679.
Dessy et al., 2008. Human vaccines 4, 425434.
Durrani et al., 1998. Journal of immunological methods 220, 93-103.
Dvoretzky et al., 1980. Virology 103, 369-375.
Fay et al., 2004. Journal of virology 78, 13447-13454.
Ferlay et al., 2010. International journal of cancer. 127, 2893-2917,.
Fleury et al., 2008. Clinical and vaccine immunology: CVI 15, 172-175.
Garcea and Gissmann., 2004. Current opinion in biotechnology 15, 513-517.
Gleba et al., 2007. Current opinion in biotechnology 18, 134-141.
Harper et al., 2006. Lancet 367, 1247-1255.
Holmgren et al., 2005. Journal of virology 79, 3938-3948.
Kapila et al., 1997. Plant Science 122, 101-108.
Kawana et al., 1998. Journal of virology 72, 10298-10300.
Kellogg., 1927. International Critical Tables. Science 65, 273.
Kohl et al., 2006. Clinical and vaccine immunology: CVI 13, 845-853.
Kreider et al., 1987. Journal of virology 61, 590-593.
Kunik et al., 1999. Journal of experimental botany 50, 731-732.
Li et al., 1997. Journal of virology 71, 2988-2995.
Ma et al., 2011. Therapeutic delivery 2, 427-430.
Ma et al., 2005. Trends in plant science 10, 580-585.
Mach et al., 2006. Journal of pharmaceutical sciences 95, 2195-2206.
Maclean et al., 2007. The Journal of general virology 88, 1460-1469.
Matic et al., 2012. Plant biotechnology journal.
Muller et al., 1995. Journal of virology 69, 948-954.
Nuttall et al, 2002. European journal of biochemistry/FEBS 269, 6042-6051.
Ochsenbauer and Kappes., 2009. Current opinion in HIV and AIDS 4, 418-425.
Ogle., 2008. University of Cape Town, Cape Town.
Oh et al., 2004. Virology 328, 266-273.
Okun et al., 2001. Journal of virology 75, 4332-4342.
Peng et al., 2011. Cell & bioscience 1, 26.
Pereira., 2008. University of Cape Town, Cape Town.
Pereira et al., 2009. Arch Virol 154, 187-197.
Robbins et al., 1995. The Journal of infectious diseases 171, 1387-1398.
Roden et al., 1996. Journal of virology 70, 5875-5883.
Rossi et al., 2000. Human gene therapy 11, 1165-1176.
Rybicki., 2010. Plant biotechnology journal 8, 620-637.
Santi et al., 2006. Methods 40, 66-76.
Schillberg et al., 2005. Vaccine 23, 1764-1769.
Shen and Forde 1989. Nucleic acids research 17, 8385.
Shi et al., 2001. Journal of virology 75, 10139-10148.
Smith et al., 1995. The Journal of investigative dermatology 105, 438-444.
Stanley et al., 2008. Vaccine 26 Suppl 10, K62-67.
Stauffer et al., 1998. Journal of molecular biology 283, 529-536.
Sullivan and Pipas, 2001. Virology 287, 1-8.
Tiwari et al., 2009. Biotechnology advances 27, 449-467.
Touze and Coursaget., 1998. Nucleic acids research 26, 1317-1323.
Turpen et al., 1995. Biotechnology (N Y) 13, 53-57.
Unckell et al., 1997. Journal of virology 71, 2934-2939.
Varsani et al., 2003. Journal of virology 77, 8386-8393.
Varsani et al., 2006. Virus research 120, 91-96.
Warzecha et al, 2003. Journal of virology 77, 8702-8711.
Waymouth, 1970. In vitro 6, 109-127.
Yeager et al., 2000. Virology 278, 570-577.
Zhang and Mason. 2006. Biotechnol. Bioeng. 93, 271-279.
Zhou et al., 1993. Virology 194, 210-218.
Zupan et al., 2000. The plant journal: for cell and molecular biology 23, 11-28.

* cited by examiner

FIGURE 11 CONT
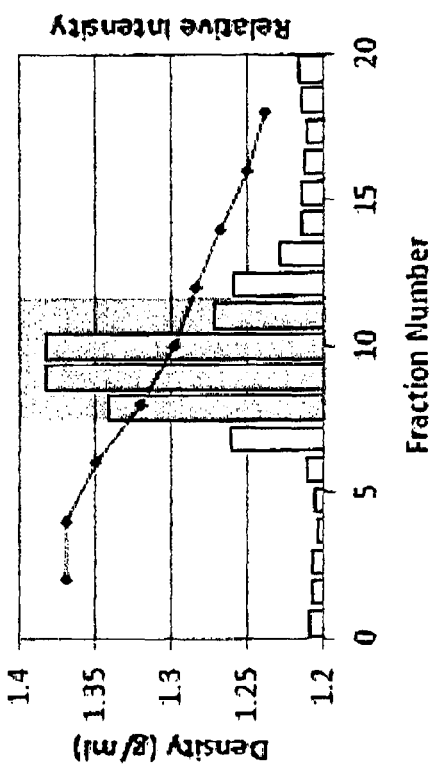
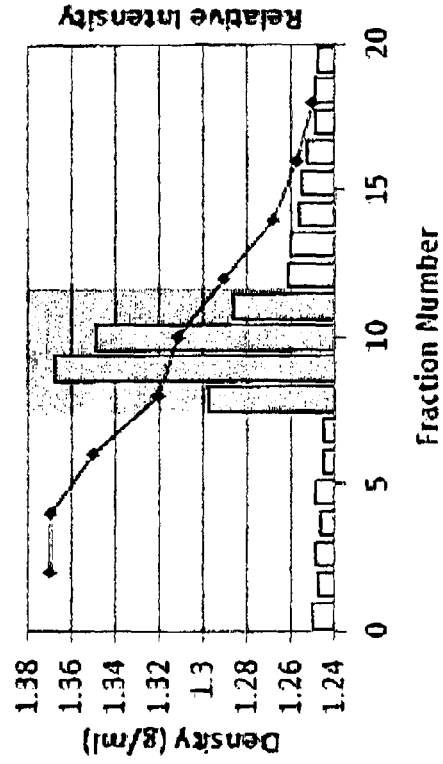

```
gtcgacggat ccttatcgat tttaccacat ttgtagaggt tttacttgct ttaaaaaacc    60
tcccacacct cccccttgaac ctgaaacata aaatgaatgc aattgttgtt gttaacttgt   120
ttattgcagc ttataatggt tacaaataaa gcaatagcat cacaaatttc acaaataaag   180
catttttttc actgcattct agttgtggtt tgtccaaact catcaatgta tcttatcatg   240
tctgctcgaa gcggccggcc gccccgactc tagagtaacc cgggtgcgcg gcgtcggtgg   300
tgccggcggg gggcgccagg tcgcaggcgg tgtagggctc caggcaggcg gcgaaggcca   360
tgacgtgcgc tatgaaggtc tgctcctgca cgccgtgaac caggtgcgcc tgcgggccgc   420
gcgcgaacac cgccacgtcc tcgcctgcgt gggtctcttc gtccaggggc actgctgact   480
gctgccgata ctcggggctc ccgctctcgc tctcggtaac atccggccgg gcgccgtcct   540
tgagcacata gcctggaccg tttccgtata ggaggaccgt gtaggccttc ctgtcccggg   600
ccttgccagg ggccagcccg aagatggagc tccctcgcag ggggtagcct ccgaaggaga   660
agacgtggga gtggtcggca gtgacgaggc tcagcgtgtc ctcctcgctg gtgagctggc   720
ccgccctctc aatggcgtcg tcgaacatga tcgtctcagt cagtgccgg taagccctgc    780
tttcatgatg accatggtcg atgcgaccac cctccacgaa gaggaagaag ccgcggggt    840
tcctgctcag caggcgcagg gcagcctctg tcatctccat cagggagggg tccagtgtgg   900
agtctcggtg gatctcgtat ttcatgtctc caggctcaaa gagacccatg agatgggtca   960
cagacgggtc cagggaagcc tgcatgagct cagtgcggtt ccacacatac cgggcaccct  1020
ggcgcttcgc cagccattcc tgcaccagat tcttcccgtc cagcctggtc ccaccttggc  1080
tgtagtcatc tgggtactca gggtctgggg ttcccatgcg aaacatgtac tttcggcctc  1140
cacctaggat cacgtcaatg tccatgttgg agatgagctg cgtagcgatg tcctggcacc  1200
cctcctggcg ggccgaggca ggcacgtcgg cgtccgagta ccagttgcgg ttcaccgtgt  1260
gggcgtaggt gccggctggc gaggcgtgct gcactcgtgt ggtggttacc actccactg   1320
acttccctgc tttcttggcc cgattcatca cggagatgac ctcgttgccg cgtgtcgtgt  1380
tgcactggtt aaagcgggcg gctgcactca agccaatggt ctggaagttg cccttgaccc  1440
cgcacaggta ggccgtggct gtggctccac tgtctggcac atgtttgtct acattgtatg  1500
tcttggacag agccacatat gggaagcggt ccatggccag gggtatctca ggccccagtt  1560
tgtccttctt ctgcccttttt aggatcctgg cagctgtcac cgtagacacc cccatcccat  1620
cgcccaggaa gatgatgagg ttcttggcgg ctgtctgtgc aggctgcagc ttcttggcgg  1680
cacccagggc ctcggctgcc tcgcggttcc agaagtccgg gttctcctcc tcaactggga  1740
tgatgccag ggagagctgt agcctcaggc ccagcagcag cagcagcagc agcatggtgg   1800
gcgaattcgc gattcgaagc ttacttagat cgcagatcca gcacaatgga tctcgaggtc  1860
gagggatctc tacagaattc tcacgacacc tgaaatggaa gaaaaaaact ttgaaccact  1920
gtctgaggct tgagaatgaa ccaagatcca aactcaaaaa gggcaaattc caaggagaat  1980
tacatcaagt gccaagctgg cctaacttca gtctccaccc actcagtgtg gggaaactcc  2040
atcgcataaa acccctcccc ccaacctaaa gacgacgtac tccaaaagct cgagaactaa  2100
tcgaggtgcc tggacggcgc ccggtactcc gtggagtcac atgaagcgac ggctgaggac  2160
ggaaaggccc ttttccctttg tgtgggtgac tcaccgcccc gctctcccga gcgccgcgtc  2220
ctccatttttg agctccctgc agcagggccg ggaaggccga atctttccgc tcacgcaact  2280
ggtgccgacc gggccagcct tgccgcccag ggcggggcga tacacggcgg cgcgaggcca  2340
ggcaccagag caggccggcc agcttgagac tacccccgtc cgattctcgg tggccgcgct  2400
cgcaggcccc gcctcgccga acatgtgcgc tgggacgcac gggccccgtc gccgcccgcg  2460
gccccaaaaa ccgaaatacc agtgtgcaga tcttggcccg catttacaag actatcttgc  2520
cagaaaaaaa gcgtcgcagc aggtcatcaa aaattttaaa tggctagaga cttatcgaaa  2580
gcagcgagac aggcgcgaag gtgccaccag attcgcacgc ggcggcccca gcgcccaggc  2640
caggcctcaa ctcaagcacg aggcgaaggg gctccttaag cgcaaggcct cgaactctcc  2700
cacccacttc caacccgaag ctcgggatca agaatcacgt actgcagcca ggtggaagta  2760
attcaaggca cgcaagggcc ataacccgta aagaggccag gccgcggga accacacacg   2820
gcacttacct gtgttctggc ggcaaacccg ttgcgaaaaa gaacgttcac ggcgactact  2880
gcacttatat acggttctcc cccaccctcg ggaaaaaggc ggagccagta cacgacatca  2940
ctttcccagt ttaccccgcg ccaccttctc taggcaccgg ttcaattgcc gacccctcc   3000
ccaacttct cggggactgt gggcgatgtg cgctctgccc actgacgggc accggagcca  3060
attcccagtc gac                                                    3073
```

FIGURE 16

```
gtcgacggat ccttatcgat tttaccacat ttgtagaggt tttacttgct ttaaaaaacc    60
tcccacacct cccctgaac ctgaaacata aaatgaatgc aattgttgtt gttaacttgt    120
ttattgcagc ttataatggt tacaaataaa gcaatagcat cacaaatttc acaaataaag   180
catttttttc actgcattct agttgtggtt tgtccaaact catcaatgta tcttatcatg   240
tctgctcgaa gcggccggcc gccccgactc tagagtaacc cgggtgcgcg gcgtcggtgg   300
tgccggcggg ggcgccagg tcgcaggcgg tgtagggctc caggcaggcg gcgaaggcca   360
tgacgtgcgc tatgaaggtc tgctcctgca cgccgtgaac caggtgcgcc tgcgggccgc   420
gcgcgaacac cgccacgtcc tcgcctgcgt gggtctcttc gtccagggc actgctgact    480
gctgccgata ctcggggctc ccgctctcgc tctcggtaac atccggccgg gcgccgtcct   540
tgagcacata gcctggaccg tttccgtata ggaggaccgt gtaggccttc ctgtcccgcg   600
ccttgccagg ggccagcccg aagatggagc tccctcgcag ggggtagcct ccgaaggaga   660
agacgtggga gtggtcggca gtgacgaggc tcagcgtgtc ctcctcgctg gtgagctggc   720
ccgccctctc aatggcgtcg tcgaacatga tcgtctcagt cagtgcccgg taagccctgc   780
tttcatgatg accatggtcg atgcgaccac cctccacgaa gaggaagaag ccgcggggt    840
tcctgctcag caggcgcagg gcagcctctg tcatctccat cagggagggg tccagtgtgg   900
agtctcggtg gatctcgtat ttcatgtctc caggctcaaa gagacccatg agatgggtca   960
cagacgggtc cagggaagcc tgcatgagct cagtgcggtt ccacacatac cgggcaccct  1020
ggcgcttcgc cagccattcc tgcaccagat tcttcccgtc cagcctggtc ccaccttggc  1080
tgtagtcatc tgggtactca gggtctgggg ttccatgcg aaacatgtac tttcggcctc   1140
cacctaggat cacgtcaatg tccatgttgg agatgagctg cgtagcgatg tcctggcacc  1200
cctcctggcg ggccgaggca ggcacgtcgg cgtccgagta ccagttgcgg ttcaccgtgt  1260
gggcgtaggt gccggctggc gaggcgtgct gcactcgtgt ggtggttacc actcccactg  1320
acttccctgc tttcttggcc cgattcatca cggagatgac ctcgttgccg cgtgtcgtgt  1380
tgcactggtt aaagcgggcg gctgcactca agccaatggt ctggaagttg cccttgaccc  1440
cgcacaggta ggccgtggct gtggctccac tgtctggcac atgtttgtct acattgtatg  1500
tcttggacag agccacatat gggaagcggt ccatggccag gggtatctca ggccccagtt  1560
tgtccttctt ctgccctttt aggatcctgg cagctgtcac cgtagacacc cccatcccat  1620
cgcccaggaa gatgatgagg ttcttggcgg ctgtctgtgc aggctgcagc ttcttggcgg  1680
cacccagggc ctcggctgcc tcgcggttcc agaagtccgg gttctcctcc tcaactggga  1740
tgatgcccag ggagagctgt agcctcaggc ccagcagcag cagcagcagc agcatggtgg  1800
gcgaattcgc gattcgaagc ttacttagat cgcagatcca gcacaatgga tctcgaggtc  1860
gagggatctc tacagaattc tcacgacacc tgaaatggaa gaaaaaact ttgaaccact   1920
gtctgaggct tgagaatgaa ccaagatcca aactcaaaaa gggcaaattc caaggagaat  1980
tacatcaagt gccaagctgg cctaacttca gtctccaccc actcagtgtg gggaaactcc  2040
atcgcataaa accctcccc ccaacctaaa gacgacgtac tccaaaagct cgagaactaa   2100
tcgaggtgcc tggacggcgc ccggtactcc gtggagtcac atgaagcgac ggctgaggac  2160
ggaaaggccc ttttcctttg tgtgggtgac tcacccgccc gctctcccga gcgccgcgtc  2220
ctccattttg agctccctgc agcagggccg ggaagcggcc atctttccgc tcacgcaact  2280
ggtgccgacc gggccagcct tgccgcccag ggcggggcga tacacggcgg cgcgaggcca  2340
ggcaccagag caggccggcc agcttgagac tacccccgtc cgattctcgg tggccgcgct  2400
cgcaggcccc gcctcgccga acatgtgcgc tgggacgcac gggcccgtc gccgccgcg    2460
gccccaaaaa ccgaaatacc agtgtgcaga tcttggcccg catttacaag actatcttgc  2520
cagaaaaaaa gcgtcgcagc aggtcatcga aaattttaaa tggctagaga cttatcgaaa  2580
gcagcgagac aggcgcgaag gtgccaccag attcgcacgc ggcggcccca gcgcccaggc  2640
caggcctcaa ctcaagcacg aggcgaaggg gctccttaag cgcaaggcct cgaactctcc  2700
cacccacttc caacccgaag ctcgggatca agaatcacgt actgcagcca ggtggaagta  2760
attcaaggca cgcaagggcc ataaccgta aagaggccag gcccgcggga accacacacg   2820
gcacttacct gtgttctggc ggcaaaccg ttgcgaaaaa gaacgttcac ggcgactact    2880
gcacttatat acggttctcc cccaccctcg ggaaaaaggc ggagccagta cacgacatca  2940
ctttcccagt ttacccgcg ccaccttctc taggcaccgg ttcaattgcc gacccctcc    3000
cccaacttct cggggactgt gggcgatgtg cgctctgccc actgacgggc accggagcca  3060
attcccagtc gacctggtcc aaagaccaga ggctattga gactttcaa caaagggtaa    3120
tatcgggaaa cctcctcgga ttccattgcc cagctatctg tcacttcatc gaaaggacag  3180
tagaaaagga agatggcttc tacaaatgcc atcattgcga taaggaaag gctatcgttc   3240
aagatgcctc taccgacagt ggtcccaaag atggaccccc acccacgagg aacatcgtgg  3300
aaaaagaaga cgttccaacc acgtcttcaa agcaagtgga ttgatgtgat acatagtgga  3360
gcacgacact ctcgtctact ccaagaatat caaagataca gtctcagaag accagagggc  3420
tattgagact tttcaacaaa gggtaatatc gggaaacctc ctcggattcc attgccagc   3480
tatctgtcac ttcatcgaaa ggacagtaga aaggaagat ggcttctaca aatgccatca    3540
ttgcgataaa ggaaaggcta tcgttcaaga tgcctctacc gacagtggtc caaagatgg   3600
accccaccc acgaggaaca tcgtggaaaa agaagacgtt ccaaccacgt cttcaaagca   3660
agtggattga tgtgatatct ccactgacgt aagggatgac gcacaatccc actatccttc  3720
```

FIGURE 17

```
gcaagaccct tcctctatat aaggaagttc atttcatttg gagaggacac gctgagttca    3780
caacacaaat cagatttata gagagattta taaaaaaaaa aaaacatgtg atcccgggaa    3840
ttcgctagca ctagaggatc cccgggtacc ggtcgccacc ctagagtcgc ggccgcttta    3900
cttgtacagc tcgtccatgc cgagagtgat cccggcggcg gtcacgaact ccagcaggac    3960
catgtgatcg cgcttctcgt tggggtcttt gctcagggcg gactgggtgc tcaggtagtg    4020
gttgtcgggc agcagcacgg ggccgtcgcc gatggggtg ttctgctggt agtggtcggc     4080
gagctgcacg ctgccgtcct cgatgttgtg gcggatcttg aagttcacct tgatgccgtt    4140
cttctgcttg tcggccatga tatagacgtt gtggctgttg tagttgtact ccagcttgtg    4200
ccccaggatg ttgccgtcct ccttgaagtc gatgccttc agctcgatgc ggttcaccag     4260
ggtgtcgccc tcgaacttca cctcggcgcg ggtcttgtag ttgccgtcgt ccttgaagaa    4320
gatggtgcgc tcctggacgt agccttcggg catggcggac ttgaagaagt cgtgctgctt    4380
catgtggtcg gggtagcggc tgaagcactg cacgccgtag gtcagggtgg tcacgagggt    4440
gggccagggc acggcagct tgccggtggt gcagatgaac ttcagggtca gcttgccgta     4500
ggtggcatcg ccctcgccct cgccggacac gctgaacttg tggccgttta cgtcgccgtc    4560
cagctcgacc aggatgggca ccaccccggt gaacagctcc tcgcccttgc tcaccatagt    4620
ccgcaaaaat caccagtctc tctctacaaa tctatctctc tctatttttc tccagaataa    4680
tgtgtgagta gttcccagat aagggaatta gggttcttat agggtttcgc tcatgtgttg    4740
agcatataag aaaccctag tatgtatttg tatttgtaaa atacttctat caataaaatt     4800
tctaattcct aaaaccaaaa tccagtgacc gggcggcggc tcgag                    4845
```

FIGURE 17 CONT

```
gtcgacgata tcgccatttt tccaaaagtg attttgggc atacgcgata tctggcgata    60
gcgcttatat cgtttacggg ggatggcgat agacgacttt ggtgacttgg gcgattctgt   120
gtgtcgcaaa tatcgcagtt tcgatatagg tgacagacga tatgaggcta tatcgccgat   180
agaggcgaca tcaagctggc acatggccaa tgcatatcga tctatacatt gaatcaatat   240
tggccattag ccatattatt cattggttat atagcataaa tcaatattgg ctattggcca   300
ttgcatacgt tgtatccata tcataatatg tacatttata ttggctcatg tccaacatta   360
ccgccatgtt gacattgatt attgactagt aggtgtcgct aggctcagca aaattacggg   420
cccactggct cttcccacaa ccgggcgggc ccactatgac gtgtacagct gtcttccaat   480
cacgctgctg catcttcccg ctcactttca aaagttcagc cagcccgcgg aaatttctca   540
catacgttac agggaactgc tccatatgac tagttattaa tagtaatcaa ttacggggtc   600
attagttcat agcccatata tggagttccg cgttacataa cttacggtaa atggcccgcc   660
tggctgaccg cccaacgacc cccgcccatt gacgtcaata atgacgtatg ttcccatagt   720
aacgccaata gggactttcc attgacgtca atgggtggag tatttacggt aaactgccca   780
cttggcagta catcaagtgt atcatatgcc aagtacgccc cctattgacg tcaatgacgg   840
taaatggccc gcctggcatt atgcccagta catgacctta tgggactttc ctacttggca   900
gtacatctac gtattagtca tcgctattac catggtgatg cggttttggc agtacatcaa   960
tgggcgtgga tagcggtttg actcacgggg atttccaagt ctccacccca ttgacgtcaa  1020
tgggagtttg ttttggcacc aaaatcaacg ggactttcca aaatgtcgta acaactccgc  1080
cccattgacg caaatgggcg gtaggcgtgt acggtgggag gtctatataa gcagagctcg  1140
tttagtgaac cgtcagatcg cctggagacg ccatccacgc tgttttgacc tccatagaag  1200
acaccgggac cgatccagcc tccgcggccg ggaacggtgc attggaacgc ggattcccg   1260
tgccaagagt gacgtaagta ccgcctatag agtctatagg cccaccccct tggcttctta  1320
tgcatgctat actgtttttg gcttggggtc tatacacccc cgcttcctca tgttataggt  1380
gatggtatag cttagcctat aggtgtgggt tattgaccat tattgaccac tccctattg  1440
gtgacgatac tttccattac taatccataa catggctctt tgccacaact ctctttattg  1500
gctatatgcc aatacactgt ccttcagaga ctgacacgga ctctgtattt ttacaggatg  1560
gggtctcatt tattatttac aaattcacat atacaacacc accgtcccca gtgcccgcag  1620
tttttattaa acataacgtg ggatctccac gcgaatctcg ggtacgtgtt ccggacatgg  1680
gctcttctcc ggtagcggcg gagcttctac atccgagccc tgctcccatg cctccagcga  1740
ctcatggtcg ctcggcagct ccttgctcct aacagtggag gccagactta ggcacagcac  1800
gatgcccacc accaccagtg tgccgcacaa ggccgtggcg gtagggtatg tgtctgaaaa  1860
tgagctcggg gagcgggctt gcaccgctga cgcatttgga agacttaagg cagcggcaga  1920
agaagatgca ggcagctgag ttgttgtgtt ctgataagag tcagaggtaa ctcccgttgc  1980
ggtgctgtta acggtggagg gcagtgtagt ctgagcagta ctcgttgctg ccgcgcgcgc  2040
caccagacat aatagctgac agactaacag actgttcctt tccatgggtc ttttctgcag  2100
tcaccgtcct tgacacgaag cttatggaag acgccaaaaa cataaagaaa ggcccggcgc  2160
cattctatcc gctggaagat ggaaccgctg gagagcaact gcataaggct atgaagagat  2220
acgccctggt tcctggaaca attgcttttta cagatgcaca tatcgaggtg gacatcactt  2280
acgctgagta cttcgaaatg tccgttcggt tggcagaagc tatgaaacga tatgggctga  2340
atacaaatca cagaatcgtc gtatgcagtg aaaactctct tcaattcttt atgccggtgt  2400
tgggcgcgtt atttatcgga gttgcagttg cgcccgcgaa cgacatttat aatgaacgtg  2460
aattgctcaa cagtatgggc atttcgcagc ctaccgtggt gttcgtttcc aaaaaggggt  2520
tgcaaaaaat tttgaacgtg caaaaaaagc tcccaatcat ccaaaaaatt attatcatgg  2580
attctaaaac ggattaccag ggatttcagt cgatgtacac gttcgtcaca tctcatctac  2640
ctcccggttt taatgaatac gattttgtgc cagagtcctt cgatagggac aagacaattg  2700
cactgatcat gaactcctct ggatctactg gtctgcctaa aggtgtcgct gcctcata   2760
gaactgcctg cgtgagattc tcgcatgcca gagatcctat ttttggcaat caaatcattc  2820
cggatactgc gattttaagt gttgttccat tccatcacgg ttttggaatg tttactacac  2880
tcggatattt gatatgtgga tttcgagtcg tcttaatgta tagatttgaa gaagagctgt  2940
ttctgaggag ccttcaggat tacaagattc aaagtgcgct gctggtgcca acctattct   3000
ccttcttcgc caaaagcact ctgattgaca aatacgattt atctaattta cacgaaattg  3060
cttctggtgg cgctccctc  tctaaggaag tcggggaagc ggttgccaag aggttccatc  3120
tgccaggtat caggcaagga tatgggctca ctgagactac atcagctatt ctgattacac  3180
ccgaggggga tgataaaccg ggcgcggtcg gtaaagttgt tccatttttt gaagcgaagg  3240
ttgtggatct ggataccggg aaaacgctgg gcgttaatca aagaggcgaa ctgtgtgtga  3300
gaggtcctat gattatgtcc ggttatgtaa acaatccgga agcgaccaac gccttgattg  3360
acaaggatgg atggctacat tctggagaca tagcttactg ggacgaagac gaacacttct  3420
tcatcgttga ccgcctgaag tctctgatta gtacaaaagg ctatcaggtg gctcccgctg  3480
aattggaatc catcttgctc caacacccca acatcttcga cgcaggtgtc gcaggtcttc  3540
ccgacgatga cgccggtgaa cttcccgccg ccgttgttgt tttggagcac ggaaagacga  3600
tgacggaaaa agagatcgtg gattacgtcg ccagtcaagt aacaaccgcg aaaaagttgc  3660
gcggaggagt tgtgtttgtg gacgaagtac cgaaaggtct taccggaaaa ctcgacgcaa  3720
```

FIGURE 18

```
gaaaaatcag agagatcctc ataaaggcca agaagggcgg aaagatcgcc gtgtaatcta    3780
gagggcccta ttctatagtg tcacctaaat gctagagctc gctgatcagc ctcgactgtg    3840
ccttctagtt gccagccatc tgttgtttgc ccctccccg tgccttcctt gaccctggaa     3900
ggtgccactc ccactgtcct ttcctaataa aatgaggaaa ttgcatcgca ttgtctgagt    3960
aggtgtcatt ctattctggg gggtggggtg gggcaggaca gcaaggggga ggattgggaa    4020
gacaatagca ggcatgctgg ggatgcggtg ggctctatgg cttctgaggc ggaaagaacc    4080
agctggggct cgacctggtc caaagaccag agggctattg agacttttca acaaagggta    4140
atatcgggaa acctcctcgg attccattgc ccagctatct gtcacttcat cgaaaggaca    4200
gtagaaaagg aagatggctt ctacaaatgc catcattgcg ataaaggaaa ggctatcgtt    4260
caagatgcct ctaccgacag tggtcccaaa gatggacccc cacccacgag gaacatcgtg    4320
gaaaaagaag acgttccaac cacgtcttca aagcaagtgg attgatgtga tacatggtgg    4380
agcacgacac tctcgtctac tccaagaata tcaaagatac agtctcagaa gaccagaggg    4440
ctattgagac ttttcaacaa agggtaatat cgggaaacct cctcggattc cattgcccag    4500
ctatctgtca cttcatcgaa aggacagtag aaaaggaaga tggcttctac aaatgccatc    4560
attgcgataa aggaaaggct atcgttcaag atgcctctac cgacagtggt cccaaagatg    4620
gaccccccacc cacgaggaac atcgtggaaa aagaagacgt tccaaccacg tcttcaaagc    4680
aagtggattg atgtgatatc tccactgacg taagggatga cgcacaatcc cactatcctt    4740
cgcaagaccc ttcctctata taaggaagtt catttcattt ggagaggaca cgctgagttc    4800
acaacacaaa tcagatttat agagagattt ataaaaaaaa aaaaacatgt gatcccggga    4860
attcgctagc actagaggat ccccgggtac cggtcgccac cctagagtcg cggccgcttt    4920
acttgtacag ctcgtccatg ccgagagtga tcccggcggc ggtcacgaac tccagcagga    4980
ccatgtgatc gcgcttctcg ttggggtctt tgctcagggc ggactgggtg ctcaggtagt    5040
ggttgtcggg cagcagcacg gggccgtcgc cgatggggt gttctgctgg tagtggtcgg    5100
cgagctgcac gctgccgtcc tcgatgttgt ggcggatctt gaagttcacc ttgatgccgt    5160
tcttctgctt gtccgtccat atatagacgt tgtggctgtt gtagttgtac tccagcttgt    5220
gccccaggat gttgccgtcc tccttgaagt cgatgccctt cagctcgatg cggttcacca    5280
gggtgtcgcc ctcgaacttc acctcggcgc gggtcttgta gttgccgtcg tccttgaaga    5340
agatggtgcg ctcctggacg tagccttcgg gcatggcgga cttgaagaag tcgtgctgct    5400
tcatgtggtc ggggtagcgg ctgaagcact gcacgccgta ggtcagggtg gtcacgaggg    5460
tgggccaggg cacggcagc ttgccggtgg tgcagatgaa cttcagggtc agcttgccgt    5520
aggtggcatc gccctcgccc tcgccggaca cgctgaactt gtggccgttt acgtcgccgt    5580
ccagctcgac caggatgggc accaccccgg tgaacagctc ctcgcccttg ctcaccatag    5640
tccgcaaaaa tcaccagtct ctctctacaa atctatctct ctctatttt ctccagaata    5700
atgtgtgagt agttcccaga taagggaatt aggttctta tagggtttcg ctcatgtgtt    5760
gagcatataa gaaacccttg tatgtatttt gtatttgtaa aatacttcta tcaataaaat    5820
ttctaattcc taaaaccaaa atccagtgac cgggcggcgg ctcgag                   5866
```

FIGURE 18 CONT

Sal I digest of vector and SV40 ori+promoter gene and Ligation

SEQUENCE LISTING

<160> NUMBER OF SEQ ID NOS: 18

<210> SEQ ID NO 1
<211> LENGTH: 24
<212> TYPE: DNA
<213> ORGANISM: Artificial sequence
<220> FEATURE:
<223> OTHER INFORMATION: Oligonucleotide - lucQ-F

<400> SEQUENCE: 1
caactgcata aggctatgaa gaga                                          24

<210> SEQ ID NO 2
<211> LENGTH: 24
<212> TYPE: DNA
<213> ORGANISM: Artificial sequence
<220> FEATURE:
<223> OTHER INFORMATION: Oligonucleotide - lucQ-R

<400> SEQUENCE: 2
atttgtattc agcccatatc gttt                                          24

<210> SEQ ID NO 3
<211> LENGTH: 19
<212> TYPE: DNA
<213> ORGANISM: Artificial sequence
<220> FEATURE:
<223> OTHER INFORMATION: Oligonucleotide - SEAPQ-F

<400> SEQUENCE: 3
ccttgacccc gcacaggta                                                19

<210> SEQ ID NO 4
<211> LENGTH: 25
<212> TYPE: DNA
<213> ORGANISM: Artificial sequence
<220> FEATURE:
<223> OTHER INFORMATION: Oligonucleotide - SEAPQ-R

<400> SEQUENCE: 4
ggctctgtcc aagacataca atgta                                         25

<210> SEQ ID NO 5
<211> LENGTH: 23
<212> TYPE: DNA
<213> ORGANISM: Artificial sequence
<220> FEATURE:
<223> OTHER INFORMATION: Oligonucleotide - polyA35SS-F

<400> SEQUENCE: 5
agggttctta tagggtttcg ctc                                           23

<210> SEQ ID NO 6
<211> LENGTH: 19
<212> TYPE: DNA
<213> ORGANISM: Artificial sequence
<220> FEATURE:
<223> OTHER INFORMATION: Oligonucleotide - CMV-R

<400> SEQUENCE: 6

```
ccctgtaacg tatgtgaga                                                19
```

<210> SEQ ID NO 7
<211> LENGTH: 22
<212> TYPE: DNA
<213> ORGANISM: Artificial sequence
<220> FEATURE:
<223> OTHER INFORMATION: Oligonucleotide - Rep-F

<400> SEQUENCE: 7

```
tccatcgtgc gtcagatttg cg                                            22
```

<210> SEQ ID NO 8
<211> LENGTH: 3073
<212> TYPE: DNA
<213> ORGANISM: Artificial sequence
<220> FEATURE:
<223> OTHER INFORMATION: mSEAP cassette

<400> SEQUENCE: 8

```
gtcgacggat ccttatcgat tttaccacat ttgtagaggt tttacttgct ttaaaaaacc     60
tcccacacct cccctgaac  ctgaaacata aaatgaatgc aattgttgtt gttaacttgt    120
ttattgcagc ttataatggt tacaaataaa gcaatagcat cacaaatttc acaaataaag    180 cattttttc  actgcattct agttgtggtt tgtccaaact catcaatgta tcttatcatg    240
tctgctcgaa gcggccggcc gccccgactc tagagtaacc cgggtgcgcg cgtcggtgg     300 tgccggcggg gggcgccagg tcgcaggcgg tgtagggctc caggcaggcg gcgaaggcca    360
tgacgtgcgc tatgaaggtc tgctcctgca cgccgtgaac caggtgcgcc tgcgggccgc    420
gcgcgaacac cgccacgtcc tcgcctgcgt gggtctcttc gtccaggggc actgctgact    480
gctgccgata ctcggggctc ccgctctcgc tctcggtaac atccggccgg cgccgtcct    540 tgagcacata gcctggaccg tttccgtata ggaggaccgt gtaggccttc ctgtcccggg    600
ccttgccagg ggccagcccg aagatggagc tccctcgcag ggggtagcct ccgaaggaga    660
agacgtggga gtggtcggca gtgacgaggc tcagcgtgtc ctcctcgctg gtgagctggc    720 ccgcccctc  aatggcgtcg tcgaacatga tcgtctcagt cagtgcccgg taagccctgc    780
tttcatgatg accatggtcg atgcgaccac cctccacgaa gaggaagaag ccgcgggggt    840
tcctgctcag caggcgcagg gcagcctctg tcatctccat cagggagggg tccagtgtgg    900
agtctcggtg gatctcgtat tcatgtctc  caggctcaaa gagacccatg agatgggtca    960
cagacgggtc cagggaagcc tgcatgagct cagtgcggtt ccacacatac cgggcaccct   1020
ggcgcttcgc cagccattcc tgcaccagat tcttcccgtc cagcctggtc ccaccttggc   1080
tgtagtcatc tgggtactca gggtctgggg ttcccatgcg aaacatgtac tttcggcctc   1140
cacctaggat cacgtcaatg tccatgttgg agatgagctg cgtagcgatg tcctggcacc   1200
cctcctggcg ggccgaggca ggcacgtcgg cgtccgagta ccagttgcgg ttcaccgtgt   1260
gggcgtaggt gccggctggc gaggcgtgct gcactcgtgt ggtggttacc actcccactg   1320
acttccctgc tttcttggcc cgattcatca cggagatgac ctcgttgccg cgtgtcgtgt   1380
```

```
tgcactggtt aaagcgggcg gctgcactca agccaatggt ctggaagttg cccttgaccc      1440
cgcacaggta ggccgtggct gtggctccac tgtctggcac atgtttgtct acattgtatg      1500
tcttggacag agccacatat gggaagcggt ccatggccag gggtatctca ggccccagtt      1560
tgtccttctt ctgccctttt aggatcctgg cagctgtcac cgtagacacc cccatcccat      1620
cgcccaggaa gatgatgagg ttcttggcgg ctgtctgtgc aggctgcagc ttcttggcgg      1680
cacccagggc ctcggctgcc tcgcggttcc agaagtccgg gttctcctcc tcaactggga      1740
tgatgcccag ggagagctgt agcctcaggc ccagcagcag cagcagcagc agcatggtgg      1800
gcgaattcgc gattcgaagc ttacttagat cgcagatcca gcacaatgga tctcgaggtc      1860
gagggatctc tacagaattc tcacgacacc tgaaatggaa gaaaaaaact ttgaaccact      1920
gtctgaggct tgagaatgaa ccaagatcca aactcaaaaa gggcaaattc caaggagaat      1980
tacatcaagt gccaagctgg cctaacttca gtctccaccc actcagtgtg gggaaactcc      2040
atcgcataaa acccctcccc caacctaaag acgacgtac tccaaaagct cgagaactaa      2100
tcgaggtgcc tggacggcgc ccggtactcc gtggagtcac atgaagcgac ggctgaggac      2160
ggaaaggccc ttttcctttg tgtgggtgac tcacccgccc gctctcccga gcgccgcgtc      2220
ctccattttg agctccctgc agcagggccg ggaagcggcc atctttccgc tcacgcaact      2280
ggtgccgacc gggccagcct tgccgcccag ggcggggcga tacacggcgg cgcgaggcca      2340
ggcaccagag caggccggcc agcttgagac taccccgtc cgattctcgg tggccgcgct      2400
cgcaggcccc gcctcgccga acatgtgcgc tgggacgcac gggccccgtc gccgcccgcg      2460
gccccaaaaa ccgaaatacc agtgtgcaga tcttggcccg catttacaag actatcttgc      2520
cagaaaaaaa gcgtcgcagc aggtcatcaa aaattttaaa tggctagaga cttatcgaaa      2580
gcagcgagac aggcgcgaag gtgccaccag attcgcacgc ggcggcccca gcgcccaggc      2640
caggcctcaa ctcaagcacg aggcgaaggg gctccttaag cgcaaggcct cgaactctcc      2700
cacccacttc caacccgaag ctcgggatca agaatcacgt actgcagcca ggtggaagta      2760
attcaaggca cgcaagggcc ataacccgta agaggccag gcccgcggga accacacacg      2820
gcacttacct gtgttctggc ggcaaacccg ttgcgaaaaa gaacgttcac ggcgactact      2880
gcacttatat acggttctcc cccacccctcg ggaaaaaggc ggagccagta cacgacatca      2940
ctttcccagt ttaccccgcg ccaccttctc taggcaccgg ttcaattgcc gaccctcc      3000 cccaacttct cggggactgt gggcgatgtg cgctctgccc actgacgggc accggagcca      3060
attcccagtc gac                                                        3073

<210> SEQ ID NO 9
<211> LENGTH: 4845
<212> TYPE: DNA
<213> ORGANISM: Artificial sequence
<220> FEATURE:
<223> OTHER INFORMATION: mSEAP+ cassette

<400> SEQUENCE: 9
gtcgacggat ccttatcgat tttaccacat ttgtagaggt tttacttgct ttaaaaaacc        60
tcccacacct cccctgaac ctgaaacata aaatgaatgc aattgttgtt gttaacttgt       120
ttattgcagc ttataatggt tacaaataaa gcaatagcat cacaaatttc acaaataaag      180
catttttttc actgcattct agttgtggtt tgtccaaact catcaatgta tcttatcatg      240
tctgctcgaa gcggccggcc gccccgactc tagagtaacc cggtgcgcg cgtcggtgg      300 tgccggcggg gggcgccagg tcgcaggcgg tgtagggctc caggcaggcg gcgaaggcca    360
```

-continued

```
tgacgtgcgc tatgaaggtc tgctcctgca cgccgtgaac caggtgcgcc tgcgggccgc      420
gcgcgaacac cgccacgtcc tcgcctgcgt gggtctcttc gtccaggggc actgctgact      480
gctgccgata ctcggggctc ccgctctcgc tctcggtaac atccggccgg gcgccgtcct      540
tgagcacata gcctggaccg tttccgtata ggaggaccgt gtaggccttc ctgtcccggg      600
ccttgccagg ggccagcccg aagatggagc tccctcgcag ggggtagcct ccgaaggaga      660
agacgtggga gtggtcggca gtgacgaggc tcagcgtgtc ctcctcgctg gtgagctggc      720
ccgccctctc aatggcgtcg tcgaacatga tcgtctcagt cagtgcccgg taagccctgc      780
tttcatgatg accatggtcg atgcgaccac cctccacgaa gaggaagaag ccgcgggggt      840
tcctgctcag caggcgcagg gcagcctctg tcatctccat cagggagggg tccagtgtgg      900
agtctcggtg gatctcgtat ttcatgtctc caggctcaaa gagacccatg agatgggtca      960
cagacgggtc cagggaagcc tgcatgagct cagtgcggtt ccacacatac cgggcaccct     1020
ggcgcttcgc cagccattcc tgcaccagat tcttcccgtc cagcctggtc ccaccttggc     1080
tgtagtcatc tgggtactca gggtctgggg ttcccatgcg aaacatgtac tttcggcctc     1140
cacctaggat cacgtcaatg tccatgttgg agatgagctg cgtagcgatg tcctggcacc     1200
cctcctggcg ggccgaggca ggcacgtcgg cgtccgagta ccagttgcgg ttcaccgtgt     1260
gggcgtaggt gccggctggc gaggcgtgct gcactcgtgt ggtggttacc actcccactg     1320
acttccctgc tttcttggcc cgattcatca cggagatgac ctcgttgccg cgtgtcgtgt     1380
tgcactggtt aaagcgggcg gctgcactca agccaatggt ctggaagttg cccttgaccc     1440
cgcacaggta ggccgtggct gtggctccac tgtctggcac atgtttgtct acattgtatg     1500
tcttggacag agccacatat gggaagcggt ccatggccag gggtatctca ggccccagtt     1560
tgtccttctt ctgcccttt aggatcctgg cagctgtcac cgtagacacc cccatcccat     1620
cgcccaggaa gatgatgagg ttcttggcgg ctgtctgtgc aggctgcagc ttcttggcgg     1680
cacccagggc ctcggctgcc tcgcggttcc agaagtccgg gttctcctcc tcaactggga     1740
tgatgcccag ggagagctgt agcctcaggc ccagcagcag cagcagcagc agcatggtgg     1800
gcgaattcgc gattcgaagc ttacttagat cgcagatcca gcacaatgga tctcgaggtc     1860
gagggatctc tacagaattc tcacgacacc tgaaatggaa gaaaaaaact ttgaaccact     1920
gtctgaggct tgagaatgaa ccaagatcca aactcaaaaa gggcaaattc caaggagaat     1980
tacatcaagt gccaagctgg cctaacttca gtctccaccc actcagtgtg gggaaactcc     2040
atcgcataaa accccctcccc ccaacctaaa gacgacgtac tccaaaagct cgagaactaa     2100
tcgaggtgcc tggacggcgc ccggtactcc gtggagtcac atgaagcgac ggctgaggac     2160
ggaaaggccc ttttccttg tgtgggtgac tcacccgccc gctctcccga gcgccgcgtc     2220
ctccattttg agctccctgc agcagggccg ggaagcggcc atctttccgc tcacgcaact     2280
ggtgccgacc gggccagcct tgccgcccag ggcggggcga tacacggcgg cgcgaggcca     2340
ggcaccagag caggccggcc agcttgagac taccccgtc cgattctcgg tggccgcgct     2400
cgcaggcccc gcctcgccga acatgtgcgc tgggacgcac gggccccgtc gccgcccgcg     2460
gccccaaaaa ccgaaatacc agtgtgcaga tcttggcccg catttacaag actatcttgc     2520
cagaaaaaaa gcgtcgcagc aggtcatcaa aaattttaaa tggctagaga cttatcgaaa     2580
gcagcgagac aggcgcgaag gtgccaccag attcgcacgc ggcggcccca gcgcccaggc     2640
caggcctcaa ctcaagcacg aggcgaaggg gctccttaag cgcaaggcct cgaactctcc     2700
```

```
cacccacttc caacccgaag ctcgggatca agaatcacgt actgcagcca ggtggaagta    2760
attcaaggca cgcaagggcc ataacccgta agaggccag gcccgcggga accacacacg     2820
gcacttacct gtgttctggc ggcaaacccg ttgcgaaaaa gaacgttcac ggcgactact    2880
gcacttatat acggttctcc cccacccctcg gaaaaaggc ggagccagta cacgacatca    2940
ctttcccagt ttaccccgcg ccaccttctc taggcaccgg ttcaattgcc gaccccctccc   3000 cccaacttct cggggactgt gggcgatgtg cgctctgccc actgacgggc accggagcca    3060
attcccagtc gacctggtcc aaagaccaga gggctattga acttttcaa caaagggtaa     3120 tatcgggaaa cctcctcgga ttccattgcc cagctatctg tcacttcatc gaaaggacag    3180
tagaaaagga agatggcttc tacaaatgcc atcattgcga taaaggaaag gctatcgttc    3240
aagatgcctc taccgacagt ggtcccaaag atggaccccc acccacgagg aacatcgtgg    3300
aaaaagaaga cgttccaacc acgtcttcaa agcaagtgga ttgatgtgat acatggtgga    3360
gcacgacact ctcgtctact ccaagaatat caaagataca gtctcagaag accagagggc    3420
tattgagact tttcaacaaa gggtaatatc gggaaacctc ctcggattcc attgcccagc    3480
tatctgtcac ttcatcgaaa ggacagtaga aaggaagat ggcttctaca aatgccatca    3540
ttgcgataaa ggaaaggcta tcgttcaaga tgcctctacc gacagtggtc ccaaagatgg    3600
acccccaccc acgaggaaca tcgtggaaaa agaagacgtt ccaaccacgt cttcaaagca    3660
agtggattga tgtgatatct ccactgacgt aagggatgac gcacaatccc actatccttc    3720
gcaagaccct ccctctatat aaggaagttc atttcatttg gagaggacac gctgagttca    3780
caacacaaat cagatttata gagagattta taaaaaaaaa aaaacatgtg atcccgggaa    3840
ttcgctagca ctagaggatc cccgggtacc ggtcgccacc ctagagtcgc ggccgcttta    3900
cttgtacagc tcgtccatgc cgagagtgat cccggcggcg gtcacgaact ccagcaggac    3960
catgtgatcg cgcttctcgt tggggtcttt gctcagggcg gactgggtgc tcaggtagtg    4020
gttgtcgggc agcagcacgg ggccgtcgcc gatgggggtg ttctgctggt agtggtcggc    4080
gagctgcacg ctgccgtcct cgatgttgtg gcggatcttg aagttcacct tgatgccgtt    4140
cttctgcttg tcggccatga tatagacgtt gtggctgttg tagttgtact ccagcttgtg    4200
ccccaggatg ttgccgtcct ccttgaagtc gatgcccttc agctcgatgc ggttcaccag    4260
ggtgtcgccc tcgaacttca cctcggcgcg ggtcttgtag ttgccgtcgt ccttgaagaa    4320
gatggtgcgc tcctggacgt agccttcggg catggcggac ttgaagaagt cgtgctgctt    4380
catgtggtcg gggtagcggc tgaagcactg cacgccgtag gtcagggtgg tcacgagggt    4440
gggccagggc acgggcagct tgccggtggt gcagatgaac ttcagggtca gcttgccgta    4500
ggtggcatcg ccctcgccct cgccggacac gctgaacttg tggccgttta cgtcgccgtc    4560
cagctcgacc aggatgggca ccaccccggt gaacagctcc tcgcccttgc tcaccatagt    4620
ccgcaaaaat caccagtctc tctctacaaa tctatctctc tctattttc tccagaataa     4680 tgtgtgagta gttcccagat aagggaatta gggttcttat agggtttcgc tcatgtgttg    4740
agcatataag aaacccttag tatgtatttg tatttgtaaa atacttctat caataaaatt    4800
tctaattcct aaaaccaaaa tccagtgacc gggcggcggc tcgag                    4845
```

<210> SEQ ID NO 10  
<211> LENGTH: 5866  
<212> TYPE: DNA  
<213> ORGANISM: Artificial sequence  
<220> FEATURE:  
<223> OTHER INFORMATION: mluc+ cassette

<400> SEQUENCE: 10

```
gtcgacgata tcgccatttt tccaaaagtg attttggggc atacgcgata tctggcgata      60
gcgcttatat cgtttacggg ggatggcgat agacgacttt ggtgacttgg gcgattctgt     120
gtgtcgcaaa tatcgcagtt tcgatatagg tgacagacga tatgaggcta tatcgccgat     180
agaggcgaca tcaagctggc acatggccaa tgcatatcga tctatacatt gaatcaatat     240
tggccattag ccatattatt cattggttat atagcataaa tcaatattgg ctattggcca     300
ttgcatacgt tgtatccata tcataatatg tacatttata ttggctcatg tccaacatta     360
ccgccatgtt gacattgatt attgactagt aggtgtcgct aggctcagca aaattacggg     420
cccactggct cttcccacaa ccgggcgggc ccactatgac gtgtacagct gtcttccaat     480
cacgctgctg catcttcccg ctcactttca aaagttcagc cagcccgcgg aaatttctca     540
catacgttac agggaactgc tccatatgac tagttattaa tagtaatcaa ttacggggtc     600
attagttcat agcccatata tggagttccg cgttacataa cttacggtaa atggcccgcc     660
tggctgaccg cccaacgacc cccgcccatt gacgtcaata atgacgtatg ttcccatagt     720
aacgccaata gggactttcc attgacgtca atgggtggag tatttacggt aaactgccca     780
cttggcagta catcaagtgt atcatatgcc aagtacgccc cctattgacg tcaatgacgg     840
taaatggccc gcctggcatt atgcccagta catgacctta tgggactttc ctacttggca     900
gtacatctac gtattagtca tcgctattac catggtgatg cggttttggc agtacatcaa     960
tgggcgtgga tagcggtttg actcacgggg atttccaagt ctccacccca ttgacgtcaa    1020
tgggagtttg ttttggcacc aaaatcaacg ggactttcca aatgtcgta acaactccgc     1080
cccattgacg caaatgggcg gtaggcgtgt acggtgggag gtctatataa gcagagctcg    1140
tttagtgaac cgtcagatcg cctggagacg ccatccacgc tgttttgacc tccatagaag    1200
acaccgggac cgatccagcc tccgcggccg ggaacggtgc attggaacgc ggattccccg    1260
tgccaagagt gacgtaagta ccgcctatag agtctatagg cccacccccct tggcttctta    1320
tgcatgctat actgtttttg cttggggtc tatacacccc cgcttcctca tgttataggt     1380
gatggtatag cttagcctat aggtgtgggt tattgaccat tattgaccac tcccctattg    1440
gtgacgatac tttccattac taatcccataa catggctctt tgccacaact ctctttattg    1500
gctatatgcc aatacactgt ccttcagaga ctgacacgga ctctgtattt ttacaggatg    1560
gggtctcatt tattatttac aaattcacat atacaacacc accgtcccca gtgcccgcag    1620
ttttttattaa acataacgtg ggatctccac gcgaatctcg ggtacgtgtt ccggacatgg    1680
gctcttctcc ggtagcggcg gagcttctac atccgagccc tgctcccatg cctccagcga    1740
ctcatggtcg ctcggcagct ccttgctcct aacagtggag gccagactta ggcacagcac    1800
gatgcccacc accaccagtg tgccgcacaa ggccgtggcg gtagggtatg tgtctgaaaa    1860
tgagctcggg gagcgggctt gcaccgctga cgcatttgga agacttaagg cagcggcaga    1920
agaagatgca ggcagctgag ttgttgtgtt ctgataagag tcagaggtaa ctcccgttgc    1980
ggtgctgtta acggtggagg gcagtgtagt ctgagcagta ctcgttgctg ccgcgcgcgc    2040
caccagacat aatagctgac agactaacag actgttcctt tccatgggtc ttttctgcag    2100
tcaccgtcct tgacacgaag cttatggaag acgccaaaaa cataaagaaa ggcccggcgc    2160
cattctatcc gctggaagat ggaaccgctg gagagcaact gcataaggct atgaagagat    2220
acgccctggt tcctggaaca attgcttttta cagatgcaca tatcgaggtg gacatcactt    2280
```

-continued

```
acgctgagta cttcgaaatg tccgttcggt tggcagaagc tatgaaacga tatgggctga    2340
atacaaatca cagaatcgtc gtatgcagtg aaaactctct tcaattcttt atgccggtgt    2400
tgggcgcgtt atttatcgga gttgcagttg cgcccgcgaa cgacatttat aatgaacgtg    2460
aattgctcaa cagtatgggc atttcgcagc ctaccgtggt gttcgttttcc aaaaaggggt   2520 tgcaaaaaat tttgaacgtg caaaaaaagc tcccaatcat ccaaaaaatt attatcatgg    2580
attctaaaac ggattaccag ggatttcagt cgatgtacac gttcgtcaca tctcatctac    2640
ctcccggttt taatgaatac gattttgtgc cagagtcctt cgatagggac aagacaattg    2700
cactgatcat gaactcctct ggatctactg gtctgcctaa aggtgtcgct ctgcctcata    2760
gaactgcctg cgtgagattc tcgcatgcca gagatcctat ttttggcaat caaatcattc    2820
cggatactgc gattttaagt gttgttccat tccatcacgg ttttggaatg tttactacac    2880
tcggatattt gatatgtgga tttcgagtcg tcttaatgta tagatttgaa gaagagctgt    2940
ttctgaggag ccttcaggat tacaagattc aaagtcgcgt gctggtgcca accctattct    3000
ccttcttcgc caaaagcact ctgattgaca aatacgattt atctaattta cacgaaattg    3060
cttctggtgg cgctcccctc tctaaggaag tcggggaagc ggttgccaag aggttccatc    3120
tgccaggtat caggcaagga tatgggctca ctgagactac atcagctatt ctgattacac    3180
ccgaggggga tgataaaccg ggcgcggtcg gtaaagttgt tccatttttt gaagcgaagg    3240
ttgtggatct ggataccggg aaaacgctgg gcgttaatca aagaggcgaa ctgtgtgtga    3300
gaggtcctat gattatgtcc ggttatgtaa acaatccgga agcgaccaac gccttgattg    3360
acaaggatgg atggctacat tctggagaca tagcttactg ggacgaagac gaacacttct    3420
tcatcgttga ccgcctgaag tctctgatta agtacaaagg ctatcaggtg gctcccgctg    3480
aattggaatc catcttgctc caacaccccca acatcttcga cgcaggtgtc gcaggtcttc    3540
ccgacgatga cgccggtgaa cttcccgccg ccgttgttgt tttggagcac ggaaagacga    3600
tgacggaaaa agagatcgtg gattacgtcg ccagtcaagt aacaaccgcg aaaaagttgc    3660
gcggaggagt tgtgtttgtg gacgaagtac cgaaaggtct taccggaaaa ctcgacgcaa    3720
gaaaaatcag agagatcctc ataaaggcca agagggcgg aaagatcgcc gtgtaatcta    3780
gagggcccta ttctatagtg tcacctaaat gctagagctc gctgatcagc ctcgactgtg    3840
ccttctagtt gccagccatc tgttgtttgc ccctcccccg tgccttcctt gaccctggaa    3900
ggtgccactc ccactgtcct ttcctaataa aatgaggaaa ttgcatcgca ttgtctgagt    3960
aggtgtcatt ctattctggg gggtggggtg ggcaggaca gcaaggggga ggattgggaa    4020
gacaatagca ggcatgctgg ggatgcggtg gctctatgg cttctgaggc ggaaagaacc    4080
agctggggct cgacctggtc caaagaccag agggctattg agactttca acaagggta    4140 atatcgggaa acctcctcgg attccattgc ccagctatct gtcacttcat cgaaaggaca    4200
gtagaaaagg aagatggctt ctacaaatgc catcattgcg ataaaggaaa ggctatcgtt    4260
caagatgcct ctaccgacag tggtcccaaa gatggacccc cacccacgag gaacatcgtg    4320
gaaaaagaag acgttccaac cacgtcttca aagcaagtgg attgatgtga tacatggtgg    4380
agcacgacac tctcgtctac tccaagaata tcaaagatac agtctcagaa gaccagaggg    4440
ctattgagac tttttcaacaa agggtaatat cgggaaacct cctcggattc cattgcccag    4500
ctatctgtca cttcatcgaa aggacagtag aaaaggaaga tggcttctac aaatgccatc    4560
attgcgataa aggaaaggct atcgttcaag atgcctctac cgacagtggt cccaaagatg    4620
gacccccacc cacgaggaac atcgtggaaa aagaagacgt tccaaccacg tcttcaaagc    4680
```

-continued

| | |
|---|---|
| aagtggattg atgtgatatc tccactgacg taagggatga cgcacaatcc cactatcctt | 4740 |
| cgcaagaccc ttcctctata taaggaagtt catttcattt ggagaggaca cgctgagttc | 4800 |
| acaacacaaa tcagatttat agagagattt ataaaaaaaa aaaaacatgt gatcccggga | 4860 |
| attcgctagc actagaggat ccccgggtac cggtcgccac cctagagtcg cggccgcttt | 4920 |
| acttgtacag ctcgtccatg ccgagagtga tcccggcggc ggtcacgaac tccagcagga | 4980 |
| ccatgtgatc gcgcttctcg ttggggtctt tgctcagggc ggactgggtg ctcaggtagt | 5040 |
| ggttgtcggg cagcagcacg gggccgtcgc cgatggggt gttctgctgg tagtggtcgg | 5100 |
| cgagctgcac gctgccgtcc tcgatgttgt ggcggatctt gaagttcacc ttgatgccgt | 5160 |
| tcttctgctt gtcggccatg atatagacgt tgtggctgtt gtagttgtac tccagcttgt | 5220 |
| gccccaggat gttgccgtcc tccttgaagt cgatgcccct cagctcgatg cggttcacca | 5280 |
| gggtgtcgcc ctcgaacttc acctcggcgc gggtcttgta gttgccgtcg tccttgaaga | 5340 |
| agatggtgcg ctcctggacg tagccttcgg gcatggcgga cttgaagaag tcgtgctgct | 5400 |
| tcatgtggtc ggggtagcgg ctgaagcact gcacgccgta ggtcagggtg gtcacgaggg | 5460 |
| tgggccaggg cacgggcagc ttgccggtgg tgcagatgaa cttcagggtc agcttgccgt | 5520 |
| aggtggcatc gccctcgccc tcgccggaca cgctgaactt gtggccgttt acgtcgccgt | 5580 |
| ccagctcgac caggatgggc accaccccgg tgaacagctc ctcgcccttg ctcaccatag | 5640 |
| tccgcaaaaa tcaccagtct ctctctacaa atctatctct ctctattttt ctccagaata | 5700 |
| atgtgtgagt agttcccaga taagggaatt agggttctta tagggtttcg ctcatgtgtt | 5760 |
| gagcatataa gaaacccctta gtatgtattt gtatttgtaa aatacttcta tcaataaaat | 5820 |
| ttctaattcc taaaaccaaa atccagtgac cgggcggcgg ctcgag | 5866 |

<210> SEQ ID NO 11
<211> LENGTH: 6153
<212> TYPE: DNA
<213> ORGANISM: Artificial sequence
<220> FEATURE:
<223> OTHER INFORMATION: pTRAC

<400> SEQUENCE: 11

| | |
|---|---|
| aattccgccc ctagaaatat ttgcgactct tctggcatgt aatatttcgt taaatatgaa | 60 |
| gtgctccatt tttattaact ttaaataatt ggttgtacga tcactttctt atcaagcgtt | 120 |
| actaaaatgc gtcaatctct tgttcttcc atattcatat gtcaaaatct atcaaaattc | 180 |
| ttatatatct ttttcgaatt tgaagtgaaa tttcgataat ttaaaattaa atagaacata | 240 |
| tcattattta ggtgtcatat tgatttttat acttaattac taaatttggt taactttgaa | 300 |
| agtgtacatc aacgaaaaat tagtcaaacg actaaaataa ataaatatca tgtgttatta | 360 |
| agaaaattct cctataagaa tattttaata gatcatatgt ttgtaaaaaa aattaatttt | 420 |
| tactaacaca tatatttact tatcaaaaat ttgacaaagt aagattaaaa taatattcat | 480 |
| ctaacaaaaa aaaaccagaa aatgctgaaa acccggcaaa accgaaccaa tccaaaccga | 540 |
| tatagttggt ttggtttgat tttgatataa accgaaccaa ctcggtccat ttgcacccct | 600 |
| aatcataata gctttaatat ttcaagatat tattaagtta acgttgtcaa tatcctggaa | 660 |
| attttgcaaa atgaatcaag cctatatggc tgtaatatga atttaaaagc agctcgatgt | 720 |
| ggtggtaata tgtaatttac ttgattctaa aaaaatatcc caagtattaa aatttctgc | 780 |
| taggaagaag gttagctacg atttacagca aagccagaat acaaagaacc ataaagtgat | 840 |

```
tgaagctcga aatatacgaa ggaacaaata ttttaaaaa aatacgcaat gacttggaac       900
aaaagaaagt gatatatttt ttgttcttaa acaagcatcc cctctaaaga atggcagttt       960
tcctttgcat gtaactatta tgctcccttc gttacaaaaa ttttggacta ctattgggcg      1020
cggggcgcgc ccgtccaaa gaccagaggg ctattgagac ttttcaacaa agggtaatat      1080
cgggaaacct cctcggattc cattgcccag ctatctgtca cttcatcgaa aggacagtag      1140
aaaaggaaga tggcttctac aaatgccatc attgcgataa aggaaaggct atcgttcaag      1200
atgcctctac cgacagtggt cccaaagatg gaccccacc cacgaggaac atcgtggaaa      1260
aagaagacgt tccaaccacg tcttcaaagc aagtggattg atgtgataca tggtggagca      1320
cgacactctc gtctactcca agaatatcaa agatacagtc tcagaagacc agagggctat      1380
tgagactttt caacaaaggg taatatcggg aaacctcctc ggattccatt gcccagctat      1440
ctgtcacttc atcgaaagga cagtagaaaa ggaagatggc ttctacaaat gccatcattg      1500
cgataaagga aaggctatcg ttcaagatgc ctctaccgac agtggtccca agatggacc       1560 cccacccacg aggaacatcg tggaaaaaga agacgttcca ccacgtctt caaagcaagt      1620 ggattgatgt gatatctcca ctgacgtaag ggatgacgca caatcccact atccttcgca      1680
agacccttcc tctatataag gaagttcatt tcatttggag aggacacgct gaattcacaa      1740
cacaaatcag atttatagag agatttataa aaaaaaaaa acatgtctcg agctcggatc      1800
ctctagagtc cgcaaaaatc accagtctct ctctacaaat ctatctctct ctatttttct      1860
ccagaataat gtgtgagtag ttcccagata agggaattag ggttcttata gggtttcgct      1920
catgtgttga gcataataaga aacccttagt atgtatttgt atttgtaaaa tacttctatc      1980
aataaaattt ctaattccta aaaccaaaat ccagtgaccg ggcggccggc cgcccctaga      2040
aatatttgcg actcttctgg catgtaatat ttcgttaaat atgaagtgct ccatttttat      2100
taactttaaa taattggttg tacgatcact ttcttatcaa gcgttactaa aatgcgtcaa      2160
tctctttgtt cttccatatt catatgtcaa aatctatcaa aattcttata tatctttttc      2220
gaatttgaag tgaaatttcg ataatttaaa attaaataga acatatcatt atttaggtgt      2280
catattgatt tttatactta attactaaat ttggttaact ttgaaagtgt acatcaacga      2340
aaaattagtc aaacgactaa aataaataaa tatcatgtgt tattaagaaa attctcctat      2400
aagaatattt taatagatca tatgtttgta aaaaaaatta attttactaa acacatatat      2460
ttacttatca aaaatttgac aaagtaagat taaaataata ttcatctaac aaaaaaaaac      2520
cagaaaatgc tgaaaacccg gcaaaaccga accaatccaa accgatatag ttggtttggt      2580
ttgattttga tataaaccga accaactcgg tccatttgca cccctaatca aatagctttt      2640
aatatttcaa gatattatta agttaacgtt gtcaatatcc tggaaatttt gcaaaatgaa      2700
tcaagcctat atggctgtaa tatgaattta aaagcagctc gatgtggtgg taatatgtaa      2760
tttacttgat tctaaaaaaa tatcccaagt attaataatt tctgctagga agaaggttag      2820
ctacgattta cagcaaagcc agaatacaaa gaaccataaa gtgattgaag ctcgaaatat      2880
acgaaggaac aaatatttt aaaaaaatac gcaatgactt ggaacaaaag aaagtgatat      2940 atttttgtt cttaaacaag catccctct aagaatggc agttttcctt tgcatgtaac      3000
tattatgctc ccttcgttac aaaaattttg gactactatt gggcgggtgg agggggatca      3060
gattgtcgtt tccgccttc agtttaaact atcagtgttt gacaggatat attggcgggt      3120
aaacctaaga gaaagagcg tttattagaa taatcggata tttaaaggg cgtgaaaagg      3180 tttatccgtt cgtccatttg tatgtgtaca tcaccgacga gcaaggcaag accgagcgcc      3240
```

```
tttccgacgc tcaccgggct ggttgccctc ccgctgggc tggcggccgt ctatggccct    3300
gcaaacgcgc cagaaacgcc gtcgaagccg tgtgcgagac accggccgcc ggcgttgtgg    3360
atacctcgcg gaaaacttgg ccctcactga cagatgaggg gcggacgttg acacttgagg    3420
ggccgactca cccggcgcgg cgttgacaga tgaggggcag gctcgatttc ggccggcgac    3480
gtggagctgg ccagcctcgc aaatcggcga aaacgcctga ttttacgcga gtttcccaca    3540
gatgatgtgg acaagcctgg ggataagtgc cctgcggtat tgacacttga ggggcgcgac    3600
tactgacaga tgaggggcgc gatccttgac acttgagggg cagagtgctg acagatgagg    3660
ggcgcaccta ttgacatttg aggggctgtc cacaggcaga aaatccagca tttgcaaggg    3720
tttccgcccg ttttcggcc accgctaacc tgtcttttaa cctgctttta aaccaatatt    3780
tataaacctt gttttaacc agggctgcgc cctgtgcgcg tgaccgcgca cgccgaaggg    3840
gggtgccccc ccttctcgaa ccctcccggc ccgctaacgc gggcctccca tcccccagg    3900
ggctgcgccc ctcggccgcg aacggcctca ccccaaaaat ggcagcgctg gcagtccttg    3960
ccattgccgg gatcggggca gtaacgggat gggcgatcag cccgacaagc taccctatt    4020
tgtttatttt tctaaataca ttcaaatatg tatccgctca tgagacaata accctgataa    4080
atgcttcaat aatattgaaa aggaagagt atgagtattc aacatttccg tgtcgccctt    4140
attcccttt ttgcggcatt ttgccttcct gttttgctc acccagaaac gctggtgaaa    4200
gtaaaagatg ctgaagatca gttgggtgca cgagtgggtt acatcgaact ggatctcaac    4260
agcggtaaga tccttgagag ttttcgcccc gaagaacgtt ttccaatgat gagcactttt    4320
aaagttctgc tatgtggcgc ggtattatcc cgtattgacg ccgggcaaga gcaactcggt    4380
cgccgcatac actattctca gaatgacttg gttgagtact caccagtcac agaaaagcat    4440
cttacggatg gcatgacagt aagagaatta tgcagtgctg ccataaccat gagtgataac    4500
actgcggcca acttacttct gacaacgatc ggaggaccga aggagctaac cgcttttttg    4560
cacaacatgg gggatcatgt aactcgcctt gatcgttggg aaccggagct gaatgaagcc    4620
ataccaaacg acgagcgtga caccacgatg cctgtagcaa tggcaacaac gttgcgcaaa    4680
ctattaactg gcgaactact tactctagct tcccggcaac aattaataga ctggatggag    4740
gcggataaag ttgcaggacc acttctgcgc tcggcccttc cggctggctg gtttattgct    4800
gataaatctg gagccggtga gcgtgggtct cgcggtatca ttgcagcact ggggccagat    4860
ggtaagccct cccgtatcgt agttatctac acgacgggga gtcaggcaac tatggatgaa    4920
cgaaatagac agatcgctga gataggtgcc tcactgatta gcattggta actgtcagac    4980
caagtttact catatatact ttagattgat ttaaaacttc atttttaatt taaaaggatc    5040
taggtgaaga tccttttga taatctcatg accaaaatcc cttaacgtga gttttcgttc    5100
cactgagcgt cagacccgt agaaaagatc aaaggatctt cttgagatcc ttttttctg    5160
cgcgtaatct gctgcttgca acaaaaaaa ccaccgctac cagcggtggt ttgtttgccg    5220
gatcaagagc taccaactct ttttccgaag gtaactggct tcagcagagc gcagatacca    5280
aatactgtcc ttctagtgta gccgtagtta ggccaccact tcaagaactc tgtagcaccg    5340
cctacatacc tcgctctgct aatcctgtta ccagtgctg ctgccagtgg cgataagtcg    5400
tgtcttaccg ggttggactc aagacgatag ttaccggata aggcgcagcg gtcgggctga    5460
acgggggtt cgtgcacaca gcccagcttg gagcgaacga cctacaccga actgagatac    5520
ctacagcgtg agctatgaga aagcgccacg cttcccgaag ggagaaaggc ggacaggtat    5580
```

-continued

| | |
|---|---|
| ccggtaagcg gcagggtcgg aacaggagag cgcacgaggg agcttccagg gggaaacgcc | 5640 |
| tggtatcttt atagtcctgt cgggtttcgc cacctctgac ttgagcgtcg atttttgtga | 5700 |
| tgctcgtcag gggggcggag cctatggaaa aacgccagca acgcggcctt tttacggttc | 5760 |
| ctggcctttt gctggccttt tgctcacatg gactctagct agaggatcac aggcagcaac | 5820 |
| gctctgtcat cgttacaatc aacatgctac cctccgcgag atcatccgtg tttcaaaccc | 5880 |
| ggcagcttag ttgccgttct tccgaatagc atcggtaaca tgagcaaagt ctgccgcctt | 5940 |
| acaacggctc tcccgctgac gccgtccgg actgatgggc tgcctgtatc gagtggtgat | 6000 |
| tttgtgccga gctgccggtc ggggagctgt tggctggctg gtggcaggat atattgtggt | 6060 |
| gtaaacaaat tgacgcttag acaacttaat aacacattgc ggacgttttt aatgatcgaa | 6120 |
| tactaacgtc tctaccacat tgaagagcaa gct | 6153 |

<210> SEQ ID NO 12
<211> LENGTH: 5937
<212> TYPE: DNA
<213> ORGANISM: Artificial sequence
<220> FEATURE:
<223> OTHER INFORMATION: pRIC 3.0

<400> SEQUENCE: 12

| | |
|---|---|
| gaagagcgtg actccgaggg gttgcctcaa actctatctt ataaccggcg tggaggcatg | 60 |
| gaggcagggg tattttggtc attttaatag atagtggaaa atgacgtgga atttacttaa | 120 |
| agacgaagtc tttgcgacaa gggggggccc acgccgaatt taatattacc ggcgtggccc | 180 |
| ccccttatcg cgagtgcttt agcacgagcg gtccagattt aaagtagaaa atttcccgcc | 240 |
| cactagggtt aaaggtgttc acactataaa agcatatacg atgtgatggt atttgctcga | 300 |
| cctggtccaa agaccagagg gctattgaga cttttcaaca aagggtaata tcgggaaacc | 360 |
| tcctcggatt ccattgccca gctatctgtc acttcatcga aaggacagta gaaaaggaag | 420 |
| atggcttcta caaatgccat cattgcgata aaggaaaggc tatcgttcaa gatgcctcta | 480 |
| ccgacagtgg tcccaaagat ggaccccccac ccacgaggaa catcgtggaa aagaagacg | 540 |
| ttccaaccac gtcttcaaag caagtggatt gatgtgatac atggtggagc acgacactct | 600 |
| cgtctactcc aagaatatca agatacagt ctcagaagac cagagggcta ttgagacttt | 660 |
| tcaacaaagg gtaatatcgg gaaacctcct cggattccat gcccagcta tctgtcactt | 720 |
| catcgaaagg acagtagaaa aggaagatgg cttctacaaa tgccatcatt gcgataaagg | 780 |
| aaaggctatc gttcaagatg cctctaccga cagtggtccc aaagatggac ccccacccac | 840 |
| gaggaacatc gtggaaaaag aagacgttcc aaccacgtct tcaaagcaag tggattgatg | 900 |
| tgatatctcc actgacgtaa gggatgacgc acaatcccac tatccttcgc aagacccttc | 960 |
| ctctatataa ggaagttcat ttcatttgga gaggacacgc tgagttcaca acacaaatca | 1020 |
| gatttataga gagatttata aaaaaaaaaa aacatgtgat cccgggaatt cgctagcact | 1080 |
| agtaagcttg tcgactcgag ctctctagag tccgcaaaaa tcaccagtct ctctctacaa | 1140 |
| atctatctct ctctattttt ctccagaata atgtgtgagt agttcccaga taagggaatt | 1200 |
| agggttctta tagggtttcg ctcatgtgtt gagcatataa gaaacccttaa gtatgtattt | 1260 |
| gtatttgtaa atacttcta tcaataaaat ttctaattcc taaaaccaaa atccagtgac | 1320 |
| cgggcggcgg gtcgagaatg attatttat gaatatattt cattgtgcaa gtagatagaa | 1380 |
| attacatatg ttcataaca cacgaaataa acaaaaaaag acaatccaaa acaaacaccc | 1440 |
| ccaaaaaaaa taatcacttt agataaactc gtatgaggag aggcacgttc agtgactcga | 1500 |

```
cgattcccga gcaaaaaaag tctccccgtc acacatatag tgggtgacgc aattatcttt      1560
aaagtaatcc ttctgttgac ttgtcattga taacatccag tcttcgtcag gattgcaaag      1620
aattatagaa gggatcccac cttttatttt cttctttttt ccatatttag ggttgacagt      1680
gaaatcagac tggcaaccta ttaattgctt ccacaatggg acgaacttga agggatgtc       1740
gtcgatgata ttataggtgg cgtgttcatc gtagttggtg aaatcgatgg taccgttcca      1800
atagttgtgt cgtccgagac ttctagccca ggtggtcttt ccggtacgag ttggtccgca      1860
gatgtagagg ctggggtgtc ggattccatt ccttccattg tcctggttaa atcggccatc      1920
cattcaaggt cagattgagc ttgttggtat gagacaggat gtatgtaagt ataagcgtct      1980
atgcttacat ggtatagatg ggtttccctc caggagtgta gatcttcgtg gcagcgaaga      2040
tctgattctg tgaagggcga cacatacggt tcaggttgtg gagggaataa tttgttggct      2100
gaatattcca gccattgaag ttttgttgcc cattcatgag ggaattcttc cttgatcatg      2160
tcaagatatt cctccttaga cgttgcagtc tggataatag ttctccatcg tgcgtcagat      2220
ttgcgaggag agaccttatg atctcggaaa tctcctctgg ttttaatatc tccgtccttt      2280
gatatgtaat caaggacttg tttagagttt ctagctggct ggatattagg gtgatttcct      2340
tcaaaatcga aaaagaagg atccctaata caaggttttt tatcaagctg gagaagagca       2400
tgatagtggg tagtgccatc ttgatgaagc tcagaagcaa caccaaggaa gaaaataaga      2460
aaaggtgtga gtttctccca gagaaactgg aataaatcat ctctttgaga tgagcacttg      2520
ggataggtaa ggaaaacata tttagattgg agtctgaagt tcttactagc agaaggcatg      2580
ttgttgtgac tccgaggggt tgcctcaaac tctatcttat aaccggcgtg gaggcatgga      2640
ggcagggta ttttggtcat tttaatagat agtggaaaat gacgtggaat ttacttaaag       2700
acgaagtctt tgcgacaagg gggggcccac gccgaattta atattaccgg cgtggccccc      2760
ccttatcgcg agtgctttag cacgagcggt ccagatttaa agtagaaaat ttcccgccca      2820
ctagggttaa aggtgttcac actatacaag catatacgat gtgatggtat tgactagagt      2880
ttaaactatc agtgtttgac aggatatatt ggcgggtaaa cctaagagaa aagagcgttt      2940
attagaataa tcggatattt aaaagggcgt gaaaaggttt atccgttcgt ccatttgtat      3000
gtgtacatca ccgacgagca aggcaagacc gagcgccttt ccgacgctca ccgggctggt      3060
tgccctcgcc gctgggctgg cggccgtcta tggccctgca aacgcgccag aaacgccgtc      3120
gaagccgtgt gcgagacacc ggccgccggc gttgtggata cctcgcggaa aacttggccc      3180
tcactgacag atgaggggcg gacgttgaca cttgaggggc cgactcaccc ggcgcggcgt      3240
tgacagatga ggggcaggct cgatttcggc cggcgacgtg gagctggcca gcctcgcaaa      3300
tcggcgaaaa cgcctgattt tacgcgagtt tcccacagat gatgtggaca agcctgggga      3360
taagtgccct gcggtattga cacttgaggg gcgcgactac tgacagatga ggggcgcgat      3420
ccttgacact tgaggggcag agtgctgaca gatgaggggc gcacctattg acatttgagg      3480
ggctgtccac aggcagaaaa tccagcattt gcaagggttt ccgcccgttt tcggccacc       3540
gctaacctgt cttttaacct gcttttaaac caatatttat aaaccttgtt tttaaccagg      3600
gctgcgccct gtgcgcgtga ccgcgcacgc cgaagggggg tgccccccct tctcgaaccc      3660
tcccggcccg ctaacgcggg cctcccatcc ccccaggggc tgcgccctc ggccgcgaac       3720
ggcctcaccc caaaaatggc agcgctggca gtccttgcca ttgccgggat cggggcagta      3780
acgggatggg cgatcagccc gaaagctacc cctatttgtt tattttttcta aatacattca     3840
```

```
aatatgtatc cgctcatgag acaataaccc tgataaatgc ttcaataata ttgaaaaagg    3900
aagagtatga gtattcaaca tttccgtgtc gcccttattc cctttttgc ggcatttgc     3960 cttcctgttt ttgctcaccc agaaacgctg gtgaaagtaa aagatgctga agatcagttg   4020
ggtgcacgag tgggttacat cgaactggat ctcaacagcg gtaagatcct tgagagtttt   4080
cgccccgaag aacgttttcc aatgatgagc acttttaaag ttctgctatg tggcgcggta   4140
ttatcccgta ttgacgccgg gcaagagcaa ctcggtcgcc gcatacacta ttctcagaat   4200
gacttggttg agtactcacc agtcacagaa aagcatctta cggatggcat gacagtaaga   4260
gaattatgca gtgctgccat aaccatgagt gataacactg cggccaactt acttctgaca   4320
acgatcggag gaccgaagga gctaaccgct tttttgcaca catgggggga tcatgtaact   4380
cgccttgatc gttgggaacc ggagctgaat gaagccatac caaacgacga gcgtgacacc   4440
acgatgcctg tagcaatggc aacaacgttg cgcaaactat taactggcga actacttact   4500
ctagcttccc ggcaacaatt aatagactgg atggaggcgg ataaagttgc aggaccactt   4560
ctgcgctcgg ccttccggc tggctggttt attgctgata atctggagc cggtgagcgt   4620 gggtctcgcg gtatcattgc agcactgggg ccagatggta agccctcccg tatcgtagtt   4680
atctacacga cggggagtca ggcaactatg gatgaacgaa atagacagat cgctgagata   4740
ggtgcctcac tgattaagca ttggtaactg tcagaccaag tttactcata tatactttag   4800
attgatttaa aacttcattt ttaatttaaa aggatctagg tgaagatcct ttttgataat   4860
ctcatgacca aaatccctta acgtgagttt tcgttccact gagcgtcaga ccccgtagaa   4920
aagatcaaag gatcttcttg agatcctttt tttctgcgcg taatctgctg cttgcaaaca   4980
aaaaaaccac cgctaccagc ggtggtttgt ttgccggatc aagagctacc aactcttttt   5040
ccgaaggtaa ctggcttcag cagagcgcag ataccaaata ctgttcttct agtgtagccg   5100
tagttaggcc accacttcaa gaactctgta gcaccgccta catacctcgc tctgctaatc   5160
ctgttaccag tggctgctgc cagtggcgat aagtcgtgtc ttaccgggtt ggactcaaga   5220
cgatagttac cggataaggc gcagcggtcg ggctgaacgg ggggttcgtg cacacagccc   5280
agcttggagc gaacgaccta caccgaactg agatacctac agcgtgagct atgagaaagc   5340
gccacgcttc ccgaagggag aaaggcggac aggtatccgg taagcggcag gtcggaaca   5400 ggagagcgca cgagggagct tccaggggga aacgcctggt atctttatag tcctgtcggg   5460
tttcgccacc tctgacttga gcgtcgattt ttgtgatgct cgtcaggggg gcggagccta   5520
tggaaaaacg ccagcaacgc ggcctttta cggttcctgg ccttttgctg gccttttgct   5580
cacatggact ctagctagag gatcacaggc agcaacgctc tgtcatcgtt acaatcaaca   5640
tgctaccctc cgcgagatca tccgtgtttc aaacccggca gcttagttgc cgttcttccg   5700
aatagcatcg gtaacatgag caaagtctgc cgccttacaa cggctctccc gctgacgccg   5760
tcccggactg atgggctgcc tgtatcgagt ggtgattttg tgccgagctg ccggtcgggg   5820
agctgttggc tggctggtgg caggatatat tgtggtgtaa acaaattgac gcttagacaa   5880
cttaataaca cattgcggac gtttttaatg atcgaatact aacgtctcta ccacatt      5937
```

<210> SEQ ID NO 13
<211> LENGTH: 1548
<212> TYPE: DNA
<213> ORGANISM: Artificial sequence
<220> FEATURE:
<223> OTHER INFORMATION: Human-codon optimised HPV-16 L1

<400> SEQUENCE: 13

```
ttaattaagc ttgaattcgc cgccaccatg tccctgtggc tgcccagcga ggccaccgtg      60
tacctgcccc ccgtgcccgt gagcaaggtg gtgagcaccg atgagtacgt ggcccggacc     120
aacatctact accacgccgg cacctccaga ctgctggccg tgggccaccc ctacttcccc     180
atcaagaagc ccaacaacaa caagatcctg gtgcccaagg tgagcggcct gcaataccgg     240
gtgttcagaa tccacctgcc cgaccccaat aagttcggct tccccgacac cagcttctac     300
aaccccgaca cccagagact ggtgtgggcc tgcgtgggcg tggaggtggg cagaggccag     360
cctctgggcg tgggcatcag cggccaccct ctgctgaaca agctggacga caccgagaac     420
gccagcgcct acgccgccaa cgccggcgtg ataacagag aatgcatcag catggactac     480
aagcagaccc agctgtgcct catcggctgc aagcccccca tcggcgagca ctggggcaag     540
ggcagccccc tgcaccaacgt ggccgtgaat cctggcgact gtcctcccct ggaactcatc     600
aacaccgtga tccaggacgg cgacatggtg gacaccggct tcggcgccat ggacttcacc     660
accctccagg ccaataagag cgaggtgccc ctggacatct gcaccagcat ctgcaagtac     720
cccgactaca tcaagatggt gagcgagccc tacggcgata gcctgttctt ctacctgcgg     780
cgggagcaga tgttcgtgcg cgcacctgttc aacagagccg cgccgtggg cgagaacgtg     840 cccgacgacc tgtacatcaa gggcagcggc agcaccgcca acctggccag cagcaactac     900
ttccctaccc ccagcggctc catggtgacc agcgacgccc agatcttcaa caagccctac     960
tggctccaga gagcccaggg ccacaacaat ggcatctgct ggggcaacca gctgttcgtg    1020
accgtggtgg ataccacccg gagcaccaac atgtccctgt gcgccgccat cagcaccagc    1080
gagaccacct acaagaacac caacttcaag gagtacctga ggcacggcga ggagtacgac    1140
ctccagttca tcttccagct gtgcaagatc ccctcaccg ccgacgtgat gacctacatc    1200
cacagcatga acagcaccat cctggaggac tggaacttcg gcctgcagcc ccctcctggc    1260
ggcaccctgg aggacaccta cagattcgtg accagccagg ccatcgcatg ccagaagcac    1320
acccctcccg cccctaagga ggacccccctg aagaagtaca ccttctggga ggtgaacctg    1380
aaggagaagt tcagcgccga cctggaccag ttccctctgg gcagaaagtt cctgctgcaa    1440
gccggcctga aggccaagcc taagttcacc ctgggcaaga gaaaggccac ccccaccaca    1500
agcagcacca gcaccaccgc caagcggaag aagcgcaagc tgtgatag                 1548
```

<210> SEQ ID NO 14  
<211> LENGTH: 1440  
<212> TYPE: DNA  
<213> ORGANISM: Artificial sequence  
<220> FEATURE:  
<223> OTHER INFORMATION: Human-codon optimised HPV-16 L2

<400> SEQUENCE: 14

```
tctagagcca ccatgaggca aagaggagc gccaagagga ccaagagggc cagcgccacc      60
cagctgtaca agacctgcaa gcaggccggc acctgccccc ccgacatcat ccccaaggtg     120
gagggcaaga ccatcgccga ccagatcctg cagtacggca gcatgggcgt gttcttcggc     180
ggcctgggca tcggcaccgg cagcggcacc ggcggcagga ccggctacat ccccctgggc     240
accaggcccc ccaccgccac cgacaccctg gcccccgtga ggccccccct gaccgtggac     300 ccgtgggcc ccagcgaccc cagcatcgtg agcctggtgg aggagaccag cttcatcgac     360
gccggcgccc ccaccagcgt gcccagcatc cccccgacg tgagcggctt cagcatcacc     420
accagcaccg acaccacccc cgccatcctg gacatcaaca acaccgtgac caccgtgacc     480
```

```
acccacaaca accccaccctt caccgacccc agcgtgctgc agccccccac ccccgccgag        540
accggcggcc acttcaccct gagcagcagc accatcagca cccacaacta cgaggagatc        600
cccatggaca ccttcatcgt gagcaccaac cccaacaccg tgaccagcag caccccccatc       660 cccggcagca ggcccgtggc caggctgggc ctgtacagca ggaccaccca gcaggtgaag        720
gtggtggacc ccgccttcgt gaccaccccc accaagctga tcacctacga caaccccgcc       780
tacgagggca tcgacgtgga caacaccctg tacttcagca gcaacgacaa cagcatcaac       840
atcgcccccg accccgactt cctggacatc gtggccctgc acaggcccgc cctgaccagc       900
aggaggaccg gcatcaggta cagcaggatc ggcaacaagc agaccctgag gaccaggagc       960
ggcaagagca tcggcgccaa ggtgcactac tactacgacc tgagcaccat cgaccccgcc      1020
gaggagatcg agctgcagac catcaccccc agcacctaca ccaccaccag ccacgccgcc      1080
agccccacca gcatcaacaa cggcctgtac gacatctacg ccgacgactt catcaccgac      1140
accagcacca ccccgtgcc cagcgtgccc agcaccagcc tgagcggcta catccccgcc       1200
aacaccacca tcccttcgg cggcgcctac aacatccccc tggtgagcgg ccccgacatc       1260
cccatcaaca tcaccgacca ggccccccagc ctgatcccca tcgtgcccgg cagccccag     1320 tacaccatca tcgccgacgc cggcgacttc tacctgcacc ccagctacta catgctgagg      1380
aagaggagga agaggctgcc ctacttcttc agcgacgtga gcctggccgc ctgaaagctt      1440

<210> SEQ ID NO 15
<211> LENGTH: 8310
<212> TYPE: DNA
<213> ORGANISM: Artificial sequence
<220> FEATURE:
<223> OTHER INFORMATION: pRIC3 mSEAP SV40ori

<400> SEQUENCE: 15
gaagagcgtg actccgaggg gttgcctcaa actctatctt ataaccggcg tggaggcatg         60
gaggcagggg tattttggtc attttaatag atagtggaaa atgacgtgga atttacttaa       120
agacgaagtc tttgcgacaa gggggggccc acgccgaatt taatattacc ggcgtggccc       180
ccccttatcg cgagtgcttt agcacgagcg gtccagattt aaagtagaaa atttcccgcc       240
cactagggtt aaaggtgttc acactataaa agcatatacg atgtgatggt atttggtcga      300
cacgcgtcac gtgagctttt tgcaaaagcc taggcctcca aaaaagcctc ctcactactt       360
ctggaatagc tcagaggcag aggcggcctc ggcctctgca taaataaaaa aaattagtca      420
gccatggggc ggagaatggg cggaactggg cggagttagg ggcgggatgg gcggagttag      480
gggcgggact atggttgctg actaattgag atgcttgctt tgcatacttc tgcctgctgg      540
ggagcctggg gactttccac acctggttgc tgactaattg agatgcttgc tttgcatact      600
tctgcctgcc tggggagcct ggggactttc cacaccgtcg acggatcctt atcgatttta      660
ccacatttgt agaggtttta cttgctttaa aaaacctccc acacctcccc ctgaacctga      720
aacataaaat gaatgcaatt gttgttgtta acttgtttat tgcagcttat aatggttaca      780
aataaagcaa tagcatcaca aatttcacaa ataaagcatt ttttcactg cattctagtt       840 gtggtttgtc caaactcatc aatgtatctt atcatgtctg ctcgaagcgg ccggccgccc      900
cgactctaga gtaacccggg tgcgcggcgt cggtggtgcc ggcgggggc gccaggtcgc       960 aggcggtgta gggctccagg caggcggcga aggccatgac gtgcgctatg aaggtctgct     1020
cctgcacgcc gtgaaccagg tgcgcctgcg ggccgcgcgc gaacaccgcc acgtcctcgc     1080
ctgcgtgggt ctcttcgtcc aggggcactg ctgactgctg ccgatactcg ggctcccgc      1140
```

```
tctcgctctc ggtaacatcc ggccgggcgc cgtccttgag cacatagcct ggaccgtttc    1200
cgtataggag gaccgtgtag gccttcctgt cccgggcctt gccaggggcc agcccgaaga    1260
tggagctccc tcgcaggggg tagcctccga aggagaagac gtgggagtgg tcggcagtga    1320
cgaggctcag cgtgtcctcc tcgctggtga gctggcccgc cctctcaatg cgtcgtcga    1380 acatgatcgt ctcagtcagt gcccggtaag ccctgctttc atgatgacca tggtcgatgc    1440
gaccaccctc cacgaagagg aagaagccgc gggggttcct gctcagcagg cgcagggcag    1500
cctctgtcat ctccatcagg gaggggtcca gtgtggagtc tcggtggatc tcgtatttca    1560
tgtctccagg ctcaaagaga cccatgagat gggtcacaga cgggtccagg aagcctgca    1620 tgagctcagt gcggttccac acataccggg caccctggcg cttcgccagc cattcctgca    1680
ccagattctt cccgtccagc ctggtcccac cttggctgta gtcatctggg tactcagggt    1740
ctggggttcc catgcgaaac atgtactttc ggcctccacc taggatcacg tcaatgtcca    1800
tgttggagat gagctgcgta gcgatgtcct ggcaccctc ctggcgggcc gaggcaggca    1860
cgtcggcgtc cgagtaccag ttgcggttca ccgtgtgggc gtaggtgccg gctggcgagg    1920
cgtgctgcac tcgtgtggtg gttaccactc ccactgactt ccctgctttc ttggcccgat    1980
tcatcacgga gatgacctcg ttgccgcgtg tcgtgttgca ctggttaaag cgggcggctg    2040
cactcaagcc aatggtctgg aagttgccct tgacccgca caggtaggcc gtggctgtgg    2100
ctccactgtc tggcacatgt ttgtctacat tgtatgtctt ggacagagcc acatatggga    2160
agcggtccat ggccagggt atctcaggcc ccagtttgtc cttcttctgc ccttttagga    2220
tcctggcagc tgtcaccgta gacaccccca tcccatcgcc caggaagatg atgaggttct    2280
tggcggctgt ctgtgcaggc tgcagcttct tggcggcacc cagggcctcg gctgcctcgc    2340
ggttccagaa gtccgggttc tcctcctcaa ctgggatgat gcccagggag agctgtagcc    2400
tcaggcccag cagcagcagc agcagcagca tggtgggcga attcgcgatt cgaagcttac    2460
ttagatcgca gatccagcac aatggatctc gaggtcgagg gatctctaca gaattctcac    2520
gacacctgaa atggaagaaa aaactttga accactgtct gaggcttgag aatgaaccaa    2580
gatccaaact caaaagggc aaattccaag gagaattaca tcaagtgcca agctggccta    2640
acttcagtct ccaccactc agtgtgggga aactccatcg cataaaaccc ctcccccaa    2700 cctaaagacg acgtactcca aaagctcgag aactaatcga ggtgcctgga cggcgcccgg    2760
tactccgtgg agtcacatga agcgacggct gaggacggaa aggccctttt cctttgtgtg    2820
ggtgactcac ccgcccgctc tcccgagcgc cgcgtcctcc attttgagct ccctgcagca    2880
gggccgggaa gcggccatct ttccgctcac gcaactggtg ccgaccgggc cagccttgcc    2940
gcccagggcg gggcgataca cggcggcgcg aggccaggca ccagagcagg ccggccagct    3000
tgagactacc cccgtccgat tctcggtggc cgcgctcgca ggccccgcct cgccgaacat    3060
gtgcgctggg acgcacgggc cccgtcgccg ccgcggcccc aaaaaccga ataccagtg    3120 tgcagatctt ggcccgcatt tacaagacta tcttgccaga aaaaaagcgt cgcagcaggt    3180
catcaaaaat tttaaatggc tagagactta tcgaaagcag cgagacaggc gcgaaggtgc    3240
caccagattc gcacgcggcg gccccagcgc ccaggccagg cctcaactca agcacgaggc    3300 gaagggctc cttaagcgca aggcctcgaa ctctcccacc cacttccaac ccgaagctcg    3360
ggatcaagaa tcacgtactg cagccaggtg gaagtaattc aaggcacgca agggccataa    3420
cccgtaaaga ggccaggccc gcgggaacca cacacgcac ttacctgtgt tctggcggca    3480
```

```
aacccgttgc gaaaaagaac gttcacggcg actactgcac ttatatacgg ttctccccca    3540
ccctcgggaa aaaggcggag ccagtacacg acatcacttt cccagtttac cccgcgccac    3600
cttctctagg caccggttca attgccgacc cctccccca acttctcggg gactgtgggc     3660
gatgtgcgct ctgcccactg acgggcaccg gagccaattc ccagtcgaga atgattattt    3720
tatgaatata tttcattgtg caagtagata gaaattacat atgttacata acacacgaaa    3780
taaacaaaaa aagacaatcc aaaaacaaac acccaaaaa aataatcac tttagataaa      3840 ctcgtatgag gagaggcacg ttcagtgact cgacgattcc cgagcaaaaa aagtctcccc    3900
gtcacacata tagtgggtga cgcaattatc tttaaagtaa tccttctgtt gacttgtcat    3960
tgataacatc cagtcttcgt caggattgca aagaattata gaagggatcc cacctttat     4020 tttcttcttt tttccatatt tagggttgac agtgaaatca gactggcaac ctattaattg    4080
cttccacaat gggacgaact tgaaggggat gtcgtcgatg atattatagg tggcgtgttc    4140
atcgtagttg gtgaaatcga tggtaccgtt ccaatagttg tgtcgtccga gacttctagc    4200
ccaggtggtc tttccggtac gagttggtcc gcagatgtag aggctggggt gtcggattcc    4260
attccttcca ttgtcctggt taaatcggcc atccattcaa ggtcagattg agcttgttgg    4320
tatgagacag gatgtatgta agtataagcg tctatgctta catggtatag atgggtttcc    4380
ctccaggagt gtagatcttc gtggcagcga agatctgatt ctgtgaaggg cgacacatac    4440
ggttcaggtt gtggagggaa taatttgttg gctgaatatt ccagccattg aagttttgtt    4500
gcccattcat gagggaattc ttccttgatc atgtcaagat attcctcctt agacgttgca    4560
gtctggataa tagttctcca tcgtgcgtca gatttgcgag gagagacctt atgatctcgg    4620
aaatctcctc tggttttaat atctccgtcc tttgatatgt aatcaaggac ttgtttagag    4680
tttctagctg gctggatatt agggtgattt ccttcaaaat cgaaaaaga aggatcccta    4740 atacaaggtt ttttatcaag ctggagaaga gcatgatagt gggtagtgcc atcttgatga    4800
agctcagaag caacaccaag gaagaaaata agaaaaggtg tgagtttctc ccagagaaac    4860
tggaataaat catctctttg agatgagcac ttgggatagg taaggaaaac atatttagat    4920
tggagtctga agttcttact agcagaaggc atgttgttgt gactccgagg ggttgcctca    4980
aactctatct tataaccggc gtggaggcat ggaggcaggg gtattttggt cattttaata    5040
gatagtggaa aatgacgtgg aatttactta aagacgaagt ctttgcgaca agggggggcc    5100
cacgccgaat ttaatattac cggcgtggcc ccccttatc gcgagtgctt tagcacgagc     5160
ggtccagatt taaagtagaa aatttcccgc ccactagggt taaaggtgtt cacactatac    5220
aagcatatac gatgtgatgg tattgactag agtttaaact atcagtgttt gacaggatat    5280
attggcgggt aaacctaaga gaaaagagcg tttattagaa taatcggata tttaaaaggg    5340
cgtgaaaagg tttatccgtt cgtccatttg tatgtgtaca tcaccgacga gcaaggcaag    5400
accgagcgcc tttccgacgc tcaccgggct ggttgccctc gccgctgggc tggcggccgt    5460 ctatggcccct gcaaacgcgc cagaaacgcc gtcgaagccg tgtgcgagac accggccgcc    5520
ggcgttgtgg atacctcgcg gaaaacttgg ccctcactga cagatgaggg gcggacgttg    5580
acacttgagg ggccgactca cccggcgcgg cgttgacaga tgaggggcag gctcgatttc    5640
ggccggcgac gtggagctgg ccagcctcgc aaatcggcga aaacgcctga ttttacgcga    5700
gtttcccaca gatgatgtgg acaagcctgg ggataagtgc cctgcggtat tgacacttga    5760
ggggcgcgac tactgacaga tgaggggcgc gatccttgac acttgagggg cagagtgctg    5820
acagatgagg ggcgcaccta ttgacatttg aggggctgtc cacaggcaga aaatccagca    5880
```

```
tttgcaaggg tttccgcccg tttttcggcc accgctaacc tgtcttttaa cctgctttta   5940
aaccaatatt tataaacctt gttttaacc agggctgcgc cctgtgcgcg tgaccgcgca    6000
cgccgaaggg gggtgccccc ccttctcgaa ccctcccggc ccgctaacgc gggcctccca   6060
tcccccagg ggctgcgccc ctcggccgcg aacggcctca ccccaaaaat ggcagcgctg    6120
gcagtccttg ccattgccgg gatcggggca gtaacgggat gggcgatcag cccgaaagct   6180
acccctattt gtttattttt ctaaatacat tcaaatatgt atccgctcat gagacaataa   6240
ccctgataaa tgcttcaata atattgaaaa aggaagagta tgagtattca acatttccgt   6300
gtcgcccta ttccctttt tgcggcattt tgccttcctg ttttgctca cccagaaacg     6360
ctggtgaaag taaaagatgc tgaagatcag ttgggtgcac gagtgggtta catcgaactg   6420
gatctcaaca gcggtaagat ccttgagagt tttcgccccg aagaacgttt tccaatgatg   6480
agcacttta aagttctgct atgtggcgcg gtattatccc gtattgacgc cgggcaagag    6540
caactcggtc gccgcataca ctattctcag aatgacttgg ttgagtactc accagtcaca   6600
gaaaagcatc ttacggatgg catgacagta agagaattat gcagtgctgc cataaccatg   6660
agtgataaca ctgcggccaa cttacttctg acaacgatcg gaggaccgaa ggagctaacc   6720
gcttttttgc acaacatggg ggatcatgta actcgccttg atcgttggga accggagctg   6780
aatgaagcca taccaaacga cgagcgtgac accacgatgc ctgtagcaat ggcaacaacg   6840
ttgcgcaaac tattaactgg cgaactactt actctagctt cccggcaaca attaatagac   6900
tggatggagg cggataaagt tgcaggacca cttctgcgct cggcccttcc ggctggctgg   6960
tttattgctg ataaatctgg agccggtgag cgtgggtctc gcggtatcat tgcagcactg   7020
gggccagatg gtaagccctc ccgtatcgta gttatctaca cgacggggag tcaggcaact   7080
atggatgaac gaaatagaca gatcgctgag ataggtgcct cactgattaa gcattggtaa   7140
ctgtcagacc aagtttactc atatatactt tagattgatt taaaacttca tttttaattt   7200
aaaaggatct aggtgaagat cctttttgat aatctcatga ccaaaatccc ttaacgtgag   7260
ttttcgttcc actgagcgtc agaccccgta gaaaagatca aaggatcttc ttgagatcct   7320
ttttttctgc gcgtaatctg ctgcttgcaa acaaaaaaac caccgctacc agcggtggtt   7380
tgtttgccgg atcaagagct accaactctt tttccgaagg taactggctt cagcagagcg   7440
cagataccaa atactgttct tctagtgtag ccgtagttag gccaccactt caagaactct   7500
gtagcaccgc ctacatacct cgctctgcta atcctgttac cagtggctgc tgccagtggc   7560
gataagtcgt gtcttaccgg gttggactca agacgatagt taccggataa ggcgcagcgg   7620
tcgggctgaa cggggggttc gtgcacacag cccagcttgg agcgaacgac ctacaccgaa   7680
ctgagatacc tacagcgtga gctatgagaa agcgccacgc ttcccgaagg gagaaaggcg   7740
gacaggtatc cggtaagcgg cagggtcgga acaggagagc gcacgaggga gcttccaggg   7800
ggaaacgcct ggtatcttta tagtcctgtc gggtttcgcc acctctgact tgagcgtcga   7860
tttttgtgat gctcgtcagg gggcggagc ctatggaaaa acgccagcaa cgcggccttt    7920
ttacggttcc tggccttttg ctggcctttt gctcacatgg actctagcta aggatcaca    7980
ggcagcaacg ctctgtcatc gttacaatca acatgctacc ctccgcgaga tcatccgtgt   8040
ttcaaacccg gcagcttagt tgccgttctt ccgaatagca tcggtaacat gagcaaagtc   8100
tgccgcctta caacgctct cccgctgacg ccgtcccgga ctgatgggct gcctgtatcg    8160
agtggtgatt ttgtgccgag ctgccggtcg gggagctgtt ggctggctgg tggcaggata   8220
```

```
tattgtggtg taaacaaatt gacgcttaga caacttaata acacattgcg gacgttttta    8280
atgatcgaat actaacgtct ctaccacatt                                    8310

<210> SEQ ID NO 16
<211> LENGTH: 10085
<212> TYPE: DNA
<213> ORGANISM: Artificial sequence
<220> FEATURE:
<223> OTHER INFORMATION: pRIC3 mSEAP+ SV40ori

<400> SEQUENCE: 16
gaagagcgtg actccgaggg gttgcctcaa actctatctt ataaccggcg tggaggcatg      60
gaggcagggg tattttggtc attttaatag atagtggaaa atgacgtgga atttacttaa     120
agacgaagtc tttgcgacaa ggggggggccc acgccgaatt taatattacc ggcgtggccc    180 cccccttatcg cgagtgcttt agcacgagcg gtccagattt aaagtagaaa atttcccgcc    240
cactagggtt aaaggtgttc aactataaaa agcatatacg atgtgatggt atttggtcga    300
cacgcgtcac gtgagctttt tgcaaaagcc taggcctcca aaaaagcctc ctcactactt    360
ctggaatagc tcagaggcag aggcggcctc ggcctctgca taaataaaaa aaattagtca    420
gccatggggc ggagaatggg cggaactggg cggagttagg ggcgggatgg gcggagttag    480
gggcgggact atggttgctg actaattgag atgcttgctt tgcatacttc tgcctgctgg    540
ggagcctggg gactttccac acctggttgc tgactaattg agatgcttgc tttgcatact    600
tctgcctgcc tggggagcct ggggactttc cacaccgtcg acggatcctt atcgatttta    660
ccacatttgt agaggtttta cttgctttaa aaaacctccc acacctcccc ctgaacctga    720
aacataaaat gaatgcaatt gttgttgtta acttgtttat tgcagcttat aatggttaca    780
aataaagcaa tagcatcaca aatttcacaa ataaagcatt ttttttcactg cattctagtt    840 gtggtttgtc caaactcatc aatgtatctt atcatgtctg ctcgaagcgg ccggccgccc    900
cgactctaga gtaacccggg tgcgcggcgt cggtggtgcc ggcgggggc gccaggtcgc    960 aggcggtgta gggctccagg caggcggcga aggccatgac gtgcgctatg aaggtctgct   1020
cctgcacgcc gtgaaccagg tgcgcctgcg ggccgcgcgc gaacaccgcc acgtcctcgc   1080
ctgcgtgggt ctcttcgtcc aggggcactg ctgactgctg ccgatactcg ggctcccgc    1140 tctcgctctc ggtaacatcc ggccgggcgc cgtccttgag cacatagcct ggaccgtttc   1200
cgtataggag gaccgtgtag gccttcctgt cccgggcctt gccaggggcc agcccgaaga   1260
tggagctccc tcgcaggggg tagcctccga aggagaagac gtgggagtgg tcggcagtga   1320
cgaggctcag cgtgtcctcc tcgctggtga gctggcccgc cctctcaatg gcgtcgtcga   1380
acatgatcgt ctcagtcagt gcccggtaag ccctgctttc atgatgacca tggtcgatgc   1440
gaccaccctc cacgaagagg aagaagccgc gggggttcct gctcagcagg cgcagggcag   1500
cctctgtcat ctccatcagg gaggggtcca gtgtggagtc tcggtggatc tcgtatttca   1560
tgtctccagg ctcaaagaga cccatgagat gggtcacaga cgggtccagg gaagcctgca   1620
tgagctcagt gcggttccac acataccggg caccctggcg cttcgccagc cattcctgca   1680
ccagattctt cccgtccagc ctggtccac cttggctgta gtcatctggg tactcagggt    1740
ctggggttcc catgcgaaac atgtactttc ggcctccacc taggatcacg tcaatgtcca   1800
tgttggagat gagctgcgta gcgatgtcct ggcacccctc ctggcgggcc gaggcaggca   1860
cgtcggcgtc cgagtaccag ttgcggttca ccgtgtgggc gtaggtgccg gctggcgagg   1920
cgtgctgcac tcgtgtggtg gttaccactc ccactgactt ccctgctttc ttggcccgat   1980
```

```
tcatcacgga gatgacctcg ttgccgcgtg tcgtgttgca ctggttaaag cgggcggctg    2040
cactcaggcc aatggtctgg aagttgccct tgacccccgca caggtaggcc gtggctgtgg   2100
ctccactgtc tggcacatgt ttgtctacat tgtatgtctt ggacagagcc acatatggga    2160
agcggtccat ggccagggt atctcaggcc ccagtttgtc cttcttctgc ccttttagga     2220
tcctggcagc tgtcaccgta gacaccccca tcccatcgcc caggaagatg atgaggttct    2280
tggcggctgt ctgtgcaggc tgcagcttct tggcggcacc cagggcctcg gctgcctcgc    2340
ggttccagaa gtccgggttc tcctcctcaa ctgggatgat gcccagggag agctgtagcc    2400
tcaggcccag cagcagcagc agcagcagca tggtgggcga attcgcgatt cgaagcttac    2460
ttagatcgca gatccagcac aatggatctg gaggtcgagg gatctctaga gaattcctca    2520
cgacacctga aatggaagaa aaaaactttg aaccactgtc tgaggcttga gaatgaacca    2580
agatccaaac tcaaaaaggg caaattccaa ggagaattac atcaagtgcc aagctggcct    2640
aacttcagtc tccacccact cagtgtgggg aaactccatc gcataaaacc cctcccccca    2700
acctaaagac gacgtactcc aaaagctcga gaactaatcg aggtgcctgg acggcgcccg    2760
gtactccgtg gagtcacatg aagcgacggc tgaggacgga aaggcccttt tccttttgtgt  2820 gggtgactca cccgcccgct ctcccgagcg ccgcgtcctc cattttgagc tccctgcagc    2880
agggccggga agcggccatc tttccgctca cgcaactggt gccgaccggg ccagccttgc    2940
cgcccagggc ggggcgatac acggcggcgc gaggccaggc accagagcag gccggccagc    3000
ttgagactac ccccgtccga ttctcggtgg ccgcgctcgc aggccccgcc tcgccgaaca    3060
tgtgcgctgg gacgcacggg ccccgtcgcc gcccgcggcc ccaaaaaccg aaataccagt    3120
gtgcagatct tggcccgcat ttacaagact atcttgccag aaaaaaagcg tcgcagcagg    3180
tcatcaaaaa ttttaaatgg ctagagactt atcgaaagca gcgagacagg cgcgaaggtg    3240
ccaccagatt cgcacgcggc ggccccagcg cccaggccag gcctcaactc aagcacgagg    3300
cgaaggggct ccttaagcgc aaggcctcga actctcccac ccacttccaa cccgaagctc    3360
gggatcaaga atcacgtact gcagccaggt ggaagtaatt caaggcacgc aagggccata    3420
acccgtaaag aggccaggcc cgcgggaacc acacacggca cttacctgtg ttctggcggc    3480
aaacccgttg cgaaaaagaa cgttcacggc gactactgca cttatatacg gttctccccc    3540
accctcggga aaaaggcgga gccagtacac gacatcactt tcccagttta ccccgcgcca    3600
ccttctctag gcaccggttc aattgccgac ccctccccca aacttctcgg ggactgtggg    3660
cgatgtgcgc tctgcccact gacgggcacc ggagccaatt cccagtcgac ctggtccaaa    3720
gaccagaggg ctattgagac ttttcaacaa agggtaatat cgggaaacct cctcggattc    3780
cattgcccag ctatctgtca cttcatcgaa aggacagtag aaaaggaaga tggcttctac    3840
aaatgccatc attgcgataa aggaaaggct atcgttcaag atgcctctac cgacagtggt    3900
cccaaagatg gacccccacc cacgaggaac atcgtggaaa aagaagacgt tccaaccacg    3960
tcttcaaagc aagtggattg atgtgataca tggtggagca cgacactctc gtctactcca    4020
agaatatcaa agatacagtc tcagaagacc agagggctat tgagactttt caacaaaggg    4080
taatatcggg aaacctcctc ggattccatt gcccagctat ctgtcacttc atcgaaagga    4140
cagtagaaaa ggaagatggc ttctacaaat gccatcattg cgataaagga aaggctatcg    4200
ttcaagatgc tctaccgac agtggtccca agatggacc cccacccacg aggaacatcg     4260
tggaaaaaga agacgttcca accacgtctt caaagcaagt ggattgatgt gatatctcca    4320
```

| | |
|---|---|
| ctgacgtaag ggatgacgca caatcccact atccttcgca agacccttcc tctatataag | 4380 |
| gaagttcatt tcatttggag aggacacgct gagttcacaa cacaaatcag atttatagag | 4440 |
| agatttataa aaaaaaaaaa acatgtgatc ccgggaattc gctagcacta gagtgtgatc | 4500 |
| ccgggaattc gctagcacta gagtcgcggc cgctttactt gtacagctcg tccatgccga | 4560 |
| gagtgatccc ggcggcggtc acgaactcca gcaggaccat gtgatcgcgc ttctcgttgg | 4620 |
| ggtctttgct cagggcggac tgggtgctca ggtagtggtt gtcgggcagc agcacggggc | 4680 |
| cgtcgccgat ggggatgttc tgctggtagt ggtcggcgag ctgcacgctg ccgtcctcga | 4740 |
| tgttgtggcg gatcttgaag ttcaccttga tgccgttctt ctgcttgtcg gccatgatat | 4800 |
| agacgttgtg gctgttgtag ttgtactcca gcttgtgccc caggatgttg ccgtcctcct | 4860 |
| tgaagtcgat gcccttcagc tcgatgcggt tcaccagggt gtcgccctcg aacttcacct | 4920 |
| cggcgcgggt cttgtagttg ccgtcgtcct tgaagaagat ggtgcgctcc tggacgtagc | 4980 |
| cttcgggcat ggcggacttg aagaagtcgt gctgcttcat gtggtcgggg ttgcggctga | 5040 |
| agcactgcac gccgtaggtc agggtggtca cgagggtggg ccaggcacg ggcagcttgc | 5100 |
| cggtggtgca gatgaacttc agggtcagct tgccgtaggt ggcatcgccc tcgccctcgc | 5160 |
| cggacacgct gaacttgtgg ccgtttacgt cgccgtccag ctcgaccagg atgggcacca | 5220 |
| ccccggtgaa cagctcctcg cccttgcacc atactagagt ccgcaaaaat caccagtctc | 5280 |
| tctctacaaa tctatctctc tcttttttc tccagaataa tgtgtgagta gttcccagat | 5340 |
| aagggaatta gggttcttat agggtttcgc tcatgtgttg agcatataag aaacccttag | 5400 |
| tatgtatttg tatttgtaaa atacttctat caataaaatt tctaattcct aaaaccaaaa | 5460 |
| tccagtgacc gggcggcggc tcgagaatga ttattttatg aatatatttc attgtgcaag | 5520 |
| tagatagaaa ttcatatatg tacataacac acgaaataaa caaaaaaga caatccaaaa | 5580 |
| acaaacaccc caaaaaaat aatcacttta gataaactcg tatgaggaga ggcacgttca | 5640 |
| gtgactcgac gattcccgag caaaaaaagt ctccccgtca cacatatagt gggtgacgca | 5700 |
| attatcttta aagtaatcct tctgttgact tgtcattgat aacatccagt cttcgtcagg | 5760 |
| attgcaaaga attatagaag ggatcccacc tttattttc ttcttttttc catatttagg | 5820 |
| gttgacagtg aaatcagact ggcaacctat taattgcttc cacaatggga cgaacttgaa | 5880 |
| ggggatgtcg tcgatgatat tataggtggc gtgttcatcg tagttggtga atcgatggt | 5940 |
| accgttccaa tagttgtgtc gtccgagact tctagcccag gtggtctttc cggtacgagt | 6000 |
| tggtccgcag atgtagaggc tggggtgtcg gattccattc cttccattgt cctggttaaa | 6060 |
| tcggccatcc attcaaggtc agattgagct tgttggtatg agacaggatg tatgtaagta | 6120 |
| taagcgtcta tgcttacatg gtatagatgg gtttccctcc aggagtgtag atcttcgtgg | 6180 |
| cagcgaagat ctgattctgt gaagggcgac acatacggtt caggttgtgg agggaataat | 6240 |
| ttgttggctg aatattccag ccattgaagt tttgttgccc attcatgagg gaattcttcc | 6300 |
| ttgatcatgt caagatattc ctccttagac gttgcagtct ggataatagt tctccatcgt | 6360 |
| gcgtcagatt tgcgaggaga gaccttatga tctcggaaat ctcctctggt tttaatatct | 6420 |
| ccgtcctttg atatgtaatc aaggacttgt ttagagtttc tagctggctg gatattaggg | 6480 |
| tgatttcctt caaaatcgaa aaagaagga tccctaatac aaggtttttt atcaagctgg | 6540 |
| agaagagcat gatagtgggt agtgccatct tgatgaagct cagaagcaac accaaggaag | 6600 |
| aaaataagaa aaggtgtgag tttctcccag agaaactgga ataaatcatc tctttgagat | 6660 |
| gagcacttgg gataggtaag gaaaacatat ttagattgga gtctgaagtt cttactagca | 6720 |

```
gaaggcatgt tgttgtgact ccgaggggtt gcctcaaact ctatcttata accggcgtgg    6780
aggcatggag gcagggtat tttggtcatt ttaatagata gtggaaaatg acgtggaatt    6840
tacttaaaga cgaagtcttt ggacaagggg gggcccacgc cgaatttaat attaccggcg    6900
tggccccccc ttatcgcgag tgctttagca cgagcggtcc agatttaaag tagaaaattt    6960
cccgcccact agggttaaag gtgttcacac tatacaagca tatacgatgt gatggtattg    7020
actagagttt aaactatcag tgtttgacag gatatattgg cgggtaaacc taagagaaaa    7080
gagcgtttat tagaataatc ggatatttaa aagggcgtga aaaggtttat ccgttcgtcc    7140
atttgtatgt gtacatcacc gacgagcaag gcaagaccga gcgcctttcc gacgctcacc    7200
gggctggttg ccctcgccgc tgggctggcg gccgtctatg gccctgcaaa cgcgccagaa    7260
acgccgtcga agccgtgtgc gagacaccgg ccgccggcgt tgtggatacc cgcggaaaa    7320 cttggccctc actgacagat gaggggcgga cgttgacact tgaggggccg actcacccgg    7380
cgcggcgttg acagatgagg ggcaggctcg atttcggccg gcgacgtgga gctggccagc    7440
ctcgcaaatc ggcgaaaacg cctgatttta cgcgagtttc ccacagatga tgtggacaag    7500
cctggggata agtgccctgc ggtattgaca cttgaggggc gcgactactg acagatgagg    7560
ggcgcgatcc ttgacacttg aggggcagag tgctgacaga tgaggggcgc acctattgac    7620
atttgagggg ctgtccacag gcagaaaatc cagcatttgc aagggtttcc gcccgttttt    7680
cggccaccgc taacctgtct tttaacctgc ttttaaacca atatttataa accttgtttt    7740
taaccagggc tgcgccctgt gcgcgtgacc gcgcacgccg aagggggtg ccccccttc    7800 tcgaaccctc ccggcccgct aacgcgggcc tcccatcccc caggggctg cgcccctcgg    7860 ccgcgaacgg cctcaccca aaatggcag cgctggcagt ccttgccatt gccgggatcg    7920
gggcagtaac gggatgggcg atcagcccga aagctacccc tatttgttta ttttttctaaa    7980 tacattcaaa tatgtatccg ctcatgagac aataaccctg ataaatgctt caataatatt    8040
gaaaaaggaa gagtatgagt attcaacatt tccgtgtcgc ccttattccc ttttttgcgg    8100
cattttgcct tcctgttttt gctcacccag aaacgctggt gaaagtaaaa gatgctgaag    8160
atcagttggg tgcacgagtg ggttacatcg aactggatct caacagcggt aagatccttg    8220
agagttttcg ccccgaagaa cgttttccaa tgatgagcac ttttaaagtt ctgctatgtg    8280
gcgcggtatt atcccgtatt gacgccgggc aagagcaact cggtcgccgc atacactatt    8340
ctcagaatga cttggttgag tactcaccag tcacagaaaa gcatcttacg gatggcatga    8400
cagtaagaga attatgcagt gctgccataa ccatgagtga taacactgcg gccaacttac    8460
ttctgacaac gatcggagga ccgaaggagc taaccgcttt tttgcacaac atgggggatc    8520
atgtaactcg ccttgatcgt tgggaaccgg agctgaatga agccatacca aacgacgagc    8580
gtgacaccac gatgcctgta gcaatggcaa caacgttgcg caaactatta actggcgaac    8640
tacttactct agcttcccgg caacaattaa tagactggat ggaggcggat aaagttgcag    8700
gaccacttct gcgctcggcc cttccggctg gctggtttat tgctgataaa tctggagccg    8760
gtgagcgtgg gtctcgcggt atcattgcag cactggggcc agatggtaag ccctcccgta    8820
tcgtagttat ctacacgacg gggagtcagg caactatgga tgaacgaaat agacagatcg    8880
ctgagatagg tgcctcactg attaagcatt ggtaactgtc agaccaagtt tactcatata    8940
tactttagat tgatttaaaa cttcattttt aatttaaaag gatctaggtg aagatccttt    9000
ttgataatct catgaccaaa atcccttaac gtgagttttc gttccactga gcgtcagacc    9060
```

```
ccgtagaaaa gatcaaagga tcttcttgag atccttttt tctgcgcgta atctgctgct    9120
tgcaaacaaa aaaaccaccg ctaccagcgg tggtttgttt gccggatcaa gagctaccaa    9180 ctcttttcc gaaggtaact ggcttcagca gagcgcagat accaaatact gttcttctag    9240
tgtagccgta gttaggccac cacttcaaga actctgtagc accgcctaca tacctcgctc    9300
tgctaatcct gttaccagtg gctgctgcca gtggcgataa gtcgtgtctt accgggttgg    9360
actcaagacg atagttaccg gataaggcgc agcggtcggg ctgaacgggg gttcgtgca    9420 cacagcccag cttggagcga acgacctaca ccgaactgag atacctacag cgtgagctat    9480
gagaaagcgc cacgcttccc gaagggagaa aggcggacag gtatccggta agcggcaggg    9540
tcggaacagg agagcgcacg agggagcttc caggggaaa cgcctggtat ctttatagtc    9600
ctgtcgggtt tcgccacctc tgacttgagc gtcgattttt gtgatgctcg tcagggggc    9660 ggagcctatg gaaaaacgcc agcaacgcgg ccttttttacg gttcctggcc ttttgctggc    9720
cttttgctca catggactct agctagagga tcacaggcag caacgctctg tcatcgttac    9780
aatcaacatg ctaccctccg cgagatcatc cgtgtttcaa accggcagc ttagttgccg    9840 ttcttccgaa tagcatcggt aacatgagca agtctgccg ccttacaacg gctctcccgc    9900
tgacgccgtc ccggactgat gggctgcctg tatcgagtgg tgattttgtg ccgagctgcc    9960
ggtcggggag ctgttggctg gctggtggca ggatatattg tggtgtaaac aaattgacgc   10020
ttagacaact taataacaca ttgcggacgt ttttaatgat cgaatactaa cgtctctacc   10080
acatt                                                               10085

<210> SEQ ID NO 17
<211> LENGTH: 10174
<212> TYPE: DNA
<213> ORGANISM: Artificial sequence
<220> FEATURE:
<223> OTHER INFORMATION: pRIC3 mLuc SV40ori

<400> SEQUENCE: 17
gaagagcgtg actccgaggg gttgcctcaa actctatctt ataaccggcg tggaggcatg      60
gaggcagggg tattttggtc attttaatag atagtggaaa atgacgtgga atttacttaa     120
agacgaagtc tttgcgacaa gggggggccc acgccgaatt taatattacc ggcgtggccc     180
ccccttatcg cgagtgcttt agcacgagcg gtccagattt aaagtagaaa atttcccgcc     240
cactagggtt aaaggtgttc acactataaa agcatatacg atgtgatggt atttggtcga     300
cacgcgtcac gtgagctttt tgcaaaagcc taggcctcca aaaaagcctc ctcactactt     360
ctggaatagc tcagaggcag aggcggcctc ggcctctgca taaataaaaa aaattagtca     420
gccatggggc ggagaatggg cggaactggg cggagttagg ggcgggatgg gcggagttag     480
gggcgggact atggttgctg actaattgag atgcttgctt tgcatacttc tgcctgctgg     540
ggagcctggg gactttccac acctggttgc tgactaattg agatgcttgc tttgcatact     600
tctgcctgcc tggggagcct ggggactttc cacaccgtcg acggatcctt atcgatttta     660 ccacattgt agaggtttta cttgcttta aaaacctccc cacctcccc ctgaacctga     720 aacataaaat gaatgcaatt gttgttgtta acttgtttat tgcagcttat aatggttaca     780
aataaagcaa tagcatcaca aatttcacaa ataaagcatt ttttcactg cattctagtt     840 gtggtttgtc caaactcatc aatgtatctt atcatgtctg ttaattaatt acacggcgat     900
cttttccgcc ttcttggcct ttatgaggat ctctctgatt tttcttgcgt cgagttttcc     960
ggtaagacct ttcggtactt cgtccacaaa cacaactcct ccgcgcaact ttttcgcggt    1020
```

```
tgttacttga ctggcgacgt aatccacgat ctcttttcc gtcatcgtct ttccgtgctc    1080
caaaacaaca acggcggcgg aagttcacc ggcgtcatcg tcgggaagac ctgcgacacc    1140
tgcgtcgaag atgttggggt gttggagcaa gatggattcc aattcagcgg gagccacctg    1200
atagcctttg tacttaatca gagacttcag gcggtcaacg atgaagaagt gttcgtcttc    1260
gtcccagtaa gctatgtctc cagaatgtag ccatccatcc ttgtcaatca aggcgttggt    1320
cgcttccgga ttgtttacat aaccggacat aatcatagga cctctcacac acagttcgcc    1380
tctttgatta acgcccagcg ttttcccggt atccagatcc acaaccttcg cttcaaaaaa    1440
tggaacaact ttaccgaccg cgcccggttt atcatccccc tcgggtgtaa tcagaatagc    1500
tgatgtagtc tcagtgagcc catatccttg cctgatacct ggcagatgga acctcttggc    1560
aaccgcttcc ccgacttcct tagagagggg agcgccacca gaagcaattt cgtgtaaatt    1620
agataaatcg tatttgtcaa tcagagtgct tttggcgaag aaggagaata gggttggcac    1680
cagcagcgca ctttgaatct tgtaatcctg aaggctcctc agaaacagct cttcttcaaa    1740
tctatacatt aagacgactc gaaatccaca tatcaaatat ccgagtgtag taaacattcc    1800
aaaaccgtga tggaatggaa caacacttaa aatcgcagta tccggaatga tttgattgcc    1860
aaaaatagga tctctggcat gcgagaatct cacgcaggca gttctatgag gcagagcgac    1920
acctttaggc agaccagtag atccagagga gttcatgatc agtgcaattg tcttgtccct    1980
atcgaaggac tctggcacaa aatcgtattc attaaaaccg ggaggtagat gagatgtgac    2040
gaacgtgtac atcgactgaa atccctggta atccgtttta gaatccatga taataatttt    2100
ttggatgatt gggagctttt tttgcacgtt caaaattttt tgcaaccoct ttttggaaac    2160 gaacaccacg gtaggctgcg aaatgcccat actgttgagc aattcacgtt cattataaat    2220
gtcgttcgcg ggcgcaactg caactccgat aaataacgcg cccaacaccg gcataaagaa    2280
ttgaagagag ttttcactgc atacgacgat tctgtgattt gtattcagcc catatcgttt    2340
catagcttct gccaaccgaa cggacatttc gaagtactca gcgtaagtga tgtccacctc    2400
gatatgtgca tctgtaaaag caattgttcc aggaaccagg gcgtatctct tcatagcctt    2460
atgcagttgc tctccagcgg ttccatcttc cagcggatag aatggcgccg ggccttttctt    2520 tatgttttg gcgtcttcca taagcttact tagatcgcag atccagcaca atggatctgg    2580
aggtcgaggg atctctagag aattcctcac gacacctgaa atggaagaaa aaactttga    2640 accactgtct gaggcttgag aatgaaccaa gatccaaact caaaaagggc aaattccaag    2700
gagaattaca tcaagtgcca agctggccta acttcagtct ccacccactc agtgtgggga    2760
aactccatcg cataaaaccc ctcccccaa cctaaagacg acgtactcca aaagctcgag    2820
aactaatcga ggtgcctgga cggcgcccgg tactccgtgg agtcacatga agcgacggct    2880
gaggacggaa aggcccttt cctttgtgtg ggtgactcac ccgcccgctc tcccgagcgc    2940
cgcgtcctcc attttgagct ccctgcagca gggccgggaa gcggccatct ttccgctcac    3000
gcaactggtg ccgaccgggc cagccttgcc gcccagggcg gggcgataca cggcggcgcg    3060
aggccaggca ccagagcagg ccggccagct tgagactacc cccgtccgat tctcggtggc    3120
cgcgctcgca ggccccgcct cgccgaacat gtgcgctggg acgcacgggc ccgtcgccg    3180 cccgcggccc caaaaaccga aataccagtg tgcagatctt ggcccgcatt tacaagacta    3240
tcttgccaga aaaaagcgt cgcagcaggt catcaaaaat tttaaatggc tagagactta    3300
tcgaaagcag cgagacaggc gcgaaggtgc caccagattc gcacgcggcg gccccagcgc    3360
```

```
ccaggccagg cctcaactca agcacgaggc gaagggctc cttaagcgca aggcctcgaa      3420
ctctcccacc cacttccaac ccgaagctcg ggatcaagaa tcacgtactg cagccaggtg      3480
gaagtaattc aaggcacgca agggccataa cccgtaaaga ggccaggccc gcgggaacca      3540
cacacggcac ttacctgtgt tctggcggca aacccgttgc gaaaaagaac gttcacggcg      3600
actactgcac ttatatacgg ttctccccca ccctcgggaa aaaggcggag ccagtacacg      3660
acatcacttt cccagtttac cccgcgccac cttctctagg caccggttca attgccgacc      3720 cctccccca acttctcggg gactgtgggc gatgtgcgct ctgcccactg acgggcaccg      3780
gagccaattc ccagtcgacc tggtccaaag accagagggc tattgagact tttcaacaaa      3840
gggtaatatc gggaaacctc ctcggattcc attgcccagc tatctgtcac ttcatcgaaa      3900
ggacagtaga aaaggaagat ggcttctaca atgccatca ttgcgataaa ggaaaggcta      3960
tcgttcaaga tgcctctacc gacagtggtc ccaaagatgg accccaccc acgaggaaca      4020 tcgtggaaaa agaagacgtt ccaaccacgt cttcaaagca agtggattga tgtgatacat      4080
ggtggagcac gacactctcg tctactccaa gaatatcaaa gatacagtct cagaagacca      4140
gagggctatt gagactttc aacaagggt aatatcggga aacctcctcg gattccattg      4200
cccagctatc tgtcacttca tcgaaaggac agtagaaaag gaagatggct tctacaaatg      4260
ccatcattgc gataaaggaa aggctatcgt tcaagatgcc tctaccgaca gtggtcccaa      4320
agatggaccc ccaccacga ggaacatcgt ggaaaagaa gacgttccaa ccacgtcttc      4380
aaagcaagtg gattgatgtg atatctccac tgacgtaagg gatgacgcac aatcccacta      4440
tccttcgcaa gacccttcct ctatataagg aagttcattt catttggaga ggacacgctg      4500
agttcacaac acaaatcaga tttatagaga gatttataaa aaaaaaaaa catgtgatcc      4560 cgggaattcg ctagcactag agtgtgatcc cgggaattcg ctagcactag agtcgcggcc      4620
gctttacttg tacagctcgt ccatgccgag agtgatcccg gcggcggtca cgaactccag      4680
caggaccatg tgatcgcgct tctcgttggg gtctttgctc agggcggact gggtgctcag      4740
gtagtggttg tcgggcagca gcacggggcc gtcgccgatg gggatgttct gctggtagtg      4800
gtcggcgagc tgcacgctgc cgtcctcgat gttgtggcgg atcttgaagt tcaccttgat      4860
gccgttcttc tgcttgtcgg ccatgatata gacgttgtgg ctgttgtagt tgtactccag      4920
cttgtgcccc aggatgttgc cgtcctcctt gaagtcgatg cccttcagct cgatgcggtt      4980
caccagggtg tcgccctcga acttcacctc ggcgcgggtc ttgtagttgc cgtcgtcctt      5040
gaagaagatg gtgcgctcct ggacgtagcc ttcgggcatg gcggacttga agaagtcgtg      5100
ctgcttcatg tggtcggggt gcggctgaa gcactgcacg ccgtaggtca gggtggtcac      5160
gagggtgggc cagggcacgg gcagcttgcc ggtggtgcag atgaacttca gggtcagctt      5220
gccgtaggtg gcatcgccct cgccctcgcc ggacacgctg aacttgtggc cgtttacgtc      5280
gccgtccagc tcgaccagga tgggcaccac cccggtgaac agctcctcgc ccttgcacca      5340
tactagagtc cgcaaaaatc accagtctct ctctacaaat ctatctctct ctatttttct      5400
ccagaataat gtgtgagtag ttcccagata agggaattag ggttcttata gggtttcgct      5460
catgtgttga gcatataaga aacccttagt atgtatttgt atttgtaaaa tacttctatc      5520
aataaatttt ctaattccta aaaccaaaat ccagtgaccg ggcggcggct cgagaatgat      5580
tattttatga atatatttca ttgtgcaagt agatagaaat tacatatgtt acataacaca      5640
cgaaataaac aaaaaaagac aatccaaaaa caaacacccc aaaaaaaata atcactttag      5700
ataaactcgt atgaggagag gcacgttcag tgactcgacg attcccgagc aaaaaaagtc      5760
```

```
tccccgtcac acatatagtg ggtgacgcaa ttatctttaa agtaatcctt ctgttgactt   5820
gtcattgata acatccagtc ttcgtcagga ttgcaaagaa ttatagaagg gatcccacct   5880
tttattttct tcttttttcc atatttaggg ttgacagtga aatcagactg gcaacctatt   5940
aattgcttcc acaatgggac gaacttgaag gggatgtcgt cgatgatatt ataggtggcg   6000
tgttcatcgt agttggtgaa atcgatggta ccgttccaat agttgtgtcg tccgagactt   6060
ctagcccagg tggtctttcc ggtacgagtt ggtccgcaga tgtagaggct ggggtgtcgg   6120
attccattcc ttccattgtc ctggttaaat cggccatcca ttcaaggtca gattgagctt   6180
gttggtatga gacaggatgt atgtaagtat aagcgtctat gcttacatgg tatagatggg   6240
tttccctcca ggagtgtaga tcttcgtggc agcgaagatc tgattctgtg aagggcgaca   6300
catacggttc aggttgtgga gggaataatt tgttggctga atattccagc cattgaagtt   6360
ttgttgccca ttcatgaggg aattcttcct tgatcatgtc aagatattcc tccttagacg   6420
ttgcagtctg gataatagtt ctccatcgtg cgtcagattt gcgaggagag accttatgat   6480
ctcggaaatc tcctctggtt ttaatatctc cgtcctttga tatgtaatca aggacttgtt   6540
tagagttcct agctggctgg atattagggt gatttccttc aaaatcgaaa aaagaaggat   6600
ccctaataca aggttttta tcaagctgga gaagagcatg atagtgggta gtgccatctt   6660
gatgaagctc agaagcaaca ccaaggaaga aaataagaaa aggtgtgagt ttctcccaga   6720
gaaactggaa taaatcatct ctttgagatg agcacttggg ataggtaagg aaaacatatt   6780
tagattggag tctgaagttc ttactagcag aaggcatgtt gttgtgactc cgaggggttg   6840
cctcaaactc tatcttataa ccggcgtgga ggcatggagg caggggtatt ttggtcattt   6900
taatagatag tggaaaatga cgtggaattt acttaaagac gaagtctttg gacaaggggg   6960
ggcccacgcc gaatttaata ttaccggcgt ggccccccct tatcgcgagt gctttagcac   7020
gagcggtcca gatttaaagt agaaaatttc ccgcccacta gggttaaagg tgttcacact   7080
atacaagcat atacgatgtg atggtattga ctagagttta aactatcagt gtttgacagg   7140
atatattggc gggtaaacct aagagaaaag agcgtttatt agaataatcg gatatttaaa   7200
agggcgtgaa aaggtttatc cgttcgtcca tttgtatgtg tacatcaccg acgagcaagg   7260
caagaccgag cgccttccg acgctcaccg ggctggttgc cctcgccgct gggctggcgg   7320
ccgtctatgg ccctgcaaac gcgccagaaa cgccgtcgaa gccgtgtgcg agacaccggc   7380
cgccggcgtt gtggatacct cgcggaaaac ttggccctca ctgacagatg aggggcggac   7440
gttgacactt gaggggccga ctcacccggc gcggcgttga cagatgaggg gcaggctcga   7500
tttcggccgg cgacgtggag ctggccagcc tcgcaaatcg gcgaaaacgc ctgattttac   7560
gcgagtttcc cacagatgat gtggacaagc ctggggataa gtgccctgcg gtattgacac   7620
ttgaggggcg cgactactga cagatgaggg gcgcgatcct tgacacttga ggggcagagt   7680
gctgacagat gaggggcgca cctattgaca tttgagggc tgtccacagg cagaaaatcc   7740
agcatttgca agggtttccg cccgttttc ggccaccgct aacctgtctt ttaacctgct   7800
tttaaaccaa tatttataaa ccttgttttt aaccagggct gcgccctgtg cgcgtgaccg   7860
cgcacgccga aggggggtgc ccccccttct cgaaccctcc cggcccgcta acgcgggcct   7920
cccatccccc caggggctgc gcccctcggc cgcgaacggc ctcaccccaa aaatggcagc   7980
gctggcagtc cttgccattg ccgggatcgg ggcagtaacg ggatgggcga tcagcccgaa   8040 agctaccct atttgtttat ttttctaaat acattcaaat atgtatccgc tcatgagaca   8100
```

```
ataaccctga taaatgcttc aataatattg aaaaaggaag agtatgagta ttcaacattt    8160
ccgtgtcgcc cttattccct tttttgcggc attttgcctt cctgtttttg ctcacccaga    8220
aacgctggtg aaagtaaaag atgctgaaga tcagttgggt gcacgagtgg gttacatcga    8280
actggatctc aacagcggta agatccttga gagttttcgc cccgaagaac gttttccaat    8340
gatgagcact tttaaagttc tgctatgtgg cgcggtatta tcccgtattg acgccgggca    8400
agagcaactc ggtcgccgca tacactattc tcagaatgac ttggttgagt actcaccagt    8460
cacagaaaag catcttacgg atggcatgac agtaagagaa ttatgcagtg ctgccataac    8520
catgagtgat aacactgcgg ccaacttact tctgacaacg atcggaggac cgaaggagct    8580
aaccgctttt ttgcacaaca tgggggatca tgtaactcgc cttgatcgtt gggaaccgga    8640
gctgaatgaa gccataccaa acgacgagcg tgacaccacg atgcctgtag caatggcaac    8700
aacgttgcgc aaactattaa ctggcgaact acttactcta gcttcccggc aacaattaat    8760
agactggatg gaggcggata agttgcagg accacttctg cgctcggccc ttccggctgg    8820
ctggtttatt gctgataaat ctggagccgg tgagcgtggg tctcgcggta tcattgcagc    8880
actggggcca gatggtaagc cctcccgtat cgtagttatc tacacgacgg ggagtcaggc    8940
aactatggat gaacgaaata cagatcgc tgagataggt gcctcactga ttaagcattg    9000
gtaactgtca gaccaagttt actcatatat actttagatt gatttaaaac ttcattttta    9060
atttaaaagg atctaggtga agatcctttt tgataatctc atgaccaaaa tcccttaacg    9120
tgagttttcg ttccactgag cgtcagaccc cgtagaaaag atcaaaggat cttcttgaga    9180 tcctttttt ctgcgcgtaa tctgctgctt gcaaacaaaa aaaccaccgc taccagcggt    9240
ggtttgtttg ccggatcaag agctaccaac tcttttccg aaggtaactg gcttcagcag    9300
agcgcagata ccaaatactg ttcttctagt gtagccgtag ttaggccacc acttcaagaa    9360
ctctgtagca ccgcctacat acctcgctct gctaatcctg ttaccagtgg ctgctgccag    9420
tggcgataag tcgtgtctta ccgggttgga ctcaagacga tagttaccgg ataaggcgca    9480
gcggtcgggc tgaacggggg gttcgtgcac acagcccagc ttggagcgaa cgacctacac    9540
cgaactgaga tacctacagc gtgagctatg agaaagcgcc acgcttcccg aagggagaaa    9600
ggcggacagg tatccggtaa gcggcagggt cggaacagga gagcgcacga gggagcttcc    9660
agggggaaac gcctggtatc tttatagtcc tgtcgggttt cgccacctct gacttgagcg    9720
tcgatttttg tgatgctcgt cagggggggcg gagcctatgg aaaaacgcca gcaacgcggc    9780 cttttacgg ttcctggcct tttgctggcc ttttgctcac atggactcta gctagaggat    9840
cacaggcagc aacgctctgt catcgttaca atcaacatgc taccctccgc gagatcatcc    9900
gtgtttcaaa cccggcagct tagttgccgt tcttccgaat agcatcggta acatgagcaa    9960
agtctgccgc cttacaacgg ctctcccgct gacgccgtcc cggactgatg ggctgcctgt   10020
atcgagtggt gattttgtgc cgagctgccg gtcggggagc tgttggctgg ctggtggcag   10080
gatatattgt ggtgtaaaca aattgacgct tagacaactt aataacacat tgcggacgtt   10140
tttaatgatc gaatactaac gtctctacca catt                              10174
```

<210> SEQ ID NO 18
<211> LENGTH: 255
<212> TYPE: DNA
<213> ORGANISM: Artificial sequence
<220> FEATURE:
<223> OTHER INFORMATION: SV40 origin of replication

<400> SEQUENCE: 18

```
cacgcgtcac gtgagctttt tgcaaaagcc taggcctcca aaaaagcctc ctcactactt        60
ctggaatagc tcagaggcag aggcggcctc ggcctctgca taaataaaaa aaattagtca       120
gccatggggc ggagaatggg cggaactggg cggagttagg ggcgggatgg gcggagttag       180
gggcgggact atggttgctg actaattgag atgcttgctt tgcatacttc tgcctgctgg       240
ggagcctggg gactt                                                       255
```

PLANT PRODUCED HUMAN PAPILLOMAVIRUS PSEUDOVIRION

CROSS-REFERENCE TO RELATED APPLICATIONS

This application is the National Stage entry under 35 U.S.C. § 371 of International Application No. PCT/IB2014/063411 filed on Jul. 25, 2014, published on Jan. 29, 2015 under publication number WO 2015/011676 A1, which claims the benefit of priority under 35 U.S.C. § 119 of South African Patent Application Number 2013/05650 filed Jul. 25, 2013.

BACKGROUND OF THE INVENTION

The present invention relates to a method of producing human papillomavirus (HPV) pseudovirions in plant cells, the plant produced pseudovirions per se, a neutralisation assay using the plant produced pseudovirions and pharmaceutical compositions comprising the plant produced pseudovirions.

The applicants have use novel autonomously replicating vectors in conjunction with previously developed, non-replicating vectors to produce HPV-16 pseudovirions (PsVs) in plants. Preliminary expression trials established optimal conditions and timeframes for production of each individual element required for assembly of HPV PsVs. The structural elements required for PsV production are HPV L1 and L2 proteins, produced by non-replicating plant expression vectors pTRAc-hL1 and pTRAc-hL2, respectively; and circular double-stranded DNA from one of three replicons derived from pRIC3-mSEAP, pRIC3-mSEAP+ or pRIC3-mluc+. Putative PsV particles, as well as L1/L2 virus-like particles (VLPs) produced in absence of the replicons, were harvested from plants and purified by successive gradient ultracentrifugation steps. Gradient fractions containing L1 were pooled and dialysed against high-salt (0.5M) NaCl PBS, to obtain purified PsVs. These were confirmed by electron microscopy to be conformationally similar to VLPs and PsVs produced in other systems, and by PCR to contain the corresponding encapsidated replicon DNA. Purified PsVs were used to demonstrate their use in a neutralisation assay. Two of the three PsVs created, namely mSEAP and mluc+ PsVs, demonstrated successful pseudoinfection and neutralisation with a common HPV16 neutralising antibody, while mSEAP+ PsVs showed no reporter gene expression after pseudoinfection of mammalian cells. This is the first known report of the production and purification of HPV PsVs, as well as L1/L2 VLPs in planta, as well as the first demonstration of a pseudovirion-based neutralisation assay (PBNA) using plant-produced PsVs.

Cervical cancers caused by high-risk HPV are the second most prevalent form of cancer in women in developing countries. Africa in particular has been identified as a high risk region for the disease. Recently developed L1 VLP vaccines, Cervarix® and Gardasil®, protect against HPV-16 and HPV-18, or HPV-6, HPV-11, HPV-16 and HPV-18 infection, respectively. Both currently available vaccines, Cervarix® and Gardasil®, elicit a strong and protracted neutralising antibody response, and have been shown to have sustained efficacy up to 5 years post-administration. While these vaccines have shown great promise in reducing the burden of disease, development and production of VLP vaccines remains prohibitively expensive, particularly in developing countries.

A key element of any HPV vaccine development initiative is the pseudovirion-based neutralisation assay (PBNA). Induction of neutralising antibodies is currently the best estimate of vaccine candidate efficacy for second generation HPV vaccine testing. Until recently, the identification of serum neutralising antibodies relied on the use of enzyme-linked immunosorbent assay (ELISA) or neutralisation assays using whole virus (Dessy et al., 2008). However, improvements in HPV PsV production efficiency in the last decade have allowed the development of the PBNA. Developed by John Schiller's group at the Center for Cancer Research, this assay uses mammalian cells for intracellular production of PsVs expressing a secreted alkaline phosphatase (SEAP) reporter gene (Buck et al., 2005a), and has since become the gold standard for testing neutralisation of candidate HPV vaccines, allowing rapid and un-biased screening of neutralising antibodies and epitopes (Stanley et al., 2008). While this production method has been shown to be extremely effective for production of PsVs, cell culture production is expensive, and SEAP assay kits are particularly expensive in comparison to other commonly used reporter assays such as luciferase or GFP. There is a need, therefore, to develop alternative PsV production methods to allow for affordable candidate vaccine development and, in particular, inexpensive testing of immune sera.

The production of neutralising IgG antibodies in response to vaccination has long been understood to be a key aspect of protective immunity (Robbins et al., 1995). It has been suggested that it may be possible to accurately estimate the required level of neutralising antibody required for protection, provided that the concentration, isotype and secondary biological activity of these antibodies could be accurately measured (Robbins et al., 1995). Neutralisation assays were developed as a method of accurately quantifying the neutralising capabilities of immune sera, usually in response to a live viral or vaccine candidate challenge, as well as identify neutralising epitopes (Ochsenbauer and Kappes, 2009; Yeager et al., 2000).

The first demonstration of in vitro neutralisation of papillomavirus was by Dvoretzky et al. (1980), who demonstrated neutralisation with rabbit-produced Bovine papillomavirus type 1 (BPV-1) antisera to confirm the role of BPV-1 in focus formation in mouse cell lines. Early efforts to establish a robust, sensitive in vitro neutralisation assay for HPVs were hampered by difficulties in production of infectious virus. Production of infectious virions in vitro was first achieved by grafting HPV-11-infected material into athymic mice—grafts were left to develop into condylomatous cysts over a period of 3-5 months, before being harvested and purified for HPV virions (Kreider et al., 1987). This method was utilised to produce virions for use in the first de facto neutralisation assay. Neutralising monoclonal antibodies were identified and isolated from HPV-11 or BPV-1 antisera. These antibodies were then used to demonstrate neutralisation of intact virions by ELISA, as well as identifying several neutralising conformational epitopes (Christensen et al., 1990). The same group used this method to successfully identify neutralising HPV antibodies in human sera for the first time, and further demonstrated that ELISA was a good indicator of the presence of neutralising antibodies in human sera (Christensen at al., 1992). Another approach coupled the neutralisation of HPV-11 infection with RT-PCR detection of HPV mRNA transcripts to create a semi-quantitative neutralisation assay (Smith et al., 1995). While these approaches were nominally successful in identification of neutralising antibodies, detection remained limited at best, and the procedures used were time-consuming and expensive.

A major step forward in neutralisation assay technology came with the advent of PsV production, which abrogated the need for the expensive and time-consuming xenograft production method. Roden at al. (1996) used hamster BPHE-1 cells to generate BPV-1 or HPV-16 PsVs. These were used to demonstrate focus formation in C127 cells, using the technique demonstrated by Dvoretzky et al. (1980). These researchers further showed that neutralising antibodies in HPV-16 antisera prevented focus formation, demonstrating a quantitative neutralisation assay of a high-risk HPV type using PsVs for the first time (Roden et al., 1996). In this report, the authors noted that the focus transformation assay required 2-3 weeks, and that inclusion of a marker or reporter gene would greatly improve the speed of the assay. This was first attempted by chemically linking a β-lactamase (BLAM) reporter plasmid to VLPs or infectious virions, and incubating these with PV antisera before infecting various mammalian cell lines. Early attempts demonstrated neutralisation, but resulted in <1% infection of cells with these PsVs (Muller at al., 1995). Yeager at al. (2000) and Bousarghin et al. (2002) demonstrated this approach more successfully, using a BLAM or luc reporter plasmids and an alternative method of attaching the plasmid to VLPs. More importantly, several groups generated PsVs with encapsidated reporter genes, and demonstrated their use for neutralisation assays (Buck et al., 2005a; Fleury et al., 2008; Kawana at al., 1998; Rossi at al., 2000; Stauffer at al., 1998; Touze and Coursaget, 1998; Unckell et al., 1997). While early attempts were inefficient due to poor PsV production levels, this was improved upon by intracellular generation of high yields of L1/L2 PsVs and Incorporation of a SEAP reporter plasmid (Buck at al., 2004). These PsVs were used with a commercially available SEAP detection kit to demonstrate a pseudovirion-based neutralisation assay that was at least as sensitive as, and potentially more type-specific than, the standard ELISA-based neutralisation assay (Pastrana et al., 2004).

While the system developed by Pastrana et al. (2004) is considered the current 'best practice' neutralisation assay, there remains room for improvement. In particular, the costs of PsV production could be greatly decreased by the use of a less expensive production system (Brondyk, 2009). Recombinant protein expression in plants has been demonstrated to have a significantly lower cost of production when compared to production in mammalian cells (Tiwari et al., 2009). As such, plant expression may provide an attractive alternative for the production of PsVs for use in the PBNA.

Expression of recombinant proteins in plants has developed over the last twenty years from a curiosity in the late 1980s to a medically and industrially relevant production system today. Early efforts relied on transformation of plants to produce stable transgenic lines. This was achieved through biolistic delivery or, more recently, agroinfiltration (Daniell et al., 2009). While transgenic protein production remains a useful and viable system, advances in transient expression methods and technology have positioned transient expression as the preferred method for industrial-scale production in plants (Rybicki, 2010). Two key factors that have played a central role in this transition are viral, or virus-derived, expression vectors, and the development of agroinfiltration technology.

Agroinfiltration was originally developed to as an alternative to biolistic bombardment for the stable transformation of plants (Kapila et al., 1997). This process relies on the DNA transfer capability of *A. tumefaciens* to introduce foreign DNA to plant cells. *A. tumefaciens* can be used to transfer a transgene located in the transfer DNA (T-DNA) segment of the Ti plasmid into plants infiltrated with a bacterial suspension of the transformed bacterium. The T-DNA is transported to the plant nucleus, and this allows for transformation of the plant through integration of the T-DNA into the plant genome (Zupan et al., 2000). Importantly, however, a transgene incorporated into the T-DNA may also be transiently expressed, from non-integrated or episomal T-DNA, resulting in systemic expression of a recombinant protein without the need for stable transformation (Kapila at al., 1997).

Viral vectors were the first transient expression method developed for plants. Early efforts simply inserted a recombinant gene or epitope into the genome of viruses such as TMV, cowpea mosaic virus (CPMV), or PVX, either fused to the viral coat protein or separately, under control of a duplicated subgenomic viral promoter (Durrani et al., 1998; Gleba et al., 2007; Turpen at al., 1995). While this application produced immunogenic protein, expression levels were lower than those found in transgenic plants. Other problems with these 'first-generation' viral vectors included a tendency to revert to the natural virus, constraints on insert size, difficulty of administration, and an inability to form VLPs (Kohl et al., 2006; Rybicki, 2010; Varsani at al., 2006).

These limitations prompted further work to develop 'second generation', or deconstructed, viral vectors. This approach used only the desirable viral elements, in particular the replicative machinery, to manufacture synthetic vectors capable of inducing transgene expression in plants. While these vectors are usually not infectious on their own, when coupled with agroinfiltration technology they can result in systemic transient expression of protein at levels comparable to that of transgenic plants (Tiwari at al., 2009). This approach has the advantages of short time frames (3-7 days) when compared to stable transformation (6-9 months), significant expression levels, and rapid and easy scale-up and purification. This makes agroinfiltration-mediated transient expression via viral vectors an ideal approach for the production of medically relevant proteins and particles in plants. Of particular interest is the use of transient expression for the production of VLPs and PsVs in plants, as there is potential for a reduction in cost when compared to traditional systems (Santi et al., 2006).

Papillomavirus L1 VLPs have been produced by several groups in plants. Most have used transgenic plants (Biemelt et al., 2003; Warzecha at al., 2003) with resulting low yields. Early attempts at transient expression of L1 also yielded low levels of expression, as well as an apparent inability to form VLPs (Varsani et al., 2006). However, agroinfiltration of an *Agrobacterium* vector coding for a human codon-optimised L1 protein provided a much higher protein yield, and demonstrated that transient expression of HPV-16 VLPs at high levels is a feasible approach for the production of immunogenic HPV candidate vaccines (Maclean et al., 2007).

The vector used to produce L1 at such high expression levels—pTRAc—was developed at the Fraunhofer Institute for Molecular Biology and Applied Biology. This vector utilises a CaMV 35S promoter with duplicated transcriptional enhancer, chalcone synthase 5'-untranslated region, and CaMV 35S polyadenylation signal for foreign gene expression. This vector has also been used to express minor capsid protein L2 in plants (Pereira, 2008). However, coexpression of L1 and L2 has not previously been conclusively demonstrated to form VLPs in planta.

A further development in vector technology has been the use of single-stranded DNA plant geminiviruses in the genus Mastrevirus, family Geminiviridae, to create replicating vectors. These replicating vectors incorporate a viral Ori (origin of replication) sequence that is duplicated on either side of a gene expression cassette. The replicating vectors further may or may not include a viral replication-associated protein (Rep) gene. Agroinfiltration of a single Rep-containing replicon construct, or of a replicon construct plus a Rep construct expressed in trans by standard techniques, results in release of a plasmid-like "replicon" which multiplies under the control of Rep protein up to copy numbers of several thousand per cell (Regnard et al., 2010). This can result in significantly increased expression of genes of interest compared to non-replicating vector expression. While the expression of a geminivirus Rep gene and cognate (eg: Ori sequence from the same virus) replicon construct in a plant cell leads to replication of the replicon, this is not known to occur in mammalian cells.

Encapsidation or covalent attachment of DNA by HPV VLPs to form PsVs has been demonstrated in yeast, insect, bacterial and mammalian cell systems (Buck at al., 2005a; Roden et al., 1996; Rossi et al., 2000; Unckell et al., 1997). Buck et al. (2005a) demonstrated that intracellular encapsidation of the pseudogenome is more efficient than in vitro disassembly-reassembly methods for the production of HPV PsVs, probably due to cellular factors that assist in correct assembly of the virions (Buck et al., 2008; Fleury et al., 2008; Peng et al., 2011). Currently, HPV pseudovirions have not been successfully expressed in plant expression systems. As discussed above, transient expression in plants offers several significant advantages for this application: protein expression in plants has been shown to be safe, cheaper than other expression systems, and potentially extremely rapid (Ma at al., 2005; Schillberg et al., 2005). A further significant advantage is that there is no need for downstream processing of proteins (e.g. glycosylation), as for bacterial recombinant protein expression systems (Giorgi et al., 2010). While it has been noted that N-glycosylation may differ in plants (specifically, plants cannot synthesise β-1,4-galactose and sialic acid), this problem can be overcome by recent advances in transgenic tobacco to provide 'humanised' glycosylation machinery (Bakker et al., 2006; Gleba et al., 2007). Further, it has been suggested that glycosylated L1 or L2 are not an important part of the assembled virion (Zhou et al., 1993).

In this application the inventors evaluated the feasibility of expressing HPV L1/L2 pseudovirions with an encapsidated mammalian reporter cassette, derived from a replicating geminivirus-derived vector, in planta. To achieve this, pTRAc plasmids expressing L1 and L2 proteins were co-infiltrated into plants with novel autonomously replicating plasmids, developed in this study, to create HPV L1/L2 PsVs. Further, we purified these particles by density-based centrifugation, for subsequent testing in a mammalian system.

This invention describes, for the first time, the successful production of HPV PsVs in plants, and testing of the PsVs in a standard PBNA. HPV L1/L2 VLPs, as well as PsVs containing a mammalian reporter cassette pseudogenome derived from the geminivirus Bean yellow dwarf virus (BeYDV), were produced in large quantities in planta. The particles readily encapsidated the pseudogenome DNA provided by the replicating vectors. Further, they were easily purified, stable at high temperature, and were conformationally indistinguishable from PsVs produced in other systems. Most importantly, they were successfully used to perform a PBNA in mammalian cells. Transient plant-based production of HPV PsVs is a feasible strategy, and should be further investigated as a low-cost alternative to mammalian cell culture for PsV production.

SUMMARY OF THE INVENTION

The present invention provides pseudovirions produced in plant cells, methods for producing the pseudovirions in plants, a neutralisation assay using the plant produced pseudovirions and pharmaceutical compositions comprising the plant produced pseudovirions.

The present invention teaches that transient co-expression of HPV L1 and HPV L2 in a plant cell together with concurrent replication, to high copy number, of a ssDNA virus-derived replicon containing a gene encoding a heterologous polypeptide of interest, results in the HPV L1 and HPV L2 assembling into virus-like particles encapsidating the replicon to form pseudovirions. Further, the pseudovirions and method for producing them described in this invention provide a significant advancement for the potential production of vaccines and DNA delivery vehicles for use in gene therapy.

According to a first aspect of the invention there is provided for a method for producing a human papillomavirus (HPV) pseudovirion in a plant cell. The method comprises a step of introducing into the plant cell a first nucleic acid encoding a HPV L1 polypeptide and a second nucleic acid encoding a HPV L2 polypeptide, wherein the first and second nucleic acids are contained on at least one expression vector. The method further comprises a step of introducing a replicating vector comprising a third nucleic acid encoding a heterologous polypeptide into the plant cell. The HPV L1 polypeptide and HPV L2 polypeptide are consequently expressed in the plant cell, and the replicating vector is replicated, in order to produce a high copy number of the replicating vector in the plant cell. The expressed HPV L1 and HPV L2 polypeptides subsequently assemble, together with a copy of the replicating vector, and encapsidate the replicating vector to produce a HPV pseudovirion.

It will be appreciated that the first and second nucleic acids are operably linked to regulatory sequences that allow for expression of the HPV L1 and HPV L2 polypeptides.

In one embodiment of the invention replication of the replicating vector is initiated by a regulatory protein. It will be appreciated that the regulatory protein will be encoded by a fourth nucleic acid which is operably linked to regulatory sequences, which allows for the expression of the regulatory protein. It will further be appreciated that the fourth nucleic acid may be expressed from either (i) a nucleic acid sequence contained on the replicating vector, (ii) a nucleic acid sequence contained on the at least one expression vector, (ill) a nucleic acid sequence contained on an independent vector, not being the vector of (i) or (ii) above; or (iv) a nucleic acid sequence integrated into the genomic DNA of the plant cell. Preferably, expression of the regulatory protein in the presence of the replicating vector initiates replication of the replicating vector.

In another embodiment of the invention it will be appreciated that the third nucleic acid sequence is operably linked to a regulatory sequence which allows for expression of the heterologous polypeptide in a mammalian cell.

In a preferred embodiment of the invention the third nucleic acid encoding the heterologous polypeptide, comprises a gene selected from the group consisting of a reporter gene, a therapeutic gene or a gene encoding an antigenic polypeptide, such as a gene encoding HPV E6 or E7 oncoprotein-derived constructs for treating cervical lesions or carcinomas caused by HPVs. Preferably, the gene encoding the heterologous polypeptide is a reporter gene selected from a luciferase gene or a secreted alkaline phosphatase gene.

In a further embodiment of the invention the polynucleotides encoding the HPV L1 and HPV L2 polypeptides are from HPV 16. It will however be appreciated by a person skilled in the art that the present invention will work just as effectively for a HPV type for which virus like particles can be produced, including but not limited to HPV 6, HPV 11, HPV 18, HPV 31, HPV 33, HPV 45, HPV 48, HPV 52, and/or HPV 58, or combinations thereof.

In yet another embodiment of the invention the method comprises a step of recovering the HPV pseudovirion from the plant cell.

According to a second aspect of the invention, there is provided for an assay for detecting the presence of a neutralising antibody to HPV in a subject. The assay including the steps of producing a first sample by combining the HPV pseudovirion produced according to the method above, with a biological sample from the subject to form a biological sample composition, wherein the heterologous polypeptide is a reporter polypeptide. Producing a second sample by combining the HPV pseudovirion produced according to the method above, with a control sample, wherein the control sample does not contain a HPV neutralising antibody, in order to form a control sample composition, wherein the heterologous polypeptide is a reporter polypeptide. The assay further comprising the step of contacting and incubating a mammalian cell capable of being infected with HPV with the first (biological) sample composition or with the second (control) sample composition and thereafter assaying the expression of the reporter polypeptide, wherein a decreased expression of the reporter polypeptide in the mammalian cells contacted with the first sample composition, as compared to mammalian cells contacted with the second sample composition is indicative of the presence of a HPV neutralising antibody in the biological sample.

Preferably, the reporter polypeptide used in the assay is selected from either a luciferase (luc) or a secreted alkaline phosphatase (SEAP) polypeptide.

More preferably, the assay is performed on a biological sample from a human subject.

A third aspect of the invention provides for a HPV pseudovirion comprising a capsid, wherein the capsid comprises a HPV L1 and a HPV L2 polypeptide, wherein the capsid encapsidates a replicating vector that encodes a heterologous polypeptide. Wherein, the heterologous polypeptide is operably linked to a regulatory sequence that allows for its expression in a mammalian cell, and further, wherein the HPV pseudovirion is produced in and recovered from a plant cell.

In a preferred embodiment of the invention replication of the replicating vector is initiated, in a mammalian cell infected by the HPV pseudovirion, in the presence of a regulatory protein. Preferably, the regulatory protein is encoded by a nucleic acid sequence operably linked to a regulatory sequence that allows for the expression of the regulatory protein in the mammalian cell. It will be appreciated by those skilled in the art that the regulatory protein may be expressed from a nucleic acid sequence contained on the replicating vector, a nucleic acid sequence contained on an independent vector; or from a nucleic acid sequence integrated into the genomic DNA of the mammalian cell. It will further be appreciated that expression of the regulatory protein in the mammalian cell in the presence of the replicating vector will result in the replication of the replicating vector.

Preferably, the heterologous polypeptide of this embodiment of the invention is selected from the group consisting of a reporter polypeptide, a therapeutic polypeptide or an antigenic polypeptide, such as a gene encoding HPV E6 or E7 oncoprotein-derived constructs for treating cervical lesions or carcinomas caused by HPVs.

According to a fourth aspect of the present invention there is provided for a pharmaceutical composition comprising a human papillomavirus pseudovirion produced by the method described above or containing the human papillomavirus pseudovirion described above and a pharmaceutically acceptable carrier or adjuvant. It will be appreciated that the pharmaceutical composition may be a vaccine composition or a DNA delivery vehicle.

BRIEF DESCRIPTION OF THE FIGURES

Non-limiting embodiments of the invention will now be described by way of example only and with reference to the following figures:

FIG. 16: mSEAP mammalian expression cassette (SEQ ID NO: 8).

FIG. 17: mSEAP+ cassette: expression cassette comprising a SEAP mammalian cassette and EGFP plant cassette (SEQ ID NO: 9).

FIG. 18: mluc+ cassette: expression cassette comprising a mluc mammalian cassette and EGFP plant cassette (SEQ ID NO: 10).

DETAILED DESCRIPTION OF THE INVENTION

Figure 1:
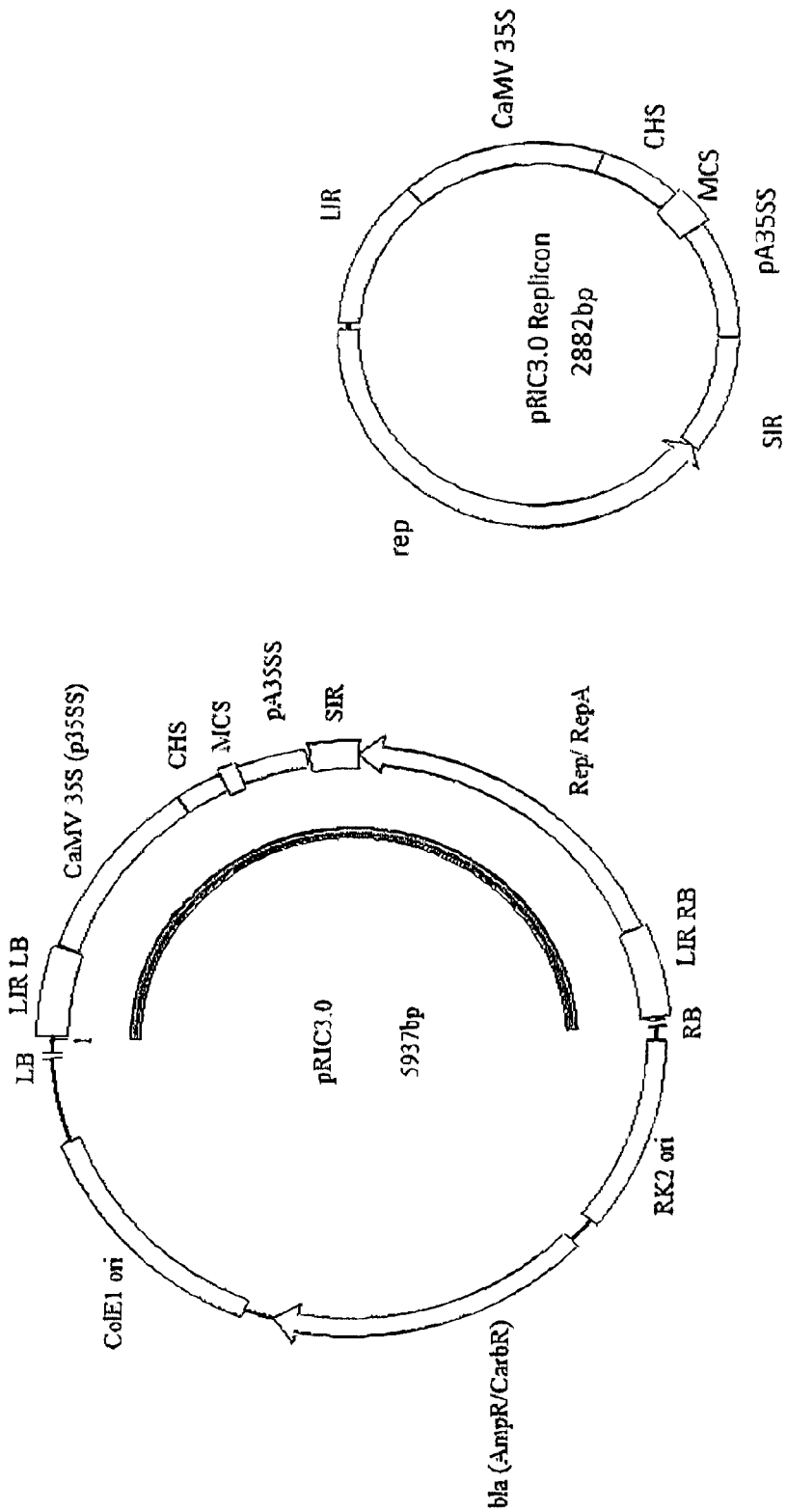
FIG. 1: 2nd generation vector pRIC3 and replicon. ColE1 ori, origin of replication for *Escherichia coli*; RK2 ori, origin of replication for *Agrobacterium tumefaciens*; bla, ampicillin/carbenicillin resistance bla gene; LB and RB, left and right borders for T-DNA integration; P35SS, CaMV 35S promoter with duplicated transcriptional enhancer; CHS, chalcone synthase 5'-untranslated region; MCS, multiple cloning site, pA35S, CaMV 35S polyadenylation signal; LIR, BeYDV long intergenic region; SIR, BeYDV short intergenic region; rep, BeYDV rep gene. The curved bar inside the plasmid maps indicates the T-DNA transferred into the plant cell during transfection.

The present invention will now be described more fully hereinafter with reference to the accompanying drawings, in which some, but not all embodiments of the invention are shown.

The invention as described should not to be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

Provided herein is a method for producing a human papillomavirus (HPV) pseudovirion in a plant cell. "Papillomaviruses" are DNA viruses from the family Papillomaviridae that infect the skin and mucous membranes of animals, preferably mammals, and even more preferably humans. A "VLP" or "virus-like particle" refers to the capsid-like structure which results from the assembly of the HPV L1 protein alone, or with the HPV L2 capsid protein. These structures are antigenically and morphologically similar to actual HPV virus particles or virions. Virus-like particles do not include viral genetic material; accordingly, these particles are not infectious.

The term "pseudovirion" or "PsV" refers to a papillomavirus virus-like particle including the papillomavirus capsid proteins in which a plasmid or vector containing a heterologous gene of interest has been encapsidated. The pseudovirions of the invention contain non-native genetic material which can be transferred by the virus to an animal cell, preferably a mammalian cell, and most preferably to a human cell. The non-native genetic material may include a plasmid encoding a therapeutic gene, reporter gene, a gene encoding an antigenic polypeptide, such as a gene encoding HPV E6 or E7 oncoprotein-derived constructs for treating cervical lesions or carcinomas caused by HPVs, and/or any other heterologous gene of interest under the control of a mammalian promoter, which can be delivered to a mammalian cell by the pseudovirion. In this specification "encapsidated" refers to the plasmid or vector being enclosed within the capsid of the virus-like particle.

The term "protein" should be read to include "peptide" and "polypeptide" and vice versa.

The method of the invention includes the steps of introducing a first polynucleotide encoding an HPV L1 polypeptide and a second polynucleotide encoding an HPV L2 polypeptide into a plant cell. It will be appreciated that the first and second polynucleotides may be contained on either a single or on two vectors.

The term "vector" refers to some means by which polynucleotides or gene sequences can be introduced into a cell. There are various types of vectors known in the art including plasmids, viruses, bacteriophages and cosmids. Generally polynucleotides or gene sequences are introduced into a vector by means of a cassette. The term "cassette" refers to a polynucleotide or gene sequence that is expressed from a vector, for example, the polynucleotide or gene sequences encoding the HPV L1 and HPV L2 proteins. A cassette generally comprises a gene sequence inserted into a vector, which in some embodiments, provides regulatory sequences for expressing the polynucleotide or gene sequences. In other embodiments, the polynucleotide or gene sequence provides the regulatory sequences for its expression. In further embodiments, the vector provides some regulatory sequences and the nucleotide or gene sequence provides other regulatory sequences. "Regulatory sequences" include but are not limited to promoters, transcription termination sequences, enhancers, splice acceptors, donor sequences, Introns, ribosome binding sequences, poly(A) addition sequences, and/or origins of replication.

The method further includes the step of introducing a third polynucleotide sequence into a plant cell. The third polynucleotide sequence is in the form of a replicon which is contained within a larger vector. The replicon itself contains a polynucleotide encoding a heterologous polypeptide of interest. In order for amplification of the replicon encoding the heterologous polypeptide of interest to proceed, replicational release of the replicon from the larger vector must occur in a plant cell. Once it is released from the larger vector the replicon, together with an expression cassette comprising a polynucleotide or gene sequence encoding the heterologous polypeptide of interest, is further replicated to high copy number in the plant cell. Due to structural elements in its polynucleotide make up the replicon that is released from the larger vector recircularises to form a smaller plasmid containing the polynucleotide or gene sequence encoding the heterologous polypeptide of interest.

The co-expression of the HPV L1 and HPV L2 polypeptides in the plant cell results in the L1 and L2 polypeptides self-assembling into virus-like particles in the cell. As a result of the high copy number of the replicon in the cell copies of the replicon are encapsidated directly into the virus-like particles during assembly in the cell to form pseudovirions. This is in contrast to indirect methods of incorporating a polynucleotide of interest into a pseudovirion by chemically or mechanically separating the virus-like particles and introducing a polynucleotide of interest into the virus-like particle to form a pseudovirion.

The replicating vector is held to be incapable of replicating in a mammalian cell, this is due to the fact that while the plant virus-derived Rep protein may be capable of initiating replication of the replicon in an animal cell, preferably a mammalian cell, and most preferably to a human cell, in the vector system described the Rep protein is expressed from a plant-specific promoter sequence which is highly unlikely to be recognised in a mammalian cell. On the other hand, the gene encoding the heterologous polypeptide is, however, capable of being expressed in a mammalian cell because it is under the control of a well-characterised mammalian promoter as part of the expression cassette.

It will be appreciated by a person skilled in the art that the gene encoding the Rep protein may be contained on the replicating vector, on another vector (such as a vector containing a cassette encoding the HPV L1 and/or HPV L2 polypeptide), it may further be integrated into the DNA of the plant cell in which the pseudovirions are produced, or it may be integrated, together with a suitable promoter, into the DNA of a mammalian cell into which the carrier vector is introduced by the pseudovirion. The presence of the Rep protein in the plant or mammalian cell may result in the initiation of replication of the replicating vector and production of the replicon to high copy number.

The gene encoding the heterologous polypeptide contained on the replicon may include a gene selected from the group consisting of a reporter gene, a therapeutic gene and possibly other genes related to desirable human or animal vaccine proteins—such as HPV L1 or L2, HIV Gag or Env, and others.

It will be appreciated that a "reporter gene" may be selected from any nucleic acid encoding a polypeptide or protein whose transcription, translation and/or post-translation activity can be detected. Examples of reporter genes include genes for luciferase, secreted alkaline phosphatase, green fluorescent protein, beta-galactosidase, and the like. The expression of the reporter polypeptide is used in the present invention as an indicator of the presence of neutralising antibodies to HPV in a sample. The pseudovirions of the invention can thus be used in a neutralisation assay for detection of neutralising antibodies to HPV in a subject.

It will also be appreciated that the replicon may be derived from any single-stranded DNA virus of plants, including geminiviruses and nanoviruses, as well as from bird and mammalian circoviruses, or from parvoviruses, and/or bacterial ssDNA viruses or bacterial plasmids that replicate via a similar rolling circle DNA replication strategy. All that is required is a Rep protein or equivalent, expressed in the presence of a DNA construct carried in a larger plasmid, which incorporates at least one origin of replication sequence (Ori) recognised by the Rep so as to allow the initiation of rolling circle replication.

The pseudovirion neutralisation assay of the invention could be used for the development of a HPV pseudovirus neutralisation kit which could be used to test the effectiveness of potential HPV vaccine candidates.

The delivery of the replicon from the pseudovirion to a mammalian cell is a clear indicator that the pseudovirions of the invention are capable of being used as DNA delivery vehicles for the purposes of gene therapy.

Production of the pseudovirions of the invention in plants has certain benefits over the current mammalian cell production methods. Among others the cost of production of plant derived pseudovirions is substantially lower than the cost of production in mammalian cells. Currently, pseudovirions are only produced in mammalian cancer-derived cultured cells: this production method poses certain safety issues in that the pseudovirions could encapsidate oncogenes from the cell lines. This could result in a subject who is treated with these pseudovirions being "infected" with cancer-causing genes. Further, propagation of pseudovirions in mammalian cell lines could result in other viruses and/or contaminants being encapsidated in the capsid.

The method of production of the pseudovirions of the invention in plants is a simple process and removes the possibility of oncogene or mammalian virus contamination. The process is also highly scalable. Further, should plant virus-derived replicating DNA be encapsidated into the pseudovirions of the invention this plant virus-derived DNA will not be capable of replicating in mammalian cells or of combining with other mammalian viruses or transposon like sequences.

The following examples are now offered by way of Illustration and not by way of limitation of the invention described herein.

Example 1

Repilcon Production in Plants

Plant Expression Vectors

Figure 2:
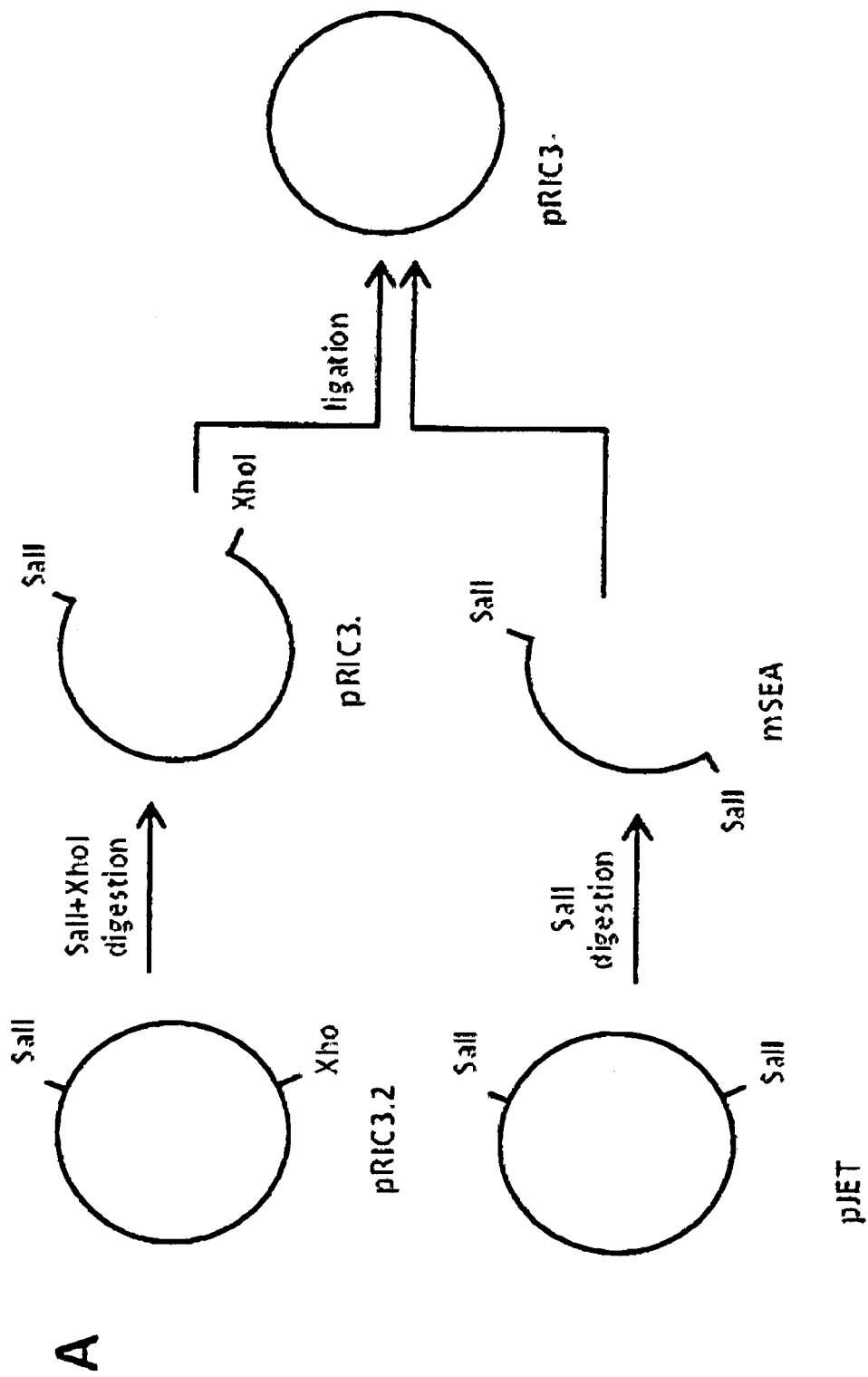
FIG. 2: Construction of pRIC3-mSEAP and replicon. Autonomously replicating plasmid pRIC3-mSEAP. (A) Final cloning steps to create pRIC3-mSEAP. (B) EF-1α, elongation factor 1 alpha promoter; SEAP, Secreted Alkaline Phosphatase gene; SV40 PolyA, simian virus 40 polyadenylation signal. The curved bar inside plasmid map indicates T-DNA transfected into plant cells. (C) Circularised replicon after release from T-DNA.
Figure 2:
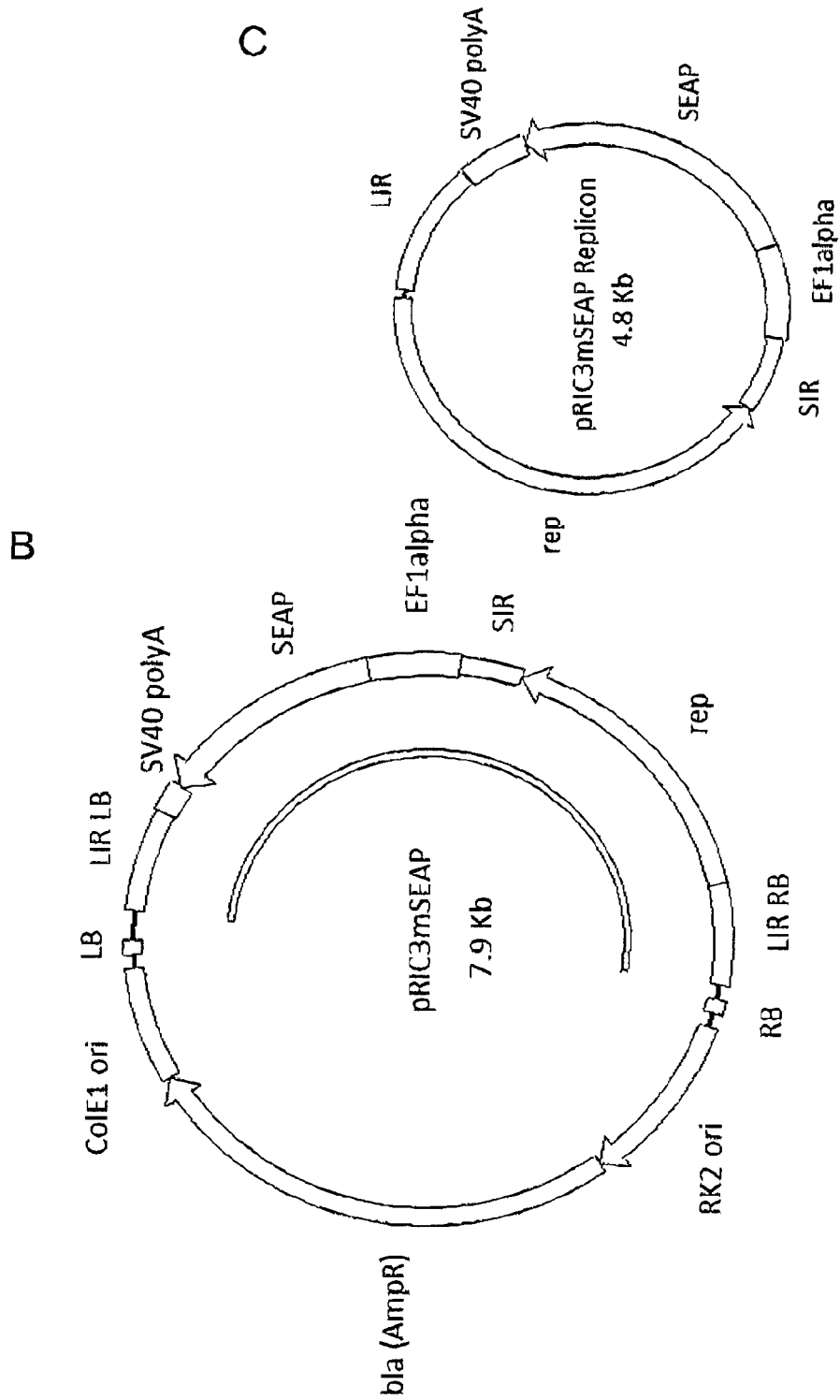
Figure 3:
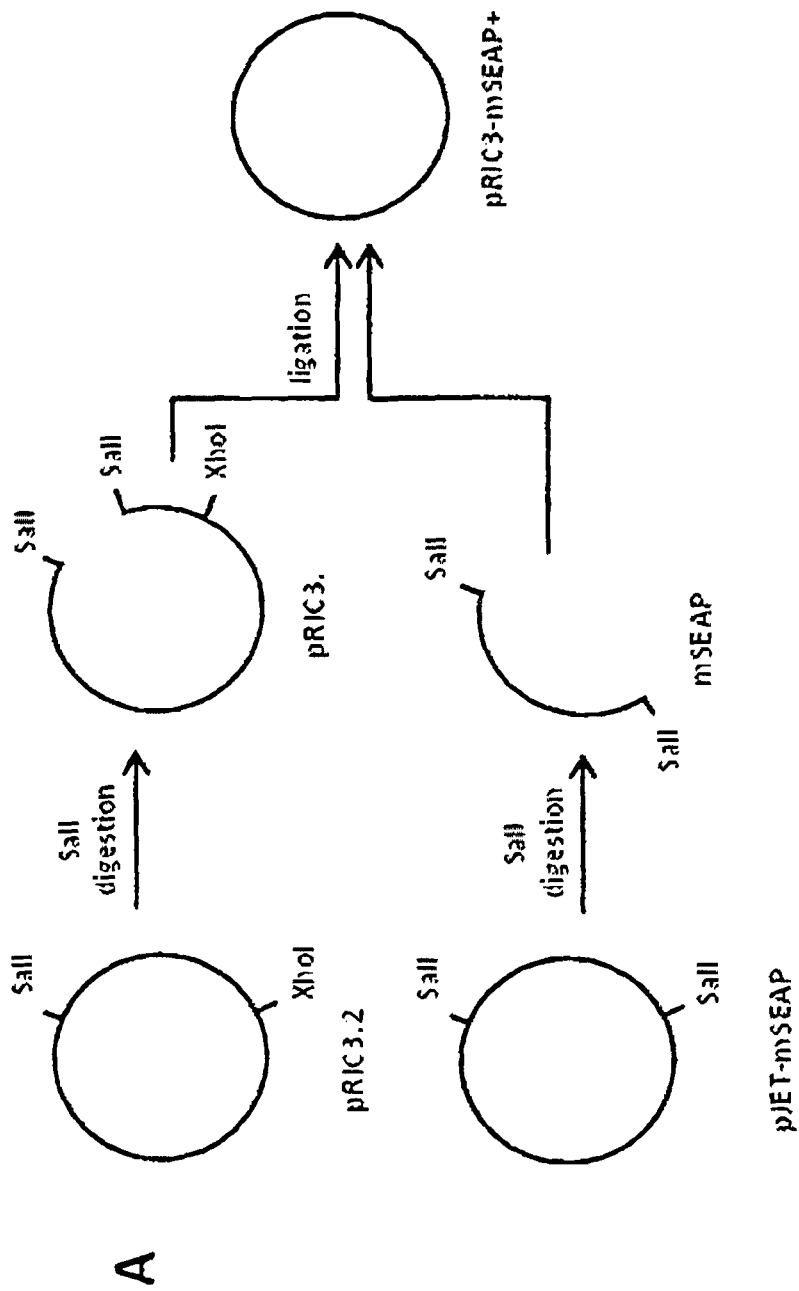
FIG. 3: Construction of pRIC3-mSEAP+ and replicon. pRIC3-mSEAP+ autonomously replicating plasmid. (A) Final cloning steps in construction of pRIC3-mSEAP+. (B) EF-1α, elongation factor 1 alpha promoter; SEAP, Secreted Alkaline Phosphatase gene; SV40 PolyA, simian virus 40 polyadenylation signal; CaMV 35S, cauliflower mosaic virus promoter region, EGFP, enhanced green fluorescent protein gene; pA35SS, CaMV 35S polyadenylation signal. The curved bar inside plasmid map indicates T-DNA transfected into plant cells. (C) Circularised replicon after release from T-DNA.
Figure 3:
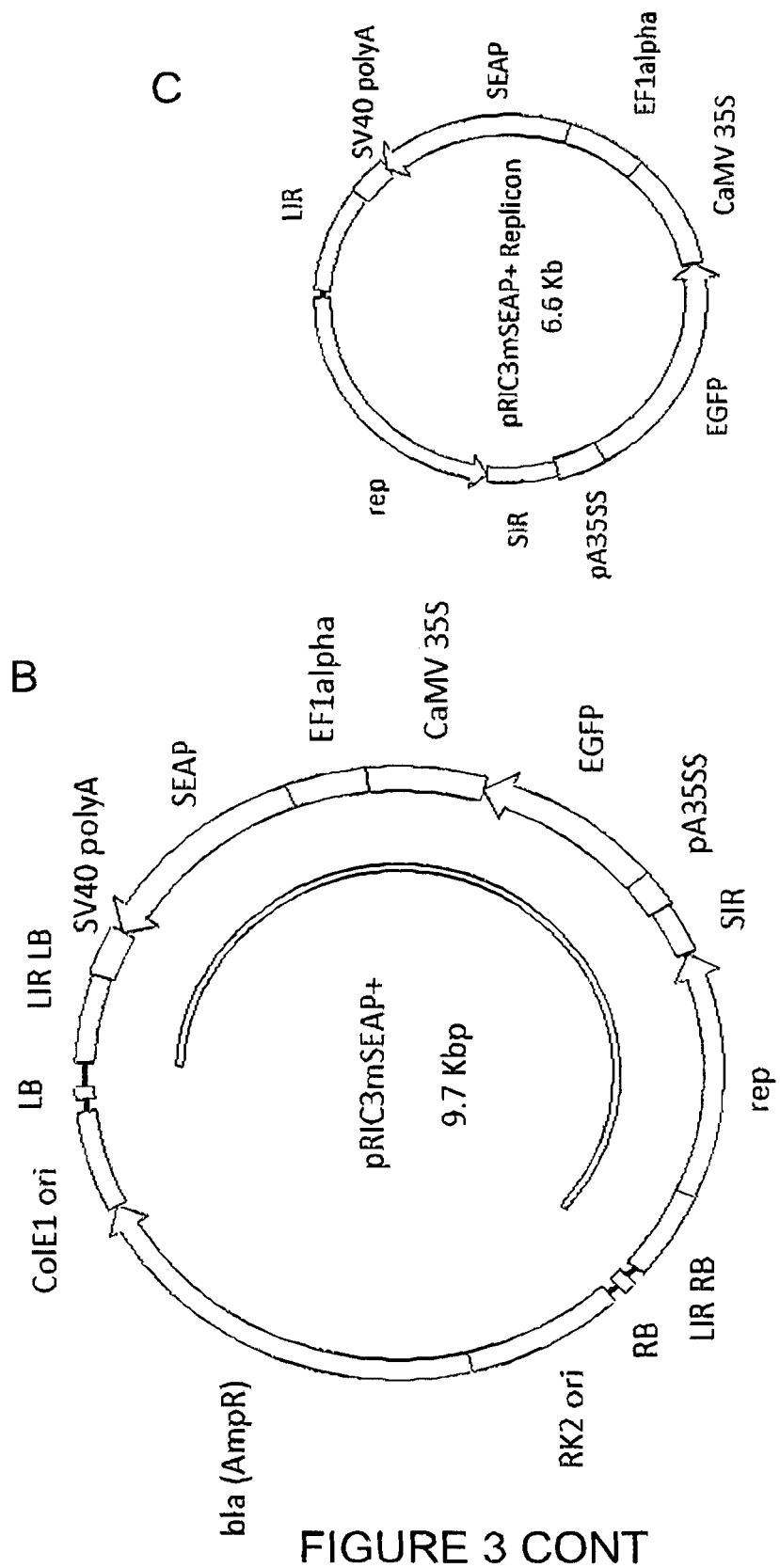
Figure 4:
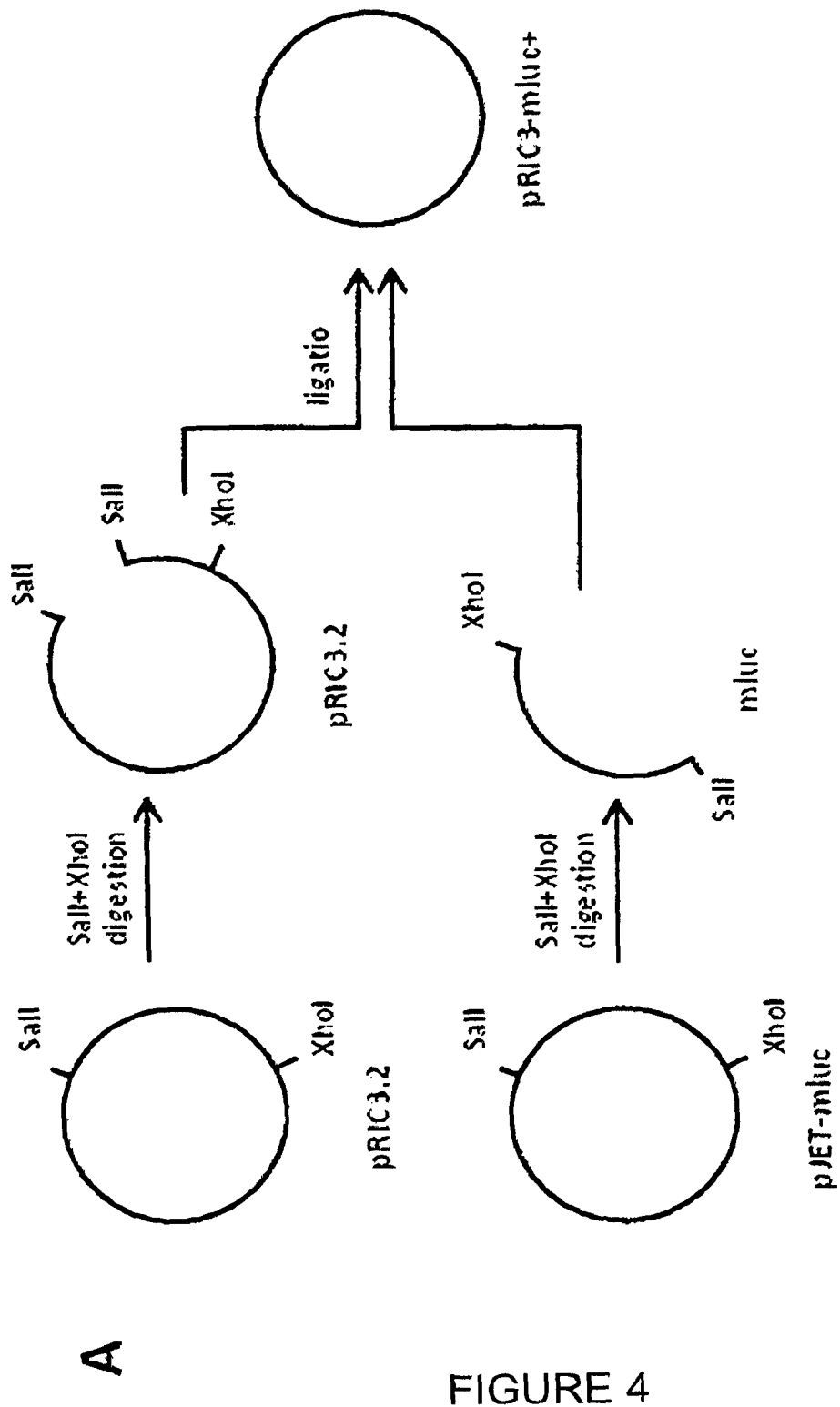
FIG. 4: Construction of pRIC3-mluc+ and replicon. Autonomously replicating plasmid pRIC3-mluc+. (A) Final cloning steps to create pRIC3-mluc+. (B)CMV I/E/P+ pCapR, cytomegalovirus intron/enhancer/promoter region with pCapR enhancer; luc, firefly luciferase reporter gene; BGH polyA, bovine growth hormone polyadenylation signal. CaMV 35S, cauliflower mosaic virus promoter region, EGFP, enhanced green fluorescent protein; pA35SS, CaMV 35S polyadenylation signal. The curved bar inside plasmid map indicates T-DNA transfected into plant cells. (C) Circularised replicon after release from T-DNA.
Figure 4:
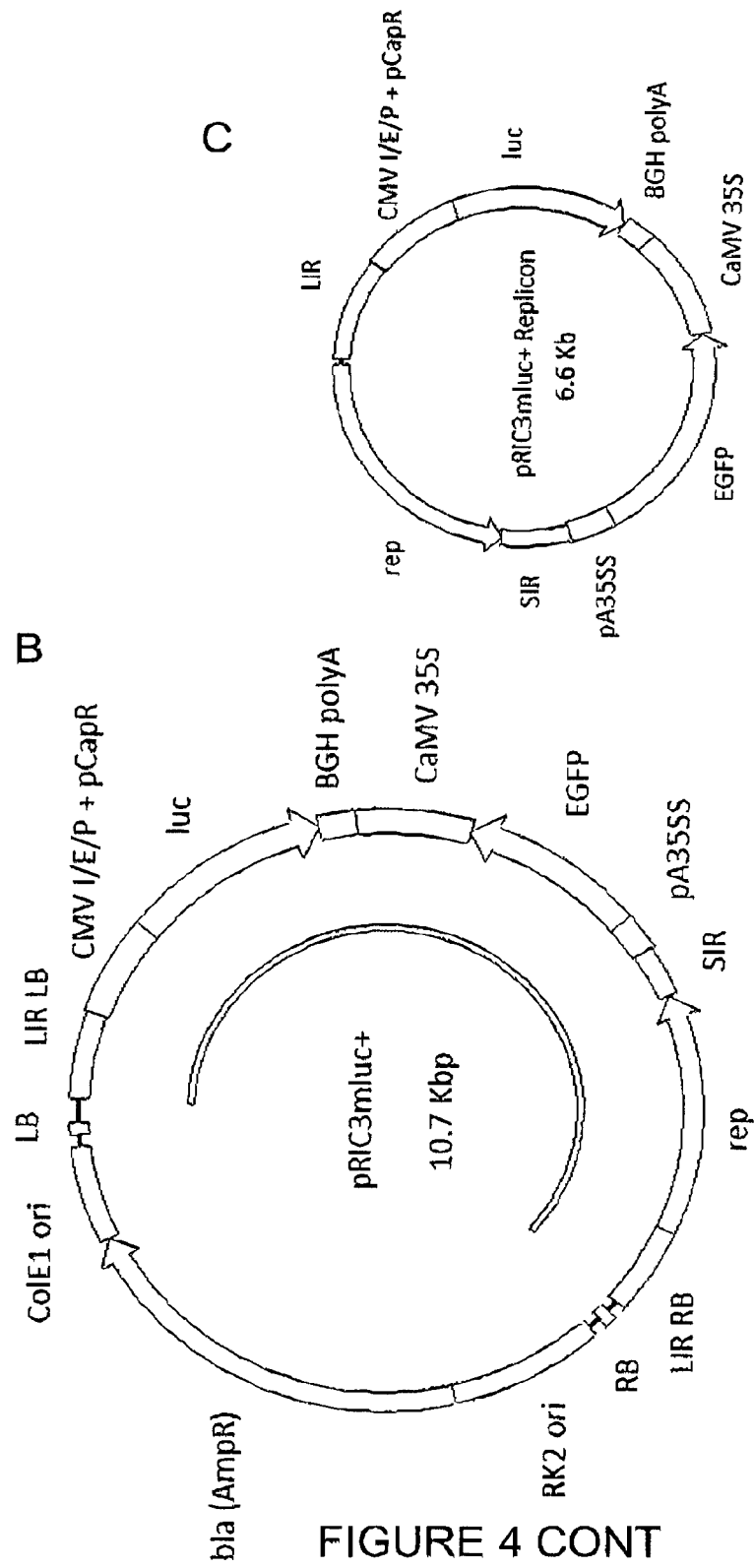

To express pseudovirions (PsVs) in *N. benthamiana* plants, several plant expression vectors were utilised. Replicating vectors were constructed which would replicate in planta to form replicons or pseudogenomes for packaging by HPV L1 and L2 capsid proteins into PsVs. The replicating vectors were constructed by adapting the previously developed geminivirus-derived pRIC3 vector (FIG. 1) to produce the replicating vectors. Two different mammalian expression cassettes encoding genes for the reporter gene products SEAP (mSEAP cassette) and luc (mluc cassette) were utilized to create the replicating vectors. Both of the mammalian cassettes were incorporated into pRIC3 with the extant EGFP plant cassette (+), hereinafter designated mSEAP+ (SEQ ID NO: 9; FIG. 17) and mluc+ (SEQ ID NO: 10; FIG. 18) serving to increase the overall replicon size (pRIC3-mSEAP+ and pRIC3-mluc+), while the SEAP cassette (SEQ ID NO: 8; FIG. 16) was also incorporated in place of the plant cassette to create a smaller replicon (pRIC3-mSEAP). HPV VLPs have been reported to package pseudogenomes of approximately 5-8 Kbp in size, whereas larger or smaller pseudogenomes are not packaged at all (Buck et al., 2004; Touze and Coursaget, 1998). To accommodate these size constraints, three vectors were created with different reporter genes and resulting in replicons of different sizes, namely:

a) pRIC3-mSEAP—pRIC3 with a mammalian cassette encoding the SEAP reporter gene in place of the current plant cassette (4.8 Kbp replicon/pseudogenome) (FIG. 2)

b) pRIC3-mSEAP+—pRIC3 with the addition of a mammalian SEAP cassette, inserted upstream of the plant cassette (6.6 Kbp replicon/pseudogenome) (FIG. 3)

c) pRIC3-mluc+—pRIC3 with the addition of an alternative mammalian cassette encoding the luc reporter gene, inserted upstream of the plant cassette (7.6 Kbp replicon/pseudogenome) (FIG. 4)

Figure 5:
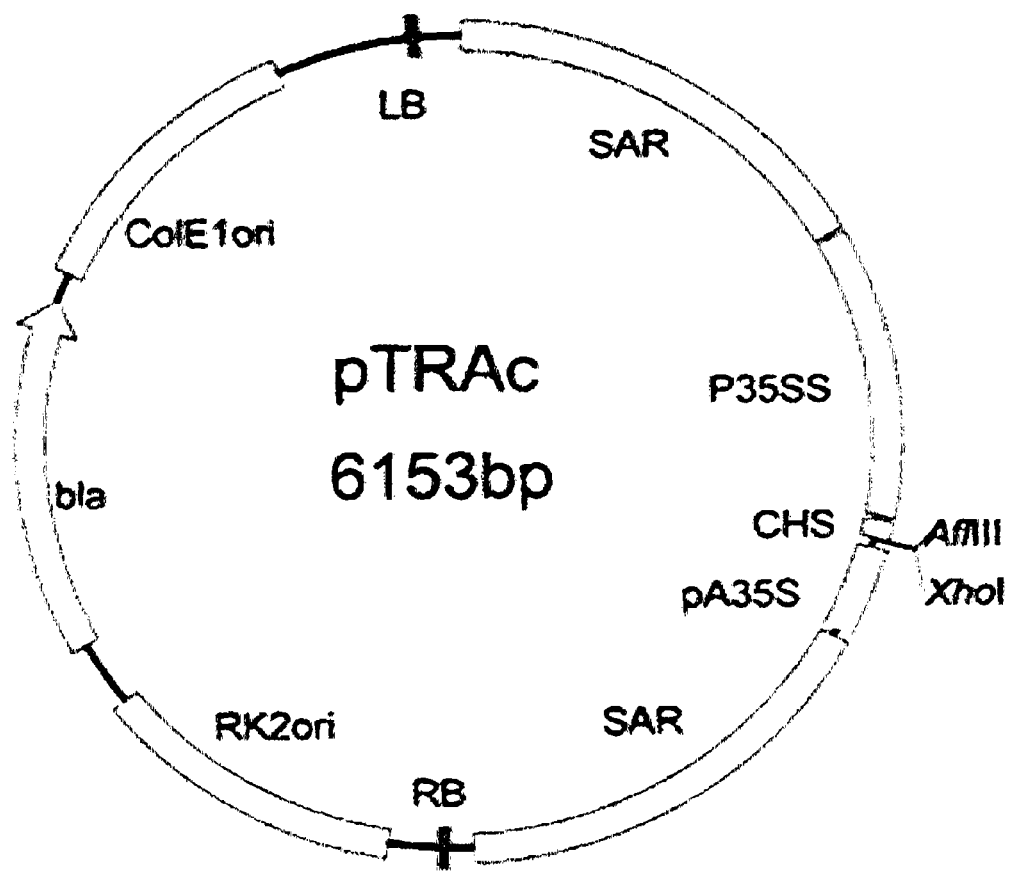
FIG. 5: *Agrobacterium* expression vector pTRAc. P35SS, CaMV 35S promoter with duplicated transcriptional enhancer; CHS, chalcone synthase 5' untranslated region; pA35S, CaMV 35S polyadenylation signal; SAR, scaffold attachment region of the tobacco Rb7 gene; LB and RB, the left and right borders for T-DNA integration; ColE1ori, origin of replication for *E. coli*; RK2ori, origin of replication for *Agrobacterium*; bla, ampicillin/carbenicillin-resistance gene.

Further to these, the plant expression vector pTRAc (gifted by Prof. Dr. Rainer Fischer Fraunhofer Institute for Molecular Biology and Applied Ecology, Germany) expressing HPV-16 L1 (SEQ ID NO: 13) or HPV 16 L2 (SEQ ID NO: 14) human codon-optimised genes (pTRAc-hL1 and pTRAc-hL2, respectively) were used for production of L1 and L2 capsid proteins. This vector, shown in FIG. 5, targets L1 and L2 expression to the cytoplasm, and pTRAc-hL1 has demonstrated high expression levels for L1 in planta (Maclean at al., 2007).

Transformation of *Agrobacterium tumefaciens*

Plasmids were isolated from *E. coli* using a QIAGEN® Plasmid Miniprep Kit. These were then introduced into *Agrobacterium tumefaciens* strain GV3101::pMP90RK via electroporation, as described by Maclean at al. (2007). *A. tumefaciens* cells were made electrocompetent by the method described by Shen and Forde (1989). 200 ng of plasmid DNA was added to a chilled electroporation cuvette (Molecular BioProducts, Inc.), along with 100 µl of electrocompetent cells. After 5 minutes of incubation on ice, cells were electroporated using a Bio-Rad GenePulser® under the following conditions: 1.8 kV, 25 µF, 200 Ω. 900 µl of antibiotic-free Luria broth was added to the electroporated cells, which were incubated for 2 hours at 27° C. Recombinant clones were screened by antibiotic selection with rifampicin (50 µg/ml), carbenicillin (50 µg/ml), and kanamycin (30 µg/ml). Plates were incubated at 27° C. for 48 hours to allow for colony formation, and screened for positive clones by colony PCR.

Agroinfiltration of *N. benthamiana*

Agroinfiltration of *N. benthamiana* plants was performed as described by Maclean et al. (2007). *Nicotiana benthamiana* plants were grown from seed in a controlled plant growth room. The plants were grown at 22° C., with 16 hours of light per day for 6 weeks. Plants were agroinfiltrated by syringe or by vacuum with a bacterial suspension of recombinant *A. tumefaciens* at an optical density (OD) of 0.25, 0.5, 0.75 or 1. Briefly, a syringe was used to force *A. tumefaciens* bacterial suspension into the abaxial air spaces in several leaves per plant. The plants were allowed to grow as normal, and leaf samples were harvested at 1-7 days post infiltration (dpi). For vacuum infiltration, whole plants were submerged in 500 ml of bacterial suspension, and placed in a vacuum chamber. A vacuum of −90 kilopascal (kPa) was maintained for 5 seconds, then rapidly released (10-15 kPa·sec$^{-1}$). Plants were grown as normal, and harvested at 4 dpi.

Quantitative PCR qPCR analysis was performed to determine whether replication of the replicon was occurring in plants. A single 0.5 cm leaf disc was incubated at 95° C. for 10 minutes with 100 µl Extraction Buffer from the Extract'n'Amp Plant PCR Kit (Sigma Aldrich). This was diluted with 100 µl Dilution buffer, and stored at −20° C. until needed. qPCR was performed using the 2× SybrGREEN ReadyMix from the same kit. Primers lucQ-F (5'-CAA CTG CAT AAG GCT ATG AAG AGA-3' (SEQ ID NO:1)) and lucQ-R (5'-ATT TGT ATT CAG CCC ATA TCG TTT-3' (SEQ ID NO:2)) were used to amplify a 153 bp fragment of the luciferase gene, and primers SEAPQ-F (5'-CCT TGA CCC CGC ACA GGT A-3' (SEQ ID NO:3)) and SEAPQ-R (5'-GGC TCT GTC CAA GAC ATA CAA TGT A-3' (SEQ ID NO:4)) were used to amplify an 83 bp fragment of the SEAP gene. All primers were used at a final concentration of 0.4 mM. qPCR cycling was performed on a Corbett RotorGene 6000 (Corbett), using cycling parameters as follows: for the luciferase reaction 95° C. for 2 minutes; 40 cycles of 95° C. for 5 seconds, 57° C. for 5 seconds, and 72° C. for 5 seconds; and melt curve analysis from 72-95° C. for 5 seconds per degree and for the SEAPQ reaction 95° C. for 2 minutes; 40 cycles of 95° C. for 5 seconds, 54° C. for 5 seconds, and 72° C. for 5 seconds; and melt curve analysis from 72-95° C. for 5 seconds per degree. qPCR was performed with three technical repeats per sample, with a sample population size of three (N=3). Data was analysed using RotorGene Q Series 2.0.2 software (Corbett). Ct values were normalised to total DNA concentration for each sample.

Inverse PCR

The replicon construct of the present invention was derived from the genome of Bean yellow dwarf mastrevirus (BeYDV). This includes two copies of the Long Intergenic Region (LIR) of BeYDV, flanking a construct comprising a mammalian promoter to the 5' side of a reporter gene, a BeYDV-derived Short Intergenic Region (SIR), and the BeYDV Rep gene under the control of its native promoter in the LIR sequence. Introduction of the carrier plasmid into plant cells results in transcription from the BeYDV Rep promoter of Rep mRNA, and translation of the Rep protein. This protein binds to the BeYDV Ori within LIR sequences, and causes a single-strand nick in the sequence 5'-TAAT-ATT/AC-3'; host repair polymerases extend the free 3'-end up to the second LIR TAATATTAC sequence. Release of a single-stranded unit-length replicon DNA allows recircularisation via a stem-loop sequence encoded in the LIR, with ligation to a circular molecule by the Rep protein circular ssDNA molecules are converted to dsDNA by host polymerases, and Rep can then be transcribed from these to amplify their presence as autonomous replicons, just as the native virus replicates. Alternatively, a replicon may be generated by the expression in trans of a Rep protein from another co-agroinfiltrated construct, and replication would continue only as long as Rep was co-expressed.

This process occurs in plant cells because the native Rep promoter is recognised by plant transcription factors: this does not appear to happen in mammalian cells, meaning the replicon would be replicationally inert and would only be transcribed to allow expression of the transgene.

Figure 6:
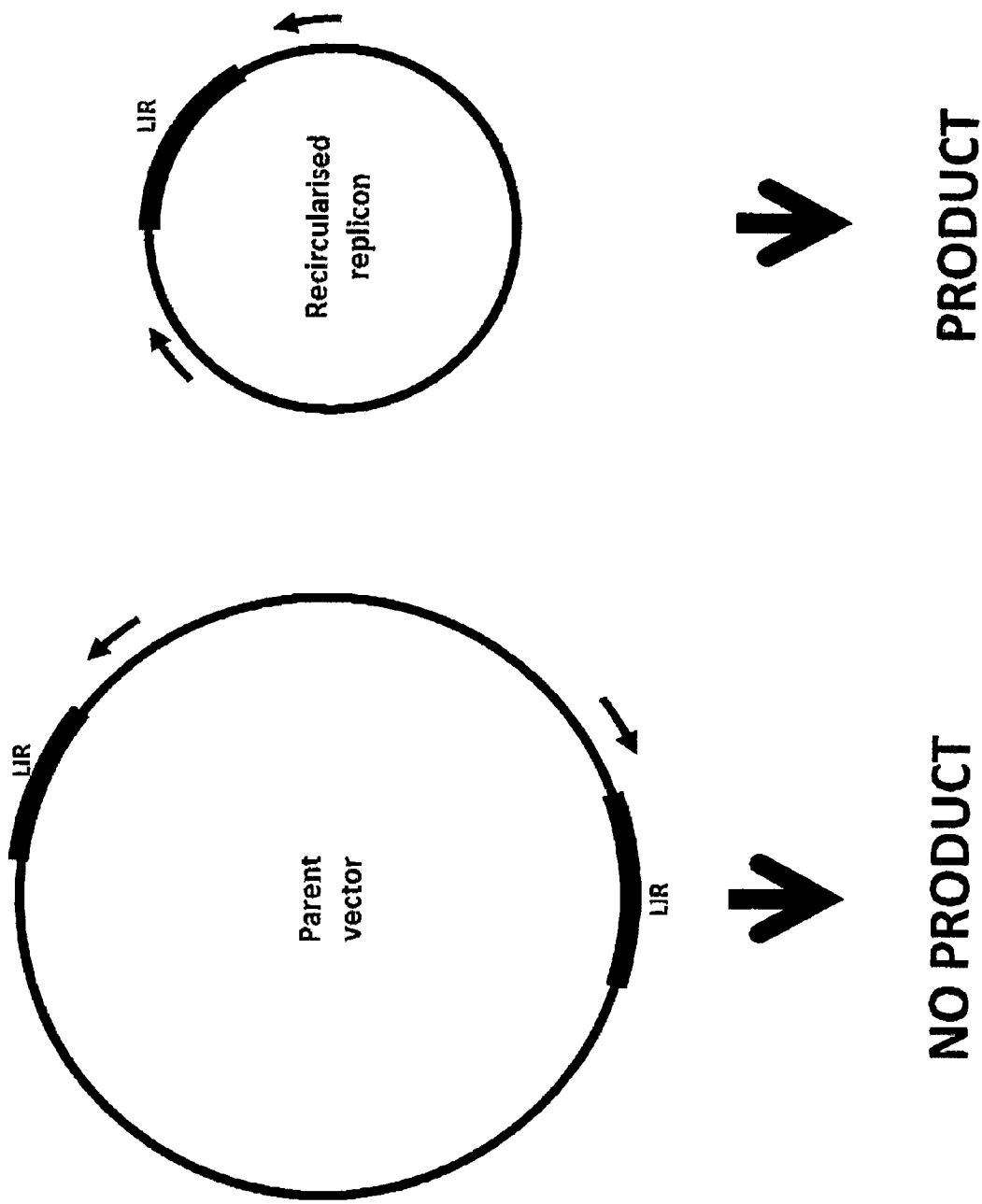
FIG. 6: Principle of Inverse PCR. Diagram illustrating the principle of inverse PCR. Primers (→) designed to amplify only recircularised replicon DNA, but not the parent vector. Vector recircularised at the duplicated LIR.

A variation of inverse PCR, as described by Regnard et al. (2010), was utilised to confirm recircularisation of the replicon (FIG. 6). Primers were designed to amplify a DNA fragment (approximately 2.1 Kbp) encompassing the site of recircularisation for each replicon. PCR reactions to confirm recircularisation of the pRIC3mluc+Replicon were performed with the GoTaq Kit (Promega), 2.5 mM Mg, primers polyA35SS-F (5'-AGG GTT CTT ATA GGG TTT CGC TC-3' (SEQ ID NO:5)) and CMV-R (5'-CCC TGT AAC GTA TGT GAG A-3' (SEQ ID NO:6)), under the following conditions: 95° C. for 3 minutes; 25 cycles of 95° C. for 30 seconds, 60° C. for 30 seconds, 72° C. for 1-3 minutes; and 72° C. for 5 minutes. PCR reactions to confirm recircularisation of the pRIC3mSEAP Replicon and pRIC3mSEAP+ Replicon were performed with the GoTaq Kit (Promega), 2.5 mM $Mg^{2+}$, primers Rep-F (5'-TCC ATC GTG CGT CAG ATT TGC G-3' (SEQ ID NO:7)) and SEAPQ-R (SEQ ID NO:4), under the following conditions: 95° C. for 3 minutes; 25 cycles of 95° C. for 30 seconds, 54° C. for 30 seconds, 72° C. for 1-3 minutes; and 72° C. for 5 minutes.

Replicating Vectors Undergo Replicational Release in Plants

Figure 7:
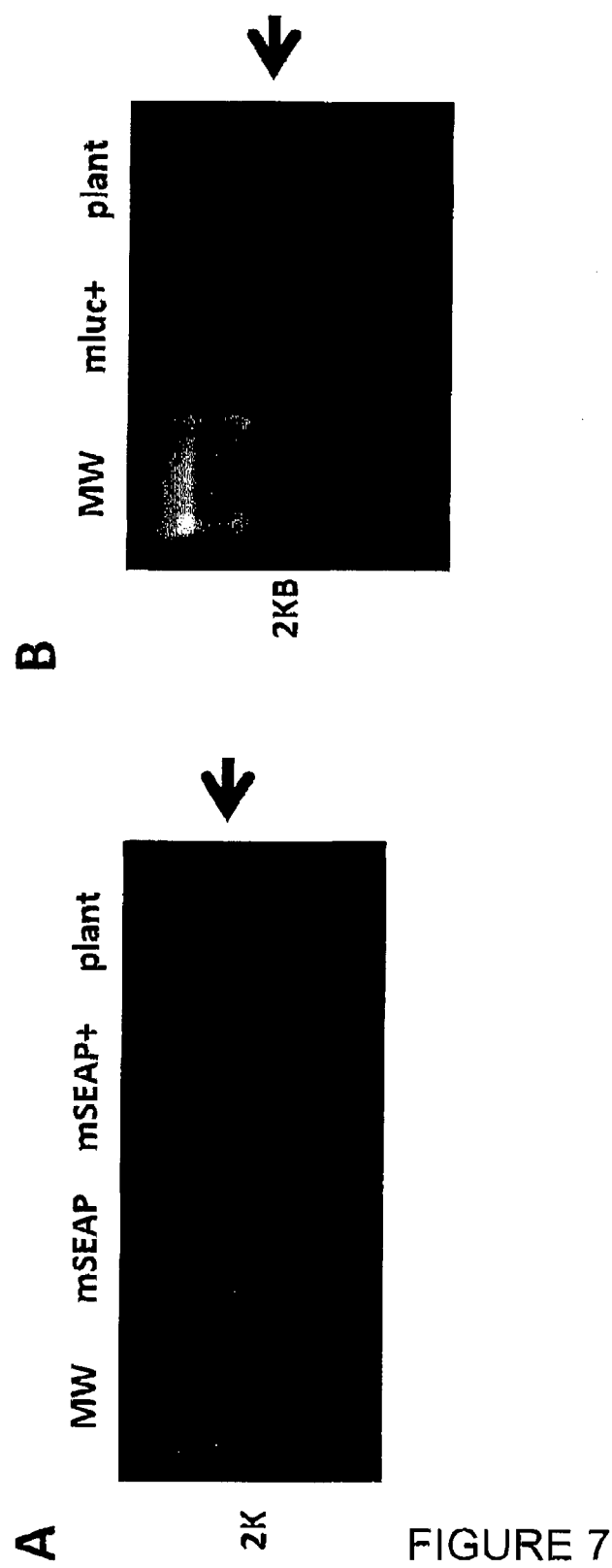
FIG. 7: PCR amplification of (A) pRIC3-mSEAP and pRIC3-mSEAP+ and (B) pRIC3-mluc+ replicons shows replicational release of T-DNA. MW, molecular weight marker; mSEAP, pRIC3-mSEAP; mSEAP+, pRIC3-mSEAP+, mluc+, pRIC3-mluc+, plant, uninfiltrated plant DNA (negative control).

The three novel vectors, pRIC3-mSEAP, pRIC3-mSEAP+ and pRIC3-mluc+ were designed and tested in *N. benthamiana*. All three vectors were cloned into *A. tumefaciens* GV3101::pMP90RK, and plants were infiltrated at an $OD_{600}$ of 0.5. DNA was harvested from plants at 3 dpi, and tested for replicational release by PCR. Primers were designed to amplify a 2.1 Kbp fragment of the replicon, incorporating the LIR (see FIGS. 2C, 3C and 4C) using the Inverse PCR reactions described above for pRIC3mluc+, pRIC3-mSEAP and pRIC3-mSEAP+. According to the design of this experiment PCR amplification product would only be produced in the presence of recircularised replicon. PCR amplification (FIG. 7) of an approximately 2.1 Kbp product confirmed that the replicon was formed in plants individually infiltrated with pRIC3-mSEAP and pRIC3-mSEAP+ (FIG. 7A), and pRIC3-mluc+ (FIG. 7B). This confirms that these vectors form a recircularised replicon in plant cells, and are suitable vectors for pseudogenome production.

Figure 9:
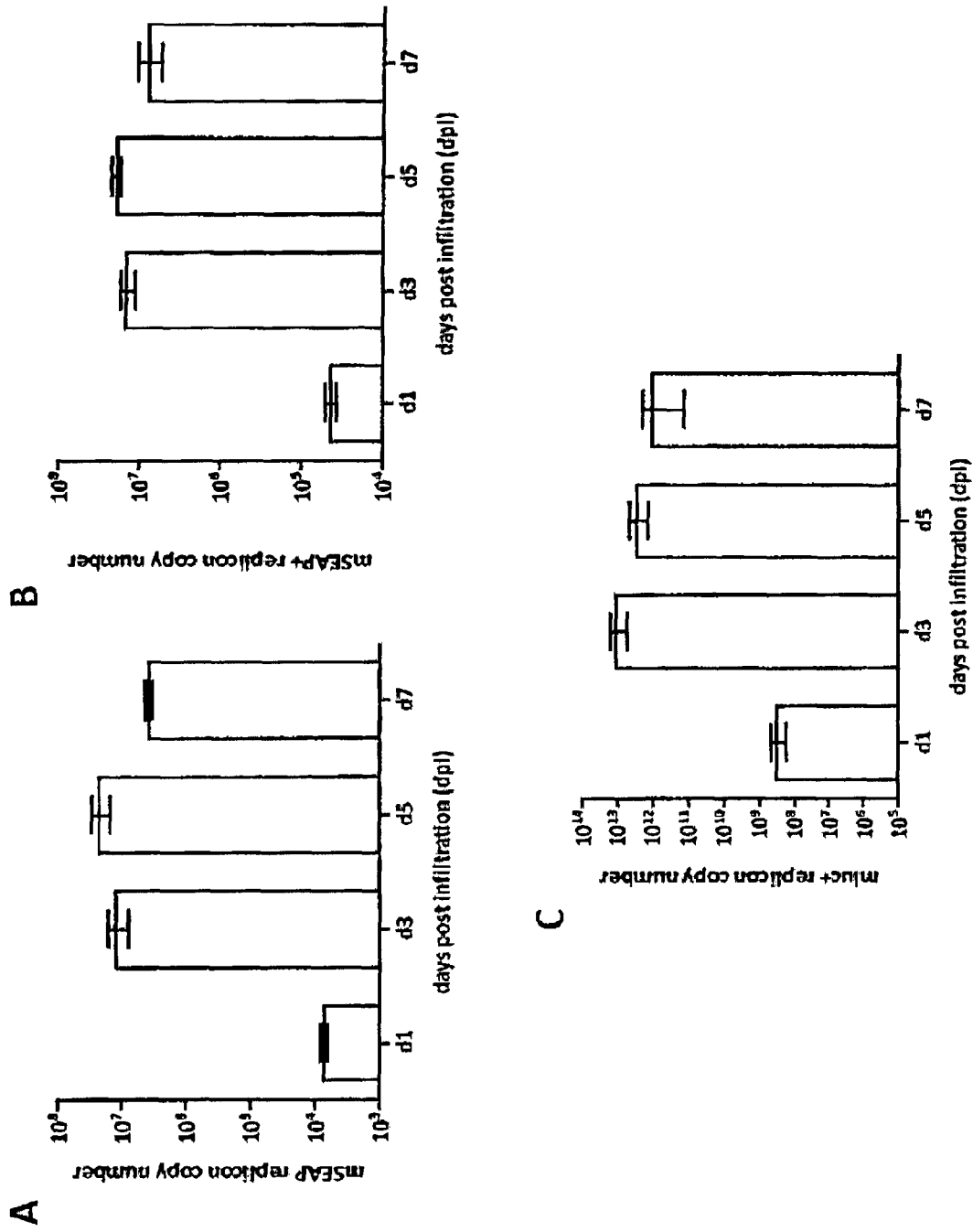
FIG. 9: qPCR time trial of replicating vectors. qPCR analysis of DNA extracted from plants infiltrated with (A) pRIC3-mSEAP, (B) pRIC3-mSEAP+, and (C) pRIC3-mluc+, 1-7 dpi. Copy number is shown as log 10 scale. Error bars indicate standard error of the mean (N=3)

The pRIC3 vector backbone has been previously demonstrated to form replicons that replicate to high copy number within the plant cell, relative to non-replicating vector pTRAc (Regnard et al., 2010). Plants were infiltrated individually with each replicating vector at OD 0.5, and DNA was harvested at 1, 3, 5 and 7 dpi. qPCR was used to determine the increase in replicon copy number from 1 to 7 dpi with each of the replicating vectors using the reactions and reaction conditions described above for pRIC3mluc+, and pRIC3-mSEAP and pRIC3-mSEAP+, respectively. Analysis showed a 100-1000-fold increase in gene copy number for all three vectors at from 1 to 3 dpi, with maintenance at similar copy number up to 7 dpi (FIG. 9). pRIC3-mSEAP (FIG. 9A), pRIC3-mSEAP+ (FIG. 9B) and pRIC3-mluc+ (FIG. 9C) all show very similar increases in copy number. This is consistent with previous observations for pRIC and pRIC3 (Ogle, 2008; Regnard et al., 2010).

The three vectors were tested for their ability to replicate autonomously in plants. PCR analysis confirmed that the appropriate replicons were formed as expected. To elucidate whether the autonomously replicating vectors were, in fact, producing high copy numbers of the replicons in planta, qPCR analysis was employed. qPCR analysis of DNA samples harvested up to 7 dpi showed that replicon copy number for all plasmids was amplified between 100- and 1000-fold between 1 and 3 dpi, and that this high copy number was maintained up to 7 dpi. This is similar to the results obtained by Regnard et al. (2010), who showed a near-identical increase in the pRIC vectors used to generate replicons encoding the HIV p24 gene or EGFP. Replicating vectors developed by other groups have demonstrated similar increases in replicon copy number (Huang et al., 2009; Zhang and Mason, 2006). Our result demonstrates that the use of these replicating vectors for the generation of high quantities of replicon DNA in plants is a feasible strategy for producing sufficient pseudogenome DNA in plant host cells for PsV production.

Example 2

PsVs Production in Planta
SDS-PAGE and Western Blotting

SDS-PAGE was performed to analyse HPV-16 hL1 and hL2 protein production in plants. Protein was extracted from plants agroinfiltrated with *A. tumefaciens* GV3101:: pMP90RK pTRAc-hL1 and/or pTRAc-hL2. Briefly, three 0.5 cm leaf discs were harvested at 1, 3, 5, and 7 dpi, frozen in liquid $N_2$, and ground in a microcentrifuge tube using a plastic pestle. 100 µl of 0.5M NaCl PBS with 1× complete EDTA-free protease inhibitor cocktail (Roche) (hL1) or 8M urea in H2O (hL2) was added to the ground leaf material and mixed thoroughly. Samples were centrifuged at 13000 rpm for 5 minutes, and the supernatant was reserved. This centrifugation step was repeated, and the supernatant was stored at −20° C. For SDS-PAGE analysis, 8 µl of 5× loading dye containing β-mercaptoethanol was added to 32 µl of soluble protein, and samples were incubated at 95° C. for 7 minutes. These were then loaded on 10% SDS-polyacrylamide gels using the Mini-PROTEAN® Tetra SDS-PAGE system (Bio-Rad), and electrophoresed at 130V for approximately 120 minutes. These gels, and nitrocellulose membranes, were equilibrated for 10 minutes in transfer buffer before being transferred to a nitrocellulose membrane at 15V for 90 minutes using a Bio-Rad Trans-Blot® SD Semi-Dry Electrophoretic Transfer Cell. Membranes were incubated with blocking buffer for 60 minutes, then probed for L1 overnight, using commercially available CamVir-1 primary monoclonal antibody (Abcam, ab69) diluted 1 in 10000 in blocking buffer. Membranes were washed for 4×10 minutes in blocking buffer, probed with goat anti-mouse AP-conjugated secondary antibody (Sigma, A3562) diluted 1 in 5000 in blocking buffer for two hours, washed 4×10 minutes in blocking buffer without skim milk powder, and visualised using BCIP/NBT Phosphatase substrate (KPL). For L2, a similar protocol was employed. Primary antibody was rabbit-produced anti-L2 primary polyclonal serum produced in our laboratory and used at 1 in 5000 dilution, and secondary antibody was goat anti-rabbit AP-conjugated antibody (Sigma, A3687).

Optimisation of Protein Expression in Plants

Figure 8:
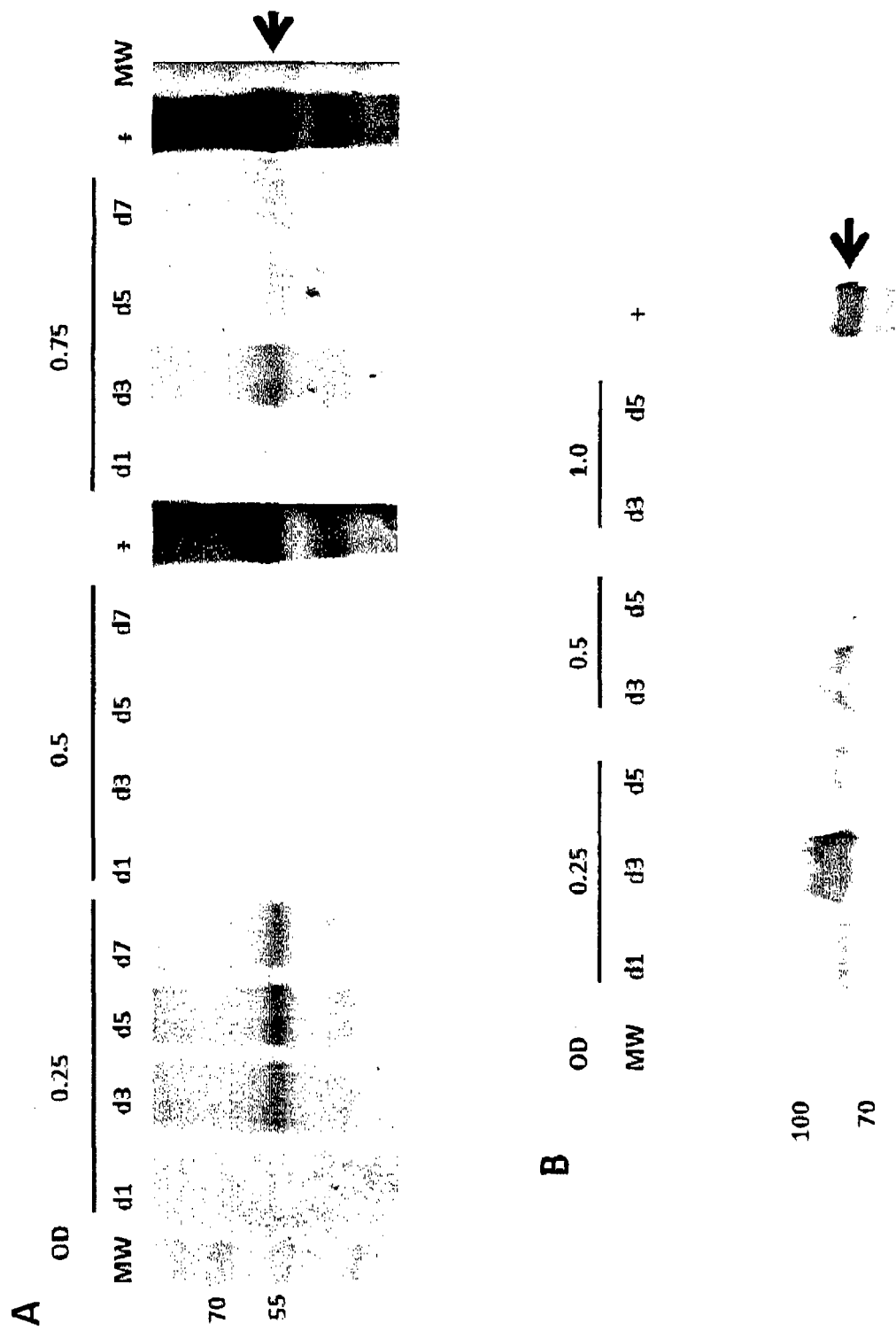
FIG. 8: Optimisation of L1 and L2 expression. Time trial of (A) hL1 and (B) hL2 expression levels at various infiltration ODs, at 1-7 and 1-5 dpi, respectively. Protein is indicated (→) at 55 kDa (hL1) and approximately 65 kDa (hL2). MW, molecular weight marker, with sizes indicated in kDa; +, crude plant-produced hL1 (A) and bacterially-produced hL2 (B)

Expression of hL1 and hL2 was optimised by a 1-7 dpi time trial. Plants were agroinfiltrated with a range of bacterial suspension $OD_{600}$ values (0.25-1.0). Protein was harvested at 1, 3, 5, and 7 dpi, and separated by SDS-PAGE. hL1 and hL2 expression was analysed by western blotting using anti-L1 CamVir-1, and an anti-L2 polyclonal antibody raised in rabbits (FIG. 8), respectively. Expression of recombinant protein was detected at all $OD_{600}$ values tested, from 3 dpi, for both hL1 and hL2, at the expected size. While L2 is an approximately 50 kDa protein, it has been widely observed to migrate at approximately 80 kDa (Muller at al., 1995). The highest expression detected for hL1 was at $OD_{600}$ 0.25, from 3-7 dpi (FIG. 8A). The highest expression of hL2 was also seen in those plants infiltrated at $OD_{600}$ 0.25, at 3 dpi (FIG. 8B). As such, agroinfiltration parameters of $OD_{600}$ 0.25 at 4 dpi was chosen for optimal hL1 and hL2 expression in further experiments.

Production of PsVs in Plants

Figure 10:
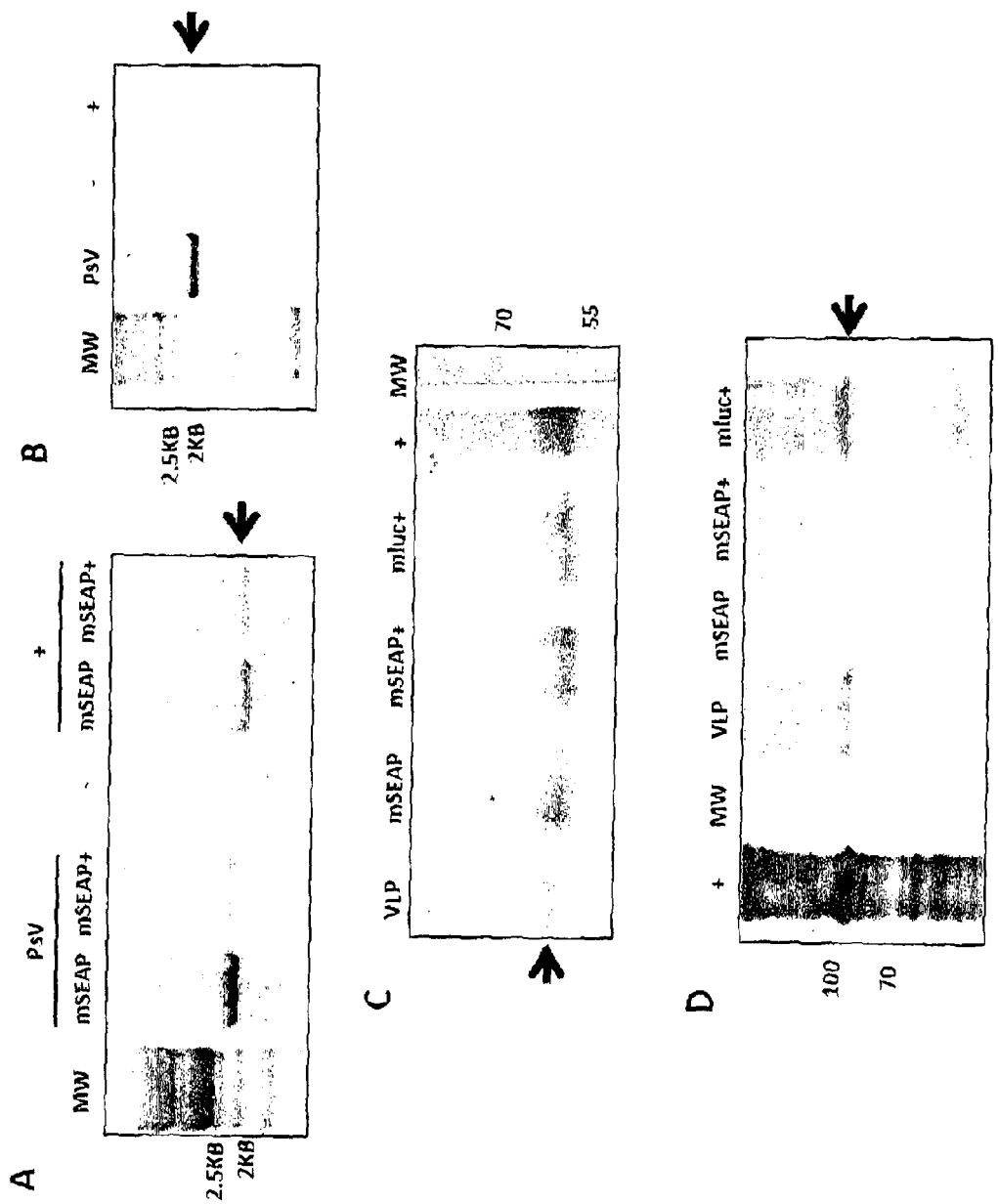
FIG. 10: Expression of PsV structural elements. PCR was used to confirm presence of (A) pRIC3-mSEAP, pRIC3-mSEAP+, and (B) pRIC3-mluc+ replicons 3 dpi, in plants co-infiltrated with pTRAc-hL1, pTRAc-hL2 and pRIC3-mSEAP, -mSEAP+ or -mluc+, respectively. A band at approximately 2.1 Kbp (→) indicates replicational release. MW, molecular weight marker, sizes shown on left; PsV, crude plant extract; +, DNA only (positive control); −, plant DNA (negative control). Western blotting for L1 (C) and L2 (D) confirm presence of both structural HPV proteins 4 dpi in crude extract from plants co-infiltrated with pTRAc-hL1, pTRAc-hL2 and pRIC3-mSEAP, -mSEAP+ or -mluc+. VLP, pTRAc-hL1 and -hL2 only; mSEAP, pRIC3-mSEAP PsV; mSEAP+, pRIC3-mSEAP+ PsV; mluc+, pRIC3-mluc+ PsV; +, crude plant-produced hL1 (C) or bacterially produced L2 (D); MW, molecular weight marker, sizes indicated in kDa.

To produce HPV PsVs, *N. benthamiana* plants were co-infiltrated with pTRAc-hL1, pTRAc-hL2, along with each of pRIC3-mSEAP, pRIC3-mSEAP+, and pRIC3-mluc+, separately. Based on data demonstrated above, agroinfiltration with pTRAc vectors was at an $OD_{600}$ of 0.25, while replicating vectors were agroinfiltrated at $OD_{600}$ of 0.5, and particles were harvested at 4 dpi. pTRAc-hL1 and pTRAc-hL2 were also co-infiltrated without a replicating vector, with the intention of producing HPV L1/L2 VLPs. This was performed by vacuum infiltration for the production of large volumes of biomass. DNA and crude protein were extracted at 4 dpi, in order to confirm the presence of all components necessary for PsV formation by PCR and western blotting (FIG. 10). PCR amplification of a 2.1 Kbp fragment confirmed that replicon formation was occurring for all three replicating constructs at 4 dpi (FIG. 10, panels A and B). Lanes demarcated 'PsV' indicate replicon formation in plants co-infiltrated with pTRAc-hL1 and -hL2, while those marked '+' are from plants infiltrated with replicating vector alone, and serve as a positive control. Western blotting analysis with CamVir-1 (hL1) and a rabbit polyclonal antibody (hL2) confirmed expression of both L1 (FIG. 10C) and L2 (FIG. 10D) at 4 dpi, in plants infiltrated with L1 and L2 alone ('VLP'), or L1 and L2 coinfiltrated with a replicating vector ('mSEAP', 'mSEAP+' and 'mluc+'). This was independently confirmed in at least three separate co-infiltration experiments. Notably, the intensity of the band corresponding to L2 (FIG. 10D) showed marked variability between repeats in all constructs.

The production of HPV-16 PsVs in plants was successful for each of the three replicating vectors constructed. This work relied on the findings of several earlier papers, in particular that of Maclean et al. (2007). That study demonstrated that humanised L1 was expressed at high levels, and spontaneously assembled into VLPs in planta using the pTRAc vector. This, along with unpublished results for pTRAc-hL2 from the same group, demonstrated the feasibility of these vectors for HPV particle production in plants.

It has been widely demonstrated that both HPV L1 and L2 are required for efficient packaging of DNA into the HPV virion, in both natural virions and PsVs (Ma at al., 2011; Okun at al., 2001; Stauffer at al., 1998). Further, it was recently established that the presence of L2 in the PsV capsid increases DNA packaging efficiency 10-fold (Holmgren et al., 2005). In this study, both L1 and L2 were co-expressed to allow for maximum potential DNA encapsidation. No investigations into differential packaging in the presence and absence of L2 were performed; however, little or no L1 signal was visible in fractions 14-16 (buoyant density 1.26-1.28 g/ml—corresponding to the density of VLPs with no encapsidated DNA). This lack of 'light' particles suggests that packaging of DNA by HPV particles in plants is very efficient indeed, resulting in few or no particles without encapsidated DNA. This is in contrast to other PsV production methods, all of which show a peak corresponding to 'light' particles, or VLPs. This is in particular true for the VLP disassembly-reassembly method (as demonstrated by Touze and Coursaget (1998)), which usually has a packaging efficiency well below 50% (Touze and Coursaget, 1998; Unckell at al., 1997).

This efficient packaging is a distinct advantage for the plant production approach, although this must be tempered with the observation that not all DNA packaged is necessarily pseudogenome DNA. This is clearly demonstrated by the L1/L2 VLPs produced here, which were seen to be mostly 'heavy' particles, indicating encapsidated DNA. As these were produced in the absence of a replicating vector, DNA packaged was either the pTRAc plasmids used to produce VLPs, or miscellaneous plant DNA. Both pTRAc-hL1 and pTRAc-hL2 (7.7 Kbp and 7.5 Kbp, respectively) fall below the maximum size of 7.9-8 Kbp for pseudogenomes that can be packaged effectively into HPV L1/L2 PsVs (Buck at al., 2005b; Touze and Coursaget, 1998). It is possible that these plasmids, or miscellaneous DNA, were packaged into assembling HPV particles instead of the intended replicon DNA—it has been suggested that VLPs produced in mammalian cells encapsidate miscellaneous cellular DNA (Roden et al., 1996). In any event, the extremely efficient replication observed in the three replicating vectors used here, as well as that observed when pRIC was compared to pTRAc in a previous study (Regnard at al., 2010), suggest that the vast majority of plasmids present in the plant during PsV assembly would be the reporter pseudogenomes. As such, the potential for pTRAc plasmids to be packaged may not hold any relevance to the outcome of this study. Future work to elucidate all DNA species encapsidated into plant-produced PsVs is important for a full understanding of the PsV assembly process in planta, as well as for their use in neutralising assays.

Structural analyses of L1 and L2 suggest that DNA associates in a non-specific manner, based on the overall pH and charge of internal structural motifs (Fay et al., 2004; Garcea and Gissmann, 2004; Li et al., 1997; Pereira et al., 2009). Presumably, this allows for in vitro PsV assembly, demonstrated by several investigators, in the absence of mammalian cellular factors (Oh et al., 2004; Shi et al., 2001; Touze and Coursaget, 1998). In mammalian cells, there is evidence to suggest that chaperones (particularly karyopherins) play a role in the assembly and DNA packaging of natural HPV virions, and it seems likely that these are responsible for efficient intracellular PsV production (Bird et al., 2008; Chromy et al., 2006). Chaperones, in particular Heat shock protein 70 (Hsp70) and karyopherins, have been shown to play a role in the assembly of diverse viruses, including plant viruses (Kunik et al., 1999; Sullivan and Pipes, 2001). Interestingly, the ER associated chaperone Binding Protein (BiP) has been demonstrated to take part in folding and assembly of recombinant antibodies in transgenic plants (Nuttall et al., 2002). These data suggest that the molecular machinery required for papillomavirus assembly and DNA encapsidation is conserved across all eukaryote systems, and is responsible for the efficient PsV assembly observed here.

Example 3

Purification of Pseudovirions
Extraction and Purification of Particles

To produce particles, plants were vacuum-infiltrated with *A. tumefaciens* GMV3101::pMP90RK containing pTRAc-hL1, pTRAc-hL2 and either pRIC3luc, pRIC3mSEAP or pRIC3mSEAP+. Protein and DNA were harvested at 4 dpi, as described above. Western blotting, as described above, was used to confirm the presence of L1 and L2 protein, and inverse PCR, as described above, was used to confirm that replicational release had taken place. Whole plants were harvested 4 dpi. Particles were purified following a variation of the protocol described by Varsani et al. (2003), with some modifications. Whole leaves were weighed, and ground with liquid nitrogen in a pestle and mortar, or macerated thoroughly at room temperature. Cold 0.5M NaCl PBS was added to the leaf material at a ratio of 1:2 (w.v), and samples were homogenised in an T25 Ultra-Turrax high shear mixer (IICA®) at 13000 rpm for 10 minutes on ice. Homogenate was kept on ice for a further 2 hours before being centrifuged at 8000 g for 20 minutes at 4° C. in a Beckman Coulter Avanti J25i centrifuge with a Beckman JA-14 rotor. Supernatant was filtered through 4 layers of Miracloth (Calbiochem), and layered onto a 7 ml, 40% sucrose cushion (w/v). The samples were centrifuged at 100000 g for 3 hours at 4° C. in an Optima™ L-100 XP centrifuge (Beckman Coulter) with a Beckman Coulter SW32Ti rotor. The supernatant and sucrose cushion were removed, the pellet was resuspended in 1 ml 0.4 g/ml CsCl in PBS, and clarified on an Eppendorf 5424 tabletop centrifuge at 13000 rpm for 10 minutes. The supernatant was diluted in 5 ml of 0.4 g/ml CsCl in PBS, and subjected to centrifugation at 100000 g for 24 hours in an L-100 XP ultracentrifuge with a Beckman SW55Ti rotor at 10° C.

Identification of VLPs and Pseudovirions in CsCl Gradient

After centrifugation, the CsCl gradient was fractionated manually or using a Foxy Jr. fractionator (ISCO). The density of each fraction was determined using a hand refractometer (ATAGO) to read the refractive index at 25° C., and International Critical Tables (Kellogg, 1927) were used to convert refractive index to buoyant density.

A dot blot was performed to confirm the presence of L1 in the CsCl fractions. Briefly, 1 µl of each fraction was dropped onto a nitrocellulose membrane. The membrane was blocked for 30 minutes in blocking buffer, then probed for L1 as described above. Membranes were scanned and analysed using GeneTools densitometry software (SynGene), and relative spot intensity was normalised to L1 presence in crude plant extract. L1-positive fractions were pooled and dialysed overnight against 0.5M NaCl in PBS to remove CsCl.

In order to confirm the presence of the DNA replicon in the PsVs, Proteinase K was added to the fractions, which were incubated at 55° C. for 3 hours to allow full digestion of the PsV protein shell, before undergoing inactivation at 95° C. for 10 minutes. Inverse PCR was used to amplify an approximately 2.1 Kbp DNA fragment from the samples, for the pRIC3mluc+Replicon reactions were performed with the GoTaq Kit (Promega), 2.5 mM Mg$^{2+}$, primers polyA35SS-F (5'-AGG GTT CTT ATA GGG TTT CGC TC-3' (SEQ ID NO:5)) and CMV-R (5'-CCC TGT AAC GTA TGT GAG A-3' (SEQ ID NO:6)), under the following conditions: 95° C. for 3 minutes; 25 cycles of 95° C. for 30 seconds, 60° C. for 30 seconds, 72° C. for 1-3 minutes; and 72° C. for 5 minutes. PCR reactions to confirm recircularisation of the pRIC3mSEAP Replicon and pRIC3mSEAP+ Replicon were performed with the GoTaq Kit (Promega), 2.5 mM Mg$^{2+}$, primers Rep-F (5'-TCC ATC GTG CGT CAG ATT TGC G-3' (SEQ ID NO:7)) and SEAPQ-R (SEQ ID NO:4), under the following conditions: 95° C. for 3 minutes; 25 cycles of 95° C. for 30 seconds, 54° C. for 30 seconds, 72° C. for 1-3 minutes; and 72° C. for 5 minutes.

Electron Microscopy

To confirm the presence of VLPs and PsVs, transmission electron microscopy (TEM) was used. Copper grids were rendered hydrophilic by glow-discharge using a Model 900 SmartSet Cold Stage Controller (Electron Microscopy Sciences) at 25 mA for 30 seconds. Grids were incubated for 1-30 minutes with VLP or PsV samples, washed three times with dH2O, and particles were stained with 2% uranyl acetate (w/v). Grids were viewed on a Tecnai F20 transmission electron microscope (FEI) or a LEO912 transmission electron microscope (Zeiss) at 14500×, 19000× or 50000× magnification. 10 fields of view were captured at 50000× magnification for all samples, and three fields of view were captured at 19000× magnification for L1/L2 VLP samples, and 14500× for PsV samples.

Purification and Identification of Plant-Produced PsVs

Having confirmed the presence of all necessary elements comprising PsVs in infiltrated plants (L1 protein, L2 protein, as well as mSEAP, mSEAP+ and mluc+ replicons), VLPs and PsVs were isolated from crude plant extract using variations of the method described by Varsani et al. (2003). Briefly, homogenised PsV-containing plant material was subjected to ultracentrifugation on a 40% sucrose cushion. The resulting pellet was resuspended in 0.4 g/ml CsCl in PBS, and subjected to isopycnic ultracentrifugation to separate particles on the basis of buoyant density.

Figure 11:
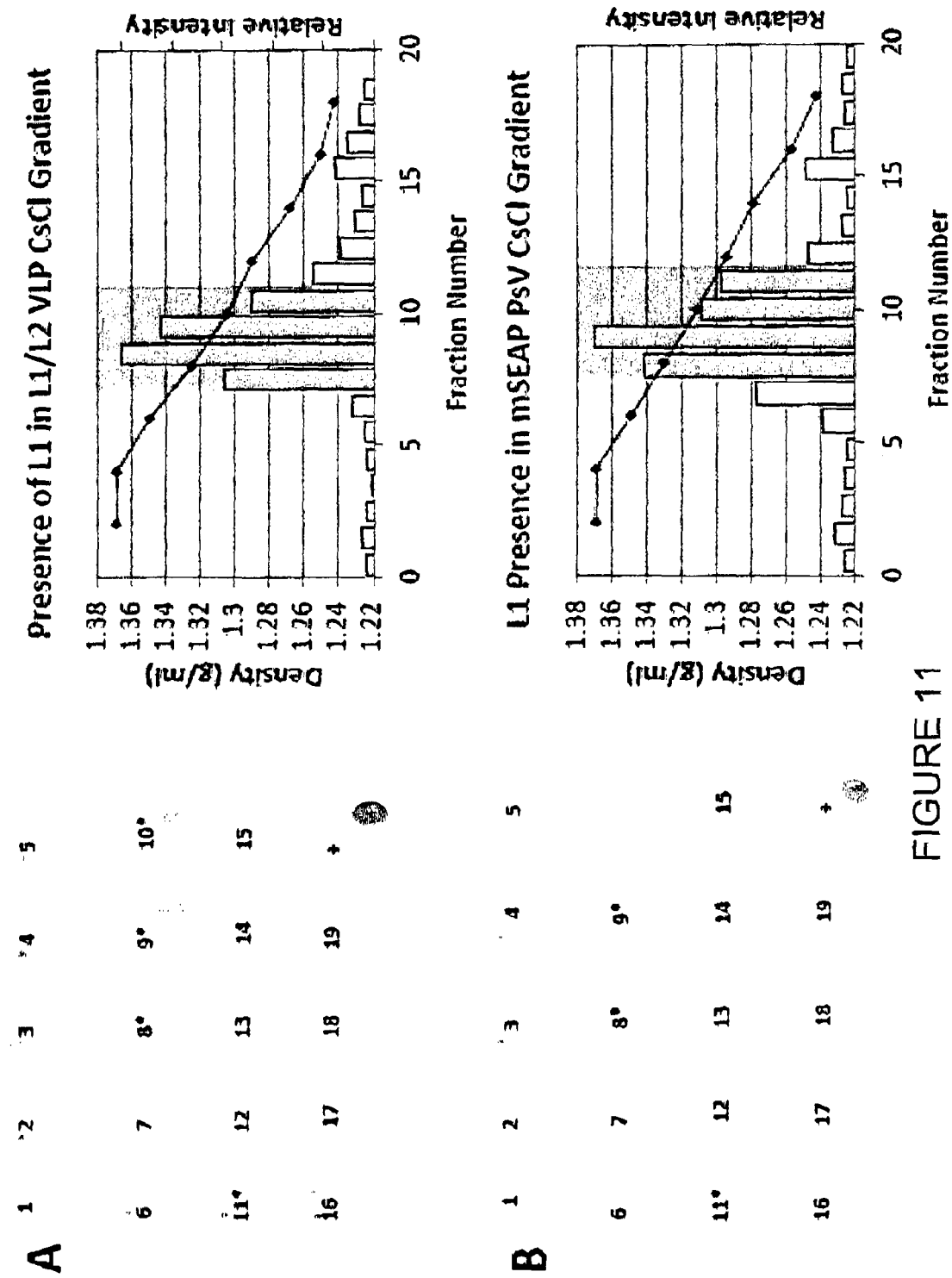
FIG. 11: Caesium chloride gradient ultracentrifugation of VLPs and PsVs. Densitometry analysis of L1 dot blots shows distribution of L1 after Caesium chloride ultracentrifugation and fractionation. Dot Blots (left panels) of CsCl fractions 1-19 were probed with CamVir-1 anti-L1 antibody. * on dot blots, and grey panel on graphs, indicate fractions pooled for dialysis; +, crude plant extract (positive control). Density of CsCl fractions (♦) was compared to relative intensity (□, arbitrary units) of L1 (right panels) to estimate density of purified particles. (A) L1/12 VLPs, (B) pRIC3-mSEAP, (C) pRIC3-mSEAP+, (D) pRIC3-mluc+.

After centrifugation, samples were fractionated and analysed for the presence of L1 by dot blotting, using anti-L1 CamVir-1, as it was thought that this would indicate the presence of VLPs and PsVs as a result of its association with L1, a vital component of these particles. Densitometry analysis of L1 signal on the dot blots indicated the presence of putative HPV VLPs or PsVs, and compared to the buoyant density of each fraction of the gradient, calculated as a function of refractive index (FIG. 11). Previous work has reported that HPV L1/L2 VLPs with encapsidated DNA (PsVs) have a buoyant density of 1.32-1.34 g/ml, while VLPs (without DNA) have a buoyant density of 1.26-1.28 g/ml (Rossi et al., 2000; Touze and Coursaget, 1998). L1 was seen to be present in all fractions, with a distinct peak in signal corresponding to a buoyant density of 1.33 g/ml, suggesting that these particles contain encapsidated DNA (FIG. 11). Interestingly, L1/L2 VLPs demonstrated an L1 peak at a buoyant density of 1.30-1.33 g/ml, which corresponds to a 'heavy' particle (FIG. 11A). This suggests that these particles encapsidated DNA with similar efficiency to those co-infiltrated with replicating vectors. A secondary peak was seen at a density of 1.25 g/ml in L1/L2 VLPs (FIG. 11B) and at a density of 1.27 g/ml in particles purified from plants infiltrated with pRIC3-mSEAP (FIG. 11B). This suggests that in these two samples, small quantities of particles were formed without encapsidated DNA. These results are each representative of at least three separate purification procedures. Fractions 8-11 were pooled and dialysed against high-salt PBS to obtain purified PsVs, and fractions 17-18 were pooled and dialysed as a non-PsV control. These were used for further analysis by electron microscopy, western blotting, and PCR.

Figure 12:
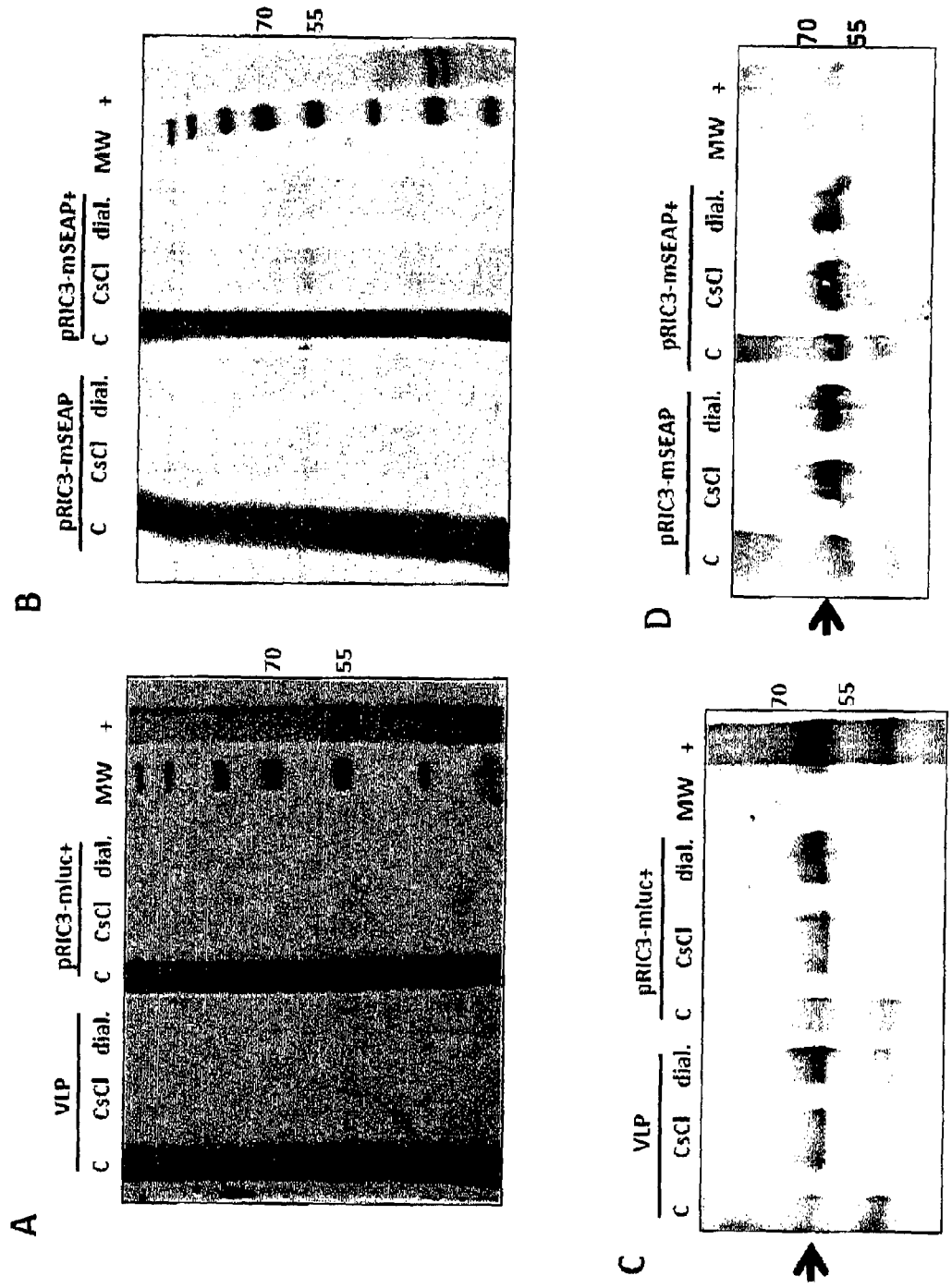
FIG. 12: Purification of PsVs. Coomassie staining (A, B) and western blot for L1 (C, D) of various stages of purification of PsVs, separated by SDS-PAGE. Western blots were probed for L1 using the commercial anti-L1 antibody CamVir-1. MW, molecular weight marker, sizes shown on right; C, crude plant extract; CsCl, pooled caesium chloride gradient fractions; dial., dialysed pooled fractions, +, crude hL1 extract (positive control)

FIG. 12 shows several key stages in the purification process, separated on and SDS-PAGE gel. Coomassie staining reveals the removal of the majority of protein contaminants from the purified samples (FIGS. 12A and 12B). A protein band is present at approximately 55 kDa in purified samples in both FIGS. 12A and 12B, which is likely purified L1. L2, which migrates at approximately 90 kDa, is not visible in the Coomassie-stained gels. This is expected, as L2 is present in HPV VLPs and PsVs in much smaller quantities than L1 (a maximum ratio of L1:L2 is estimated at 5:1). Western blotting analysis with CamVir-1 shows a clear increase in concentration and purity of L1 in all samples (FIGS. 12C and 12D).

Figure 13:
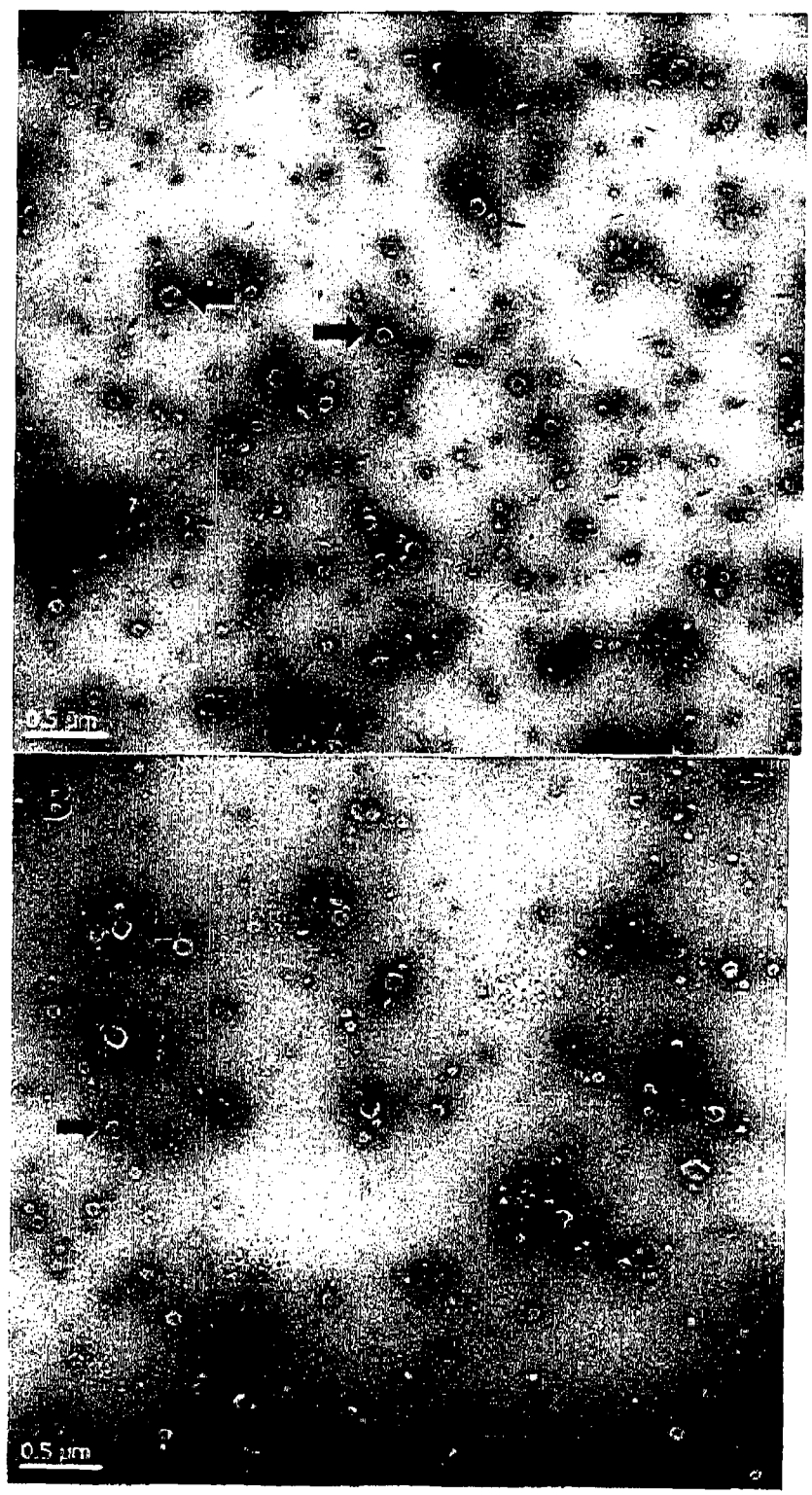
FIG. 13: Electron micrographs of purified PsVs. (A) and (E) pRIC3-mSEAP, (B) and (F) pRIC3-mSEAP+, (C) and (G) pRIC3-mluc+ PsVs (previous page) and (D) and (H) L1/L2 VLPs were purified by CsCl gradient ultracentrifugation. Purified PsVs size varied from 30-120 nm in diameter. White arrows indicate small (30-40 nm) particles, Grey arrows indicate standard-sized HPV PsV particles (50-60 nm), and black arrows indicate large (100-120 nm) particles. (I) Crude plant extract serves as negative control. Scale bars are indicated (left panel, 0.5 µm; right panel and (D), 200 nm, (I), 100 nm).
Figure 13:
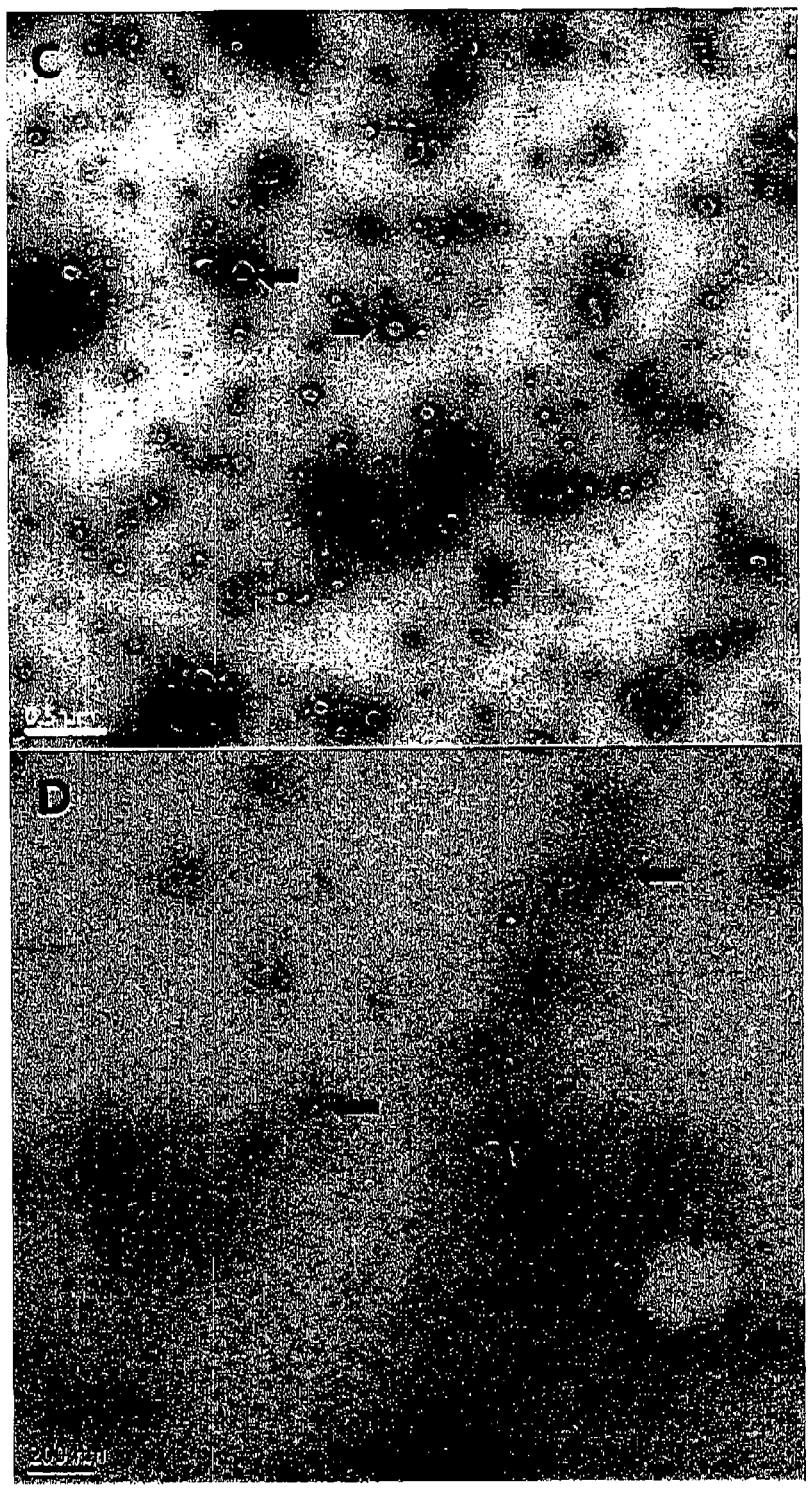
Figure 13:
Figure 13:
Figure 13:
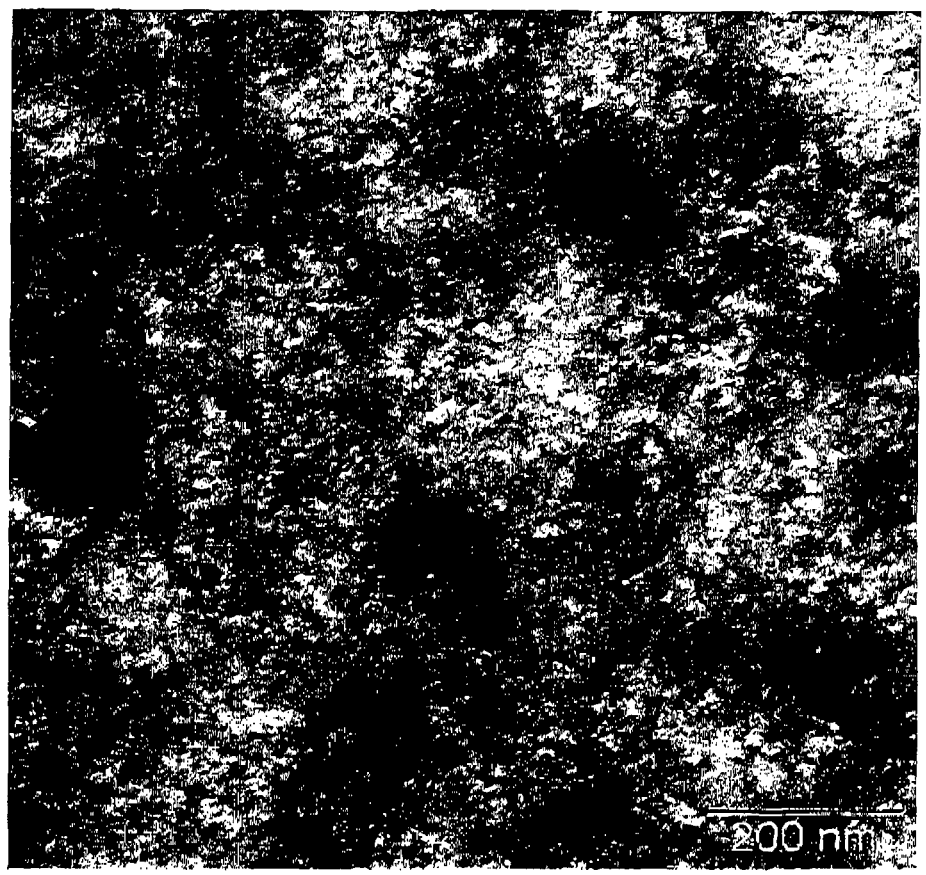

In order to further confirm the presence of L1/L2 VLPs and PsVs, dialysed samples were examined by transmission electron microscopy (FIG. 13). All samples showed the presence abundant particles, of sizes ranging from 30-120 nm. 54% of mSEAP-PsVs (FIGS. 13A and 13E) were 40-70 nm in diameter, while 47% of mSEAP+-PsVs (FIGS. 13B and 13F) and 50% of mluc+-PsVs (FIGS. 13C and 13G) 73% of L1/L2 VLPs (FIGS. 13D and 13H) were of a similar size. Infectious HPV virions are usually between 50 and 60 nm in diameter. These particles showed a similar morphology to other examples of plant-produced HPV particles (Maclean et al., 2007; Warzecha eat al., 2003).

Figure 14:
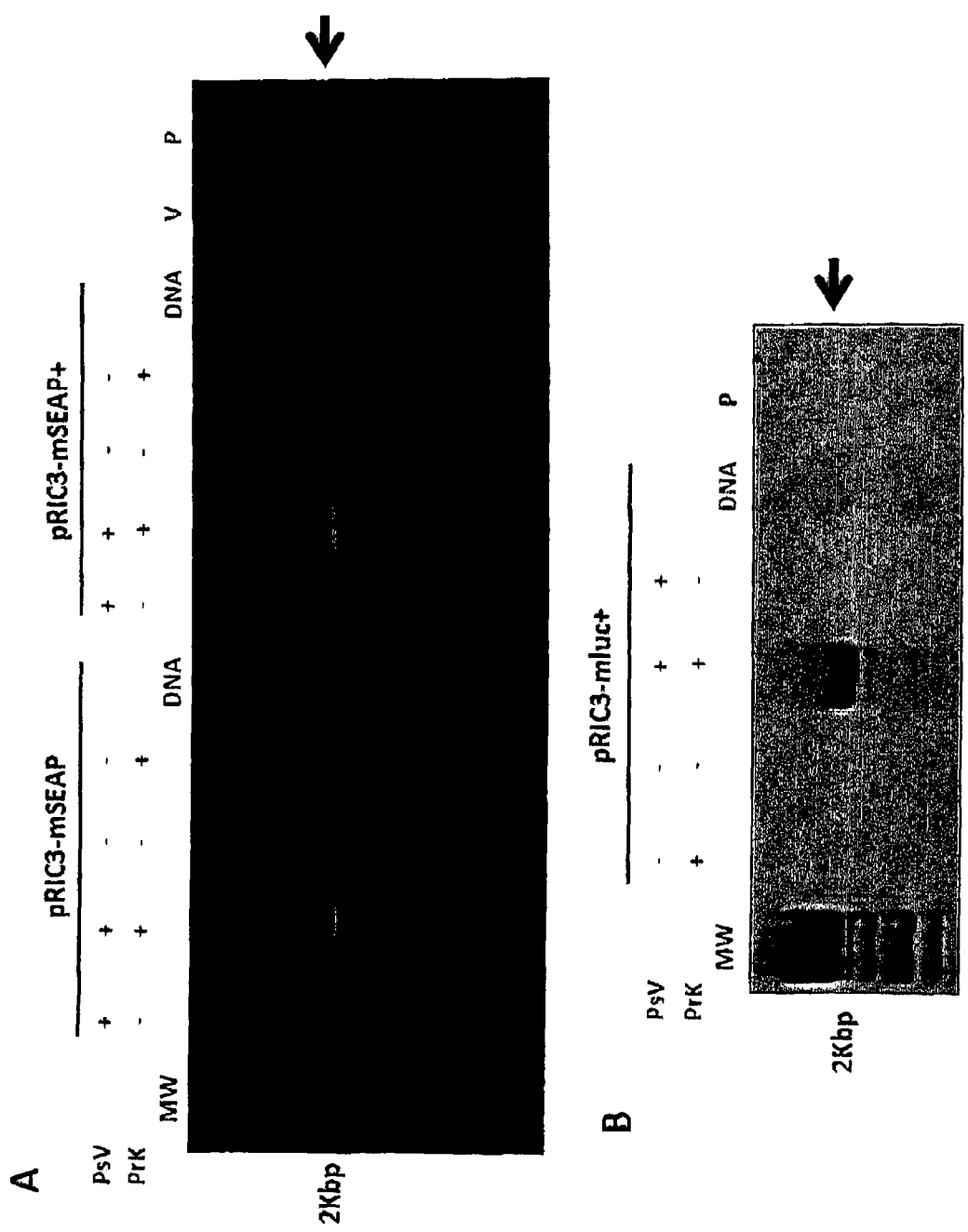
FIG. 14: Presence of DNA in purified PsVs. PCR amplification of (A) pRIC3-mSEAP, pRIC3-mSEAP+, and (B) pRIC3-mluc+ replicon (2.1 Kbp, →) indicates presence of DNA in purified PsV particles after digestion with proteinase K (PrK). MW, molecular weight marker; PrK +/−, PrK digestion; PsV +, pooled L1-containing fractions, PsV −, non-L1 containing fraction (fraction 18); DNA, replicon DNA extract (positive control), V, PrK-digested purified L1/L2 VLPs (negative control); P, plant DNA (negative control).

To confirm that replicon DNA was encapsidated to form PsVs, pooled L1-containing fractions were digested with proteinase K to release the encapsidated pseudogenome, followed by inverse PCR with replicon-specific primers as described above to confirm the presence of replicon DNA (FIG. 14). PCR amplification confirmed that mSEAP, mSEAP+ (FIG. 14A) and mluc+ (FIG. 14B) PsVs contained the expected DNA replicon. No replicon DNA was amplified in samples not treated with proteinase K, indicating that the DNA was encapsidated, and not found outside of the virion shell. Fractions 17 and 18 from each sample were pooled and dialysed. PCR amplification of these fractions, before or after proteinase K digestion, as well as amplification of proteinase K-treated L1/L2 VLPs, yielded no amplification products.

As a preliminary measure of quantity of PsVs in each sample, DNA concentration of proteinase K-treated samples was read using a NanoDrop 1000 spectrophotometer (Thermo Scientific). Table 1 shows NanoDrop readings for all three PsV types. As a broad first estimate at particle concentration for each type, DNA concentration was used to calculate the number of pseudogenomes present per microliter, using the formula:

$$\text{no. of molecules} = \frac{\text{total } DNA \text{ (ng)}}{660. \text{ bp.} \frac{N_A}{10^{-9}}}$$

where ng is nanograms of DNA in 1 µl, bp is pseudogenome size in base pairs, and $N_A$ is Avogadro's constant. Results can be seen in Table 1. Concentration of molecules for all three PsV types was in the billions of particles per milliliter. This data assumes that all DNA present was pseudogenome DNA, and that each PsV packaged exactly one copy of the pseudogenome. Taken together, these results indicate the successful production in planta of PsVs containing a reporter gene for the first time.

TABLE 1

Estimated DNA and particle concentration of purified PsVs

|  | mSEAP | mSEAP+ | mluc+ |
| --- | --- | --- | --- |
| DNA (ng/µl) | 8.56 | 14.33 | 14.95 |
| PsVs (pseudogenomes/(µl) | $1.63 \times 10^9$ | $2.04 \times 10^9$ | $1.84 \times 10^9$ |

Purification of Plant-Produced PsVs

The purification method developed for extracting HPV VLPs of Varsani et al., 2003 (with the modifications described above) proved to be successful, for the purification of PsVs. One concern was the use of liquid $N_2$ for preliminary grinding of plant material. While this step was not, in itself, a problem, cycles of freezing and thawing, as well as freezing plant material for long-term storage at −70° C., resulted in degradation of PsV particles (data not shown). As such, the protocol was modified slightly to replace grinding of frozen leaf material with finely chopping the leaf material in high-salt PBS before proceeding directly to the homogenisation step. This alteration noticeably decreased degradation of PsVs-PCR amplification of the replicon before purification of PsVs showed much more amplification product in fresh plant material when compared to frozen (data not shown).

Electron micrographs dearly demonstrate the successful assembly and isolation of HPV L1/L2 VLPs and PsVs in plants. The PsVs produced demonstrated an unusual variability in size, when compared to other VLP and PsV production methods (Buck at al., 2004; Maclean at al., 2007; Touze and Coursaget, 1998). The broad size range, from 30 nm to 120 nm in diameter, may be due to pooling of fractions corresponding to CsCl density of 1.30-1.33 g/ml. HPV L1/L2 PsVs should be found at a density of 1.32-1.34 g/ml, and as such, some PsVs smaller and larger than the expected 50-60 nm size range may have been pooled, resulting in the variability shown. Other researchers have seen similar results in transgenic plants, and suggest that the smaller-sized particles may be assembly intermediates (Biemelt et al., 2003). It is also possible that the differential sizes seen here are due to an assembly process that differs substantially to that of HPV virions in mammalian cells.

Previous reports on the production of HPV PsVs has used benzonase treatment coupled with PCR to demonstrate that DNA is encapsidated within the virion shell, and not merely associated with the virion (Rossi et al., 2000; Unckell et al., 1997). PsVs produced in this study were not degraded by the 95° C. PCR denaturation step, as demonstrated by no amplification of pseudogenome DNA in PsV samples not digested with proteinase K. As such the protein shell needed to be digested prior to PCR pseudogenome amplification in order to demonstrate the presence of pseudogenome DNA. The significance of this is twofold. Firstly, benzonase treatment was not required to demonstrate encapsidation of DNA, and was subsequently not used. Second, and possibly more importantly, this demonstrates that these PsVs are remarkably stable, even under mildly denaturing conditions. This is an important observation. VLPs are generally relatively unstable, and need to be treated with some care to avoid collapsing the particle (Mach at al., 2006). While PsVs are generally more stable, most that have been produced in other systems are not as stable as these plant-produced PsVs have been demonstrated to be. Accordingly, this suggests an important advantage over traditional PsV production systems.

The data presented here is the first clear evidence for successful production and purification of plant-produced L1/L2 VLPs. While this was not the primary aim of the project, production of L1/L2 VLPs was useful, in that it allowed a comparison of VLPs and PsVs produced in plants. Electron micrographs clearly show regular particles of 40-70 nm in diameter. The low number of VLPs shown relative to the numbers of PsVs is a result of less starting material—VLPs were purified from approximately 25% (by fresh leaf weight) of the crude plant material used for PsV production. Western blots seen in (FIGS. 9C and 9D) clearly show the presence of both L1 and L2 in plants co-infiltrated with pTRAc-L1 and pTRAc-L2. Levels of L2 varied noticeably between different co-infiltration experiments, including co-infiltrations for the production of PsVs. This is not unsurprising, in that the ratio of L1:L2 has been shown to vary between 5:1 and 30:1 in HPV virions and L1/L2 VLPs. This first evidence of L1/L2 VLP production in plants is an encouraging new landmark in plant-based production of HPV VLP vaccines.

A first estimate of final concentration of PsVs yielded figures in the billions per microliter. This estimate is an inherently rough one: several assumptions are made, and the starting data—DNA concentration obtained by spectrophotometry, is far from accurate. These assumptions are 1) that all DNA present was encapsidated pseudogenome DNA, and 2) that each PsV packaged exactly one copy of the pseudogenome. However, it is safe to assume these estimates would not be out by more than two orders of magnitude. Several other researchers have tried to quantitate PsV concentration from various systems, usually using L1 quantitation by ELISA (Fleury at al., 2008), L1 ELISA in combination with PCR (Unckell et al., 1997) or estimating transducing units from reporter assay data (Buck et al., 2004). Future improvements on this system will require an accurate estimate of PsV concentration, such as that provided by ELISA quantitation.

Total yield and concentration factor were not determined. It is clear from electron micrographs and western blots that there was a marked concentration of particles. Western blotting of various stages of purification (FIG. 12) clearly shows an increase in L1 signal, suggesting an approximate doubling in concentration from the crude plant sample to the dialysed PsVs. However, this is by no means a quantitative assay, and as such no firm conclusions can be reached on that basis. Further work to determine PsV concentration is an important next step in evaluating the efficiency of plant production of PsVs.

This study successfully demonstrated the feasibility of producing PsVs in plants. However, much work remains to fully elucidate the production method and efficiency of production for plant-produced PsVs to be a feasible alternative to current methods. Most importantly, quantitation of PsVs produced is a necessary next step. This could be achieved with relative simplicity, by L1 ELISA, as demonstrated by Touze and Coursaget (1998). Another important step is the investigation of all DNA species incorporated into virions, to avoid issues of contamination when using these PsVs. Lastly, an exciting possibility is a simplified purification protocol. The complexity of the current protocol was necessitated by the instability of VLPs. However, the demonstrated stability of these PsVs suggest that a much 'harsher' virus extraction protocol, such as those used for plant virus extraction (E. P. Rybicki, personal communication), could be equally successful in purifying PsVs at a fraction of the time and cost.

Example 4

Neutralisation of Pseudovirion Infection
Pseudovirion Neutralisation Assay

To determine whether plant-produced PsVs were useful for PBNA, mammalian cells were pseudoinfected with plant-produced PsVs. HEK293TT cells were trypsinised and resuspended in neutralisation media (standard growth media, using DMEM lacking in phenol red) at a density of $0.3 \times 10^6$ cells/ml, and plated at 100 μl/well in a 96-well plate. Cells were grown at 37° C. for 3-4 hours. 60 μl of each PsV was added per well, in triplicate, and grown for 72 hours. For the PsVs containing a SEAP replicon, cell culture medium was harvested. For those containing the luciferase replicon, media was removed, the cells were washed once with PBS, and an appropriate volume of Cell Culture Lysis Buffer (Promega, 20 μl for 96-well plates, 400 μl for 6-well plates) was added to the cells. Cells were rocked on an orbital shaker for 15 minutes, and stored at −20° C. overnight.

To measure luciferase production in mammalian cells, the Luciferase Assay System kit (Promega) was used, as per kit instructions. 100 μl luciferase substrate luciferin was added to 20 ul of cell lysate. Luminescence was read on a Modulus Microplate Reader (Turner BioSystems).

Western Blotting was used to confirm SEAP expression after transfection. 32 μl of cell culture media from cells transfected with the SEAP cassette was used for SDS-PAGE, as described above. Blots were probed with a sheep-produced polyclonal anti-calf intestinal alkaline phosphatase (anticiAP) primary antibody (Abcam, ab7330), and mouse anti-sheep alkaline phosphatase-conjugated secondary antibody (Sigma, A8062). SEAP activity was assayed using the Great EscAPe SEAP Chemiluminescence Kit (Clontech Laboratories, Inc.), at 0.6 volumes of those described in kit instructions. Briefly, 50 µl of cell culture media was harvested at 72 hours post-transfection. 15 µl was added to 45 µl dilution buffer, and incubated at 65° C. for 30 minutes. Samples were placed on ice for 5 minutes, before 60 µl of SEAP Substrate Solution was added, and samples were incubated at room temperature for 30-60 minutes. Luminescence was detected on a Modulus Microplate Reader (Turner BioSystems) for 10 seconds. All samples were assayed in triplicate, and standard deviation was calculated for all samples To confirm that plant produced PsVs were able to be used for the PBNA, neutralisation of PsVs was assayed using a known HPV-16 neutralising antibody, following the protocol described by Buck et al. (2005a). HEK293TT cells were prepared as described by Pastrana et al. (2004). 60 µl of PsVs were incubated with 15 µl neutralising antibody HPV-16.V5 (developed by Christensen at al. (1996)) at a dilution of 1 in 4000 (for a final dilution 1 in 20000) on ice for 60 minutes. 75 µl of PsVs were added dropwise to cells in triplicate, and cells were incubated for 72 hours. Luciferase and SEAP activity were assayed as previously described. Standard deviation was calculated for all samples.

Pseudovirion-Based Neutralisation Assay Using Plant-Produced PsVs

Figure 15:
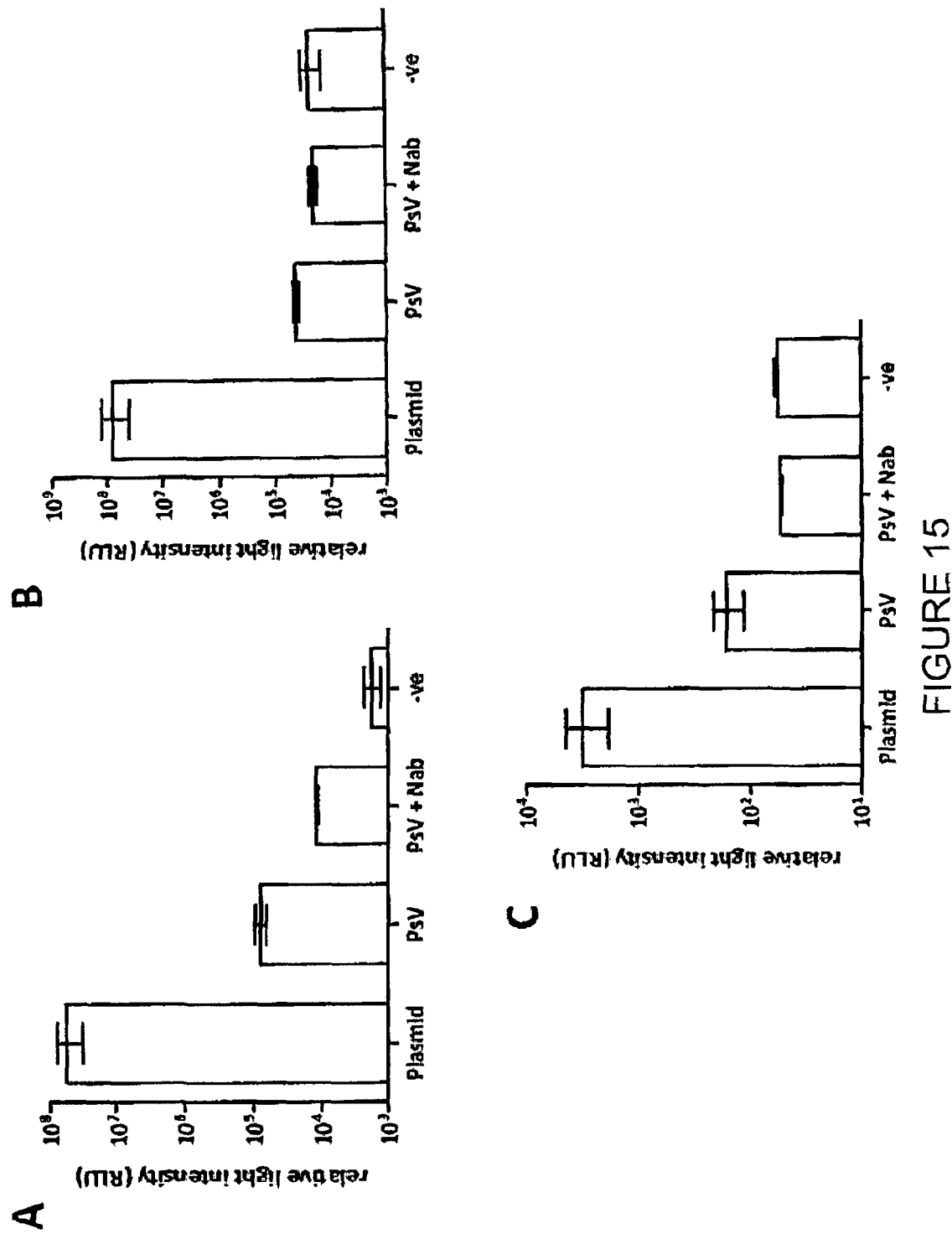
FIG. 15: Reporter gene expression in PsV-pseudoinfected mammalian cells. (A) SEAP expression 72 hours post pRIC3-mSEAP transfection (Plasmid) or mSEAP-PsV pseudoinfection (PsV) in relative light units (RLU), expressed in logarithmic scale (log 10). (B) SEAP expression for pRIC3-mSEAP+, as previously. (C) luc expression for pRIC3-mluc+, as previously. −ve, negative control (media only). All experiments performed in triplicate. Error bars show standard deviation between triplicates.

In order to demonstrate that plant produced HPV-16 PsVs are an effective biological tool for use in the PBNA, PsVs were tested for reporter expression in mammalian cells, as well as for neutralisation with a commonly used HPV-16 neutralising antibody, HPV16.V5. HEK293TT cells were grown in 96 well plates, and pseudoinfected with 60 µl of purified, undiluted PsVs in 0.5M NaCl-PBS, with or without prior incubation with HPV16.V5 monoclonal antibodies diluted 1:20000 in neutralisation media. Successful infection of mammalian cells with PsVs, as well as neutralisation of PsVs, was demonstrated by luc or SEAP reporter gene expression in these cells. FIG. 15 shows reporter gene expression for cells 72 h post-infection with mSEAP (FIG. 15A), mSEAP+ (FIG. 15B) and mluc+ (3.12C) PsVs, with or without the presence of neutralising antibodies (PsV, or PsV+NAb, respectively). The negative control (−ve) for each experiment—mammalian cells with 60 µl of neutralisation media added—provides a baseline reading in RLU, while transfection with the corresponding endotoxin free plasmid DNA is used for the positive control. Pseudoinfection with mSEAP PsVs elicited a clear positive SEAP response (FIG. 15A), although not as strong as that in cells transfected with plasmid DNA by lipofection. Incubation with neutralising antibody partially neutralised infection, as demonstrated by a decrease in SEAP signal. Pseudoinfection with mSEAP+ PsVs did not show a strong SEAP signal above the baseline level provided by the negative control (FIG. 15B). As such, neutralisation of mSEAP+ PsVs was not observed. Pseudoinfection with mluc+ PsVs elicited a weak luciferase signal, although clearly above that of the negative control. Incubation with HPV16.V5 NAb completely neutralised luciferase expression, resulting in expression identical to the negative control.

PsV Testing and PBNA in Mammalian Cells

For plant-produced PsVs to be a useful tool for vaccine testing, it is vital to demonstrate their use in the pseudovirion-based neutralisation assay. PsVs were tested for pseudogenome reporter gene expression and PBNA activity using the Great EscAPe SEAP Chemoluminescence Kit (Clontech Laboratories, Inc.) or the Luciferase Assay System (Sigma). The Great EscAPe kit is used for the widely accepted PBNA protocol developed by the Schiller laboratories, for its sensitivity and ease of use (Buck et al., 2005a). Luciferase has seen broad utility as an easy and sensitive reporter assay, and was chosen due to its low cost Great EscAPe system, as well as to test an alternative pseudogenome size and reporter system.

Of the three PsV types produced, two (mSEAP PsVs and mluc+ PsVs) showed low-level reporter activity after pseudoinfection of mammalian cells, while one (mSEAP+) showed little or no reporter activity. A preliminary neutralisation assay using a well-established mouse monoclonal HPV-16 neutralising antibody HPV16.V5 (Christensen et al., 1996), demonstrated partial neutralisation of mSEAP PsV infection, and complete neutralisation of mluc+ PsV infection. It is unclear why mSEAP+ PsVs failed to induce reporter gene expression in mammalian cells. The SEAP cassette is clearly functional, as demonstrated by successful reporter gene expression by mSEAP PsVs. The plant cassette incorporated into the pseudogenome is unlikely to be the cause—mluc+ PsVs also incorporated an identical plant expression cassette without affecting expression. It is possible that it was due to low concentration of particles in comparison to the other two PsV types—while estimates of concentration based on presence of DNA revealed no major differences, electron micrographs showed less particles in the mSEAP+ PsV samples compared to the other two PsV types. While preliminary, these data provide an initial proof-of-concept for the production of PsVs in planta for use in the PBNA.

Reporter gene expression after pseudoinfection was considerably lower than expected. Most previous PBNA studies have needed to dilute PsVs up to 1000000-fold in order to be within the linear range of the SEAP assay. Preliminary calculations determined PsV particle concentration to be similar to that obtained by Buck et al. (2005a). Accordingly, it would be expected that infectivity would be similar. However, this was not the case: the PsVs tested here showed limited reporter gene expression, even though they were added undiluted to cells. Expression by pseudoinfection was lower than DNA transfected by lipofection. Total DNA added by FuGene transfection to each well of a 96-well plate was approximately 200 ng per well, while total DNA in a 60 µl PsV sample, as determined by NanoDrop spectrophotometry, was 500-900 ng, depending on the sample. Previous work has shown that infectivity of PsVs can be quite low—Roden et al. (1996) estimated an infectivity of 1 in 10000 cells, while Unckell at al. (1997) and Touze and Coursaget (1998) estimated ratios of 1:2000, 1:1000, respectively. However, this does not fully explain the poor expression following pseudoinfection. It is likely that the cause of this discrepancy is the buffer that the PsVs were dialysed into after purification, namely 0.5M NaCl-PBS. Changes in cell culture media osmolality (a measure of the concentration of particles in solution) have a marked effect on mammalian cells. Physiological osmolality is estimated at 290-320 mOsm/kg for mammalian tissues (Waymouth, 1970). Any major deviation from this, such as the introduction of large quantities of NaCl into cell culture media, is likely to seriously affect the growth of the cells, as well as their ability to produce recombinant protein. This is likely to be the case here, and a priority for future work is to repeat these experiments with PsVs in a buffer with less salt. This buffer was chosen because it has been shown to aid in stability of VLPs produced in plants (Varsani et al., 2003). However, these PsVs have demonstrated marked stability to denaturing conditions, and it is likely that they will be stable in PBS.

Example 5

Improvement of Reporter Plasmid and PBNA Using the Improved Plasmid

Introduction of the SV40 Origin of Replication

Figure 19:
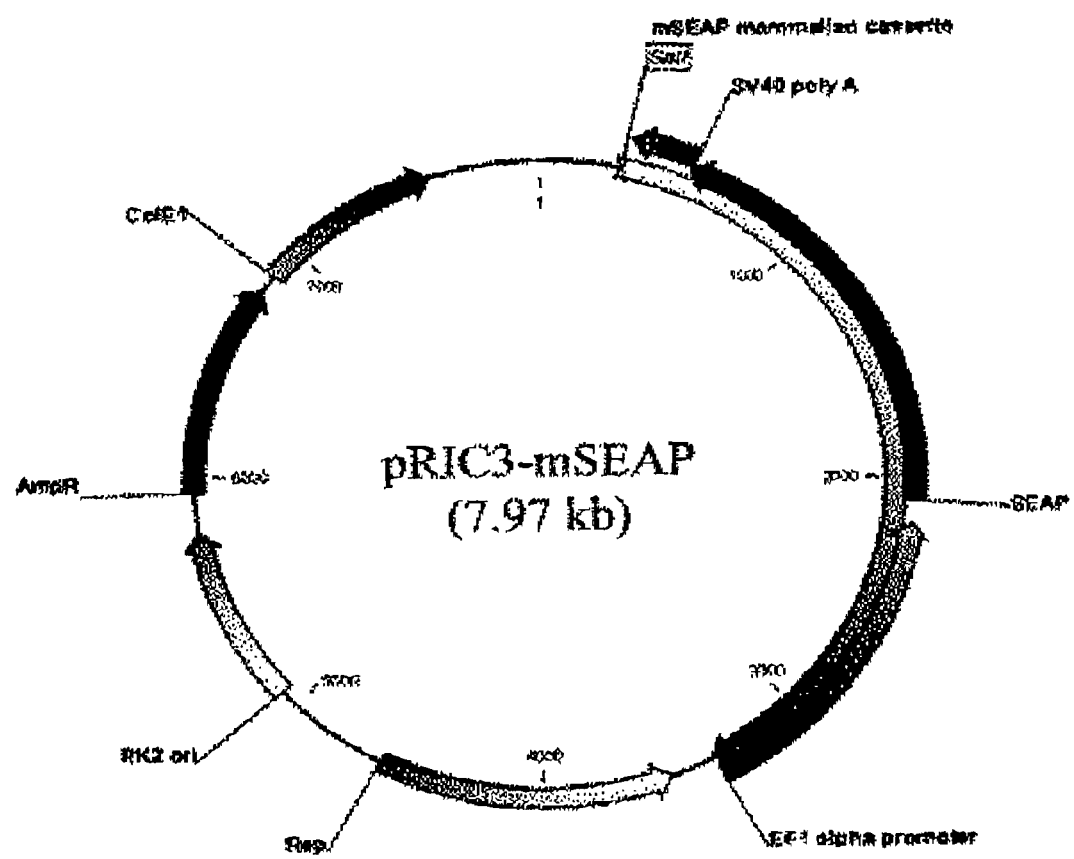
FIG. 19: Cloning strategy for insertion of the SV40 origin of replication (SV40ori) into the pRIC3-mSEAP and pRIC3-mSEAP+ vectors.
Figure 19:
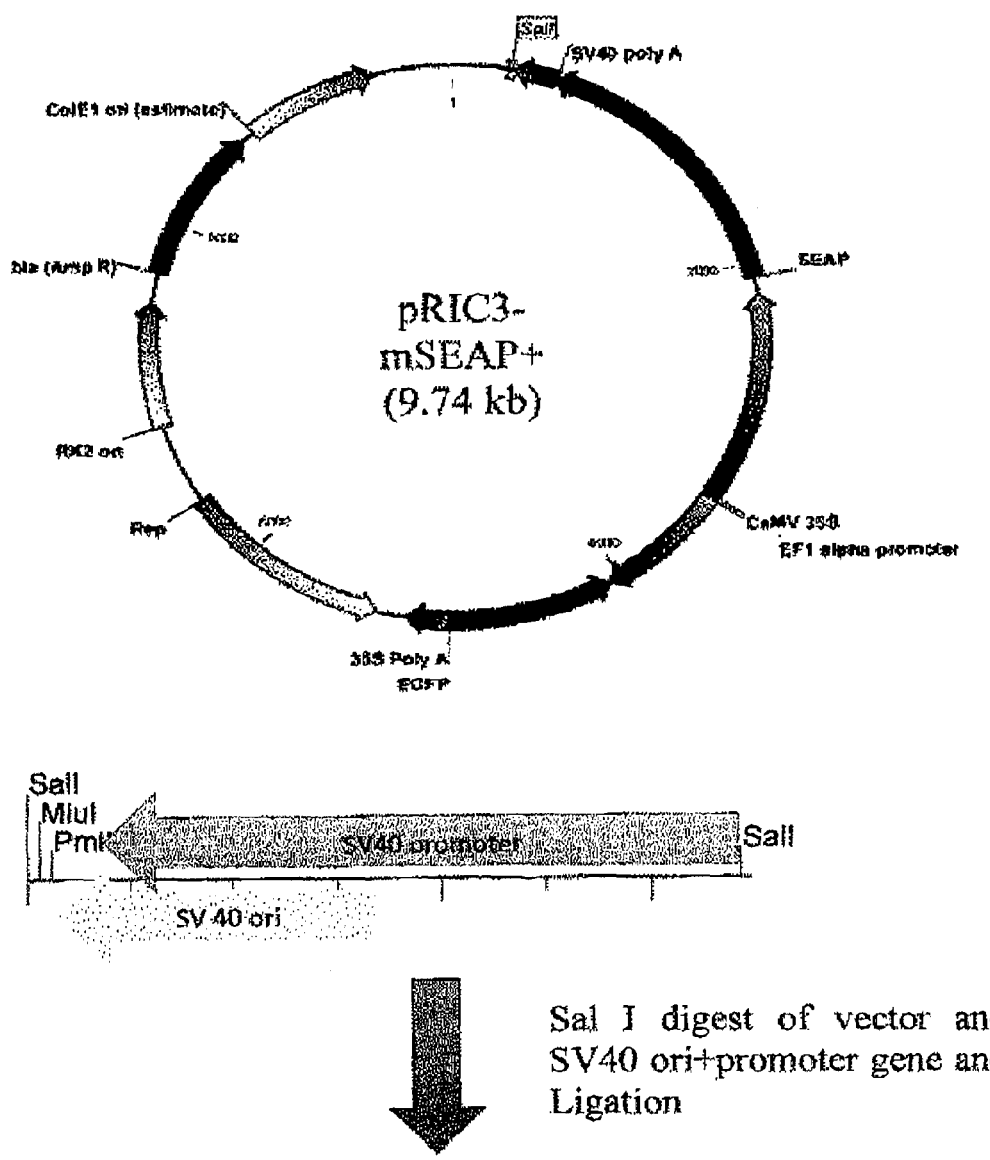
Figure 19:
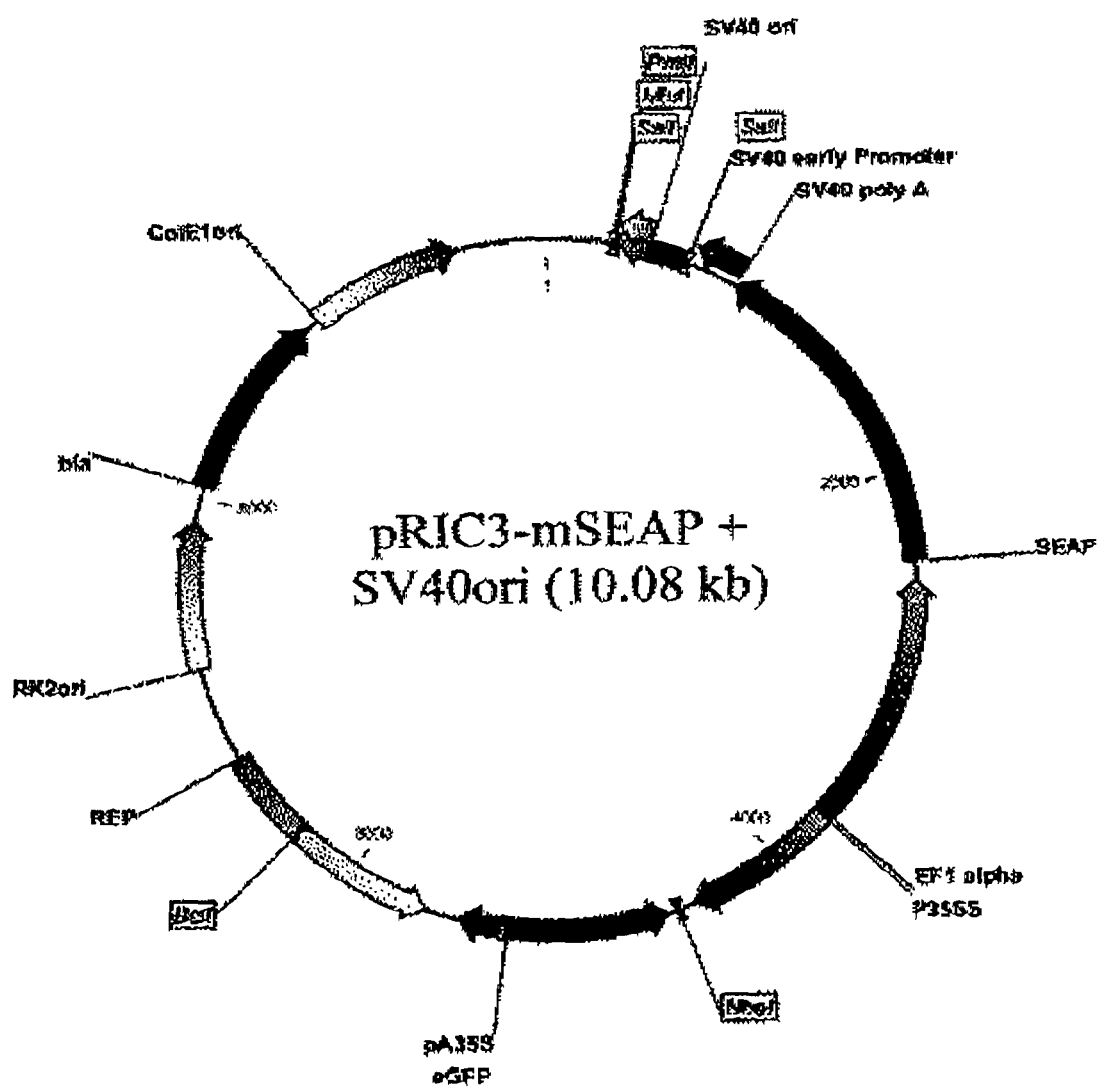
Figure 19:
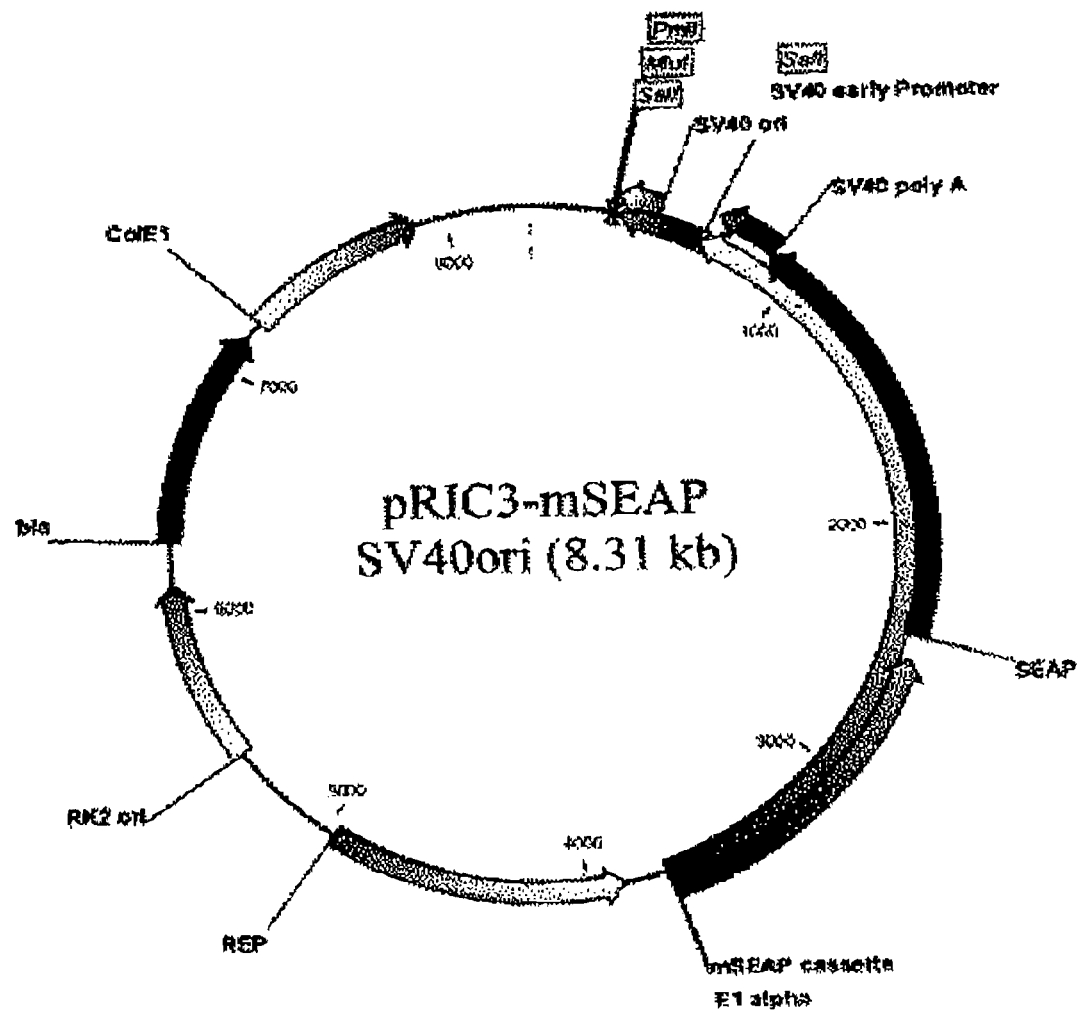

In order to assess whether reporter gene expression could be improved the SV40 origin of replication (SV40ori) was cloned into the pRIC3-mSEAP, pRIC3-mSEAP+ and pRIC3-mluc vectors (FIG. 19). The inventors hypothesized that the inclusion of the SV40ori in the plasmid would increase the amplification of SEAP in HEK293TT cells and would improve reporter protein yields. The vectors that contained the SV40ori (pRIC3-mSEAP-SV40ori (SEQ ID NO:15), pRIC3-mSEAP+-SV40ori (SEQ ID NO:16) and pRIC3-mLuc+-SV40ori (SEQ ID NO:17)) were tested in tissue culture by adding the DNA to HEK293TT cells and comparing expression levels with those obtained with the original DNA vectors.

Figure 20:
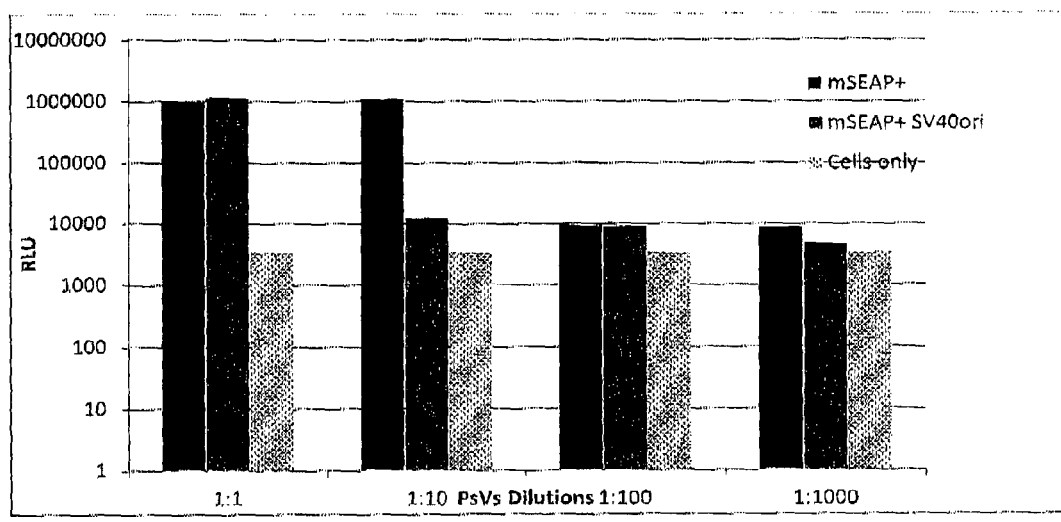
FIG. 20: SEAP expression in mammalian cells infected with mSEAP+ or mSEAP+ SV40ori PsVs. Negative control is non-infected cells. SEAP values are in relative light units (RLU) and pseudovirion dilutions are given on X-axis.

Production of mSEAP-SV40ori PsVs pRIC3-mSEAP-SV40ori, pTRAc-hL1 and pTRAc-hL2 were infiltrated in plants as described above. PSVs which contained a replicating vector encoding a polypeptide for SEAP were produced using both mSEAP+ and mSEAP+-SV40ori constructs. Crude plant extracts were added directly to either continuous (poured the day before) or discontinuous (freshly poured) Optiprep gradients (20%, 33%, 40%, 50%). The gradients were spun for 6 hours at 32,000 rpm. The fractions that produced the darkest blots on a dot blot from the discontinuous gradients for both mSEAP+ and mSEAP+-SV40ori were pooled and used to pseudo-infect HEK293TT cells. PSVs were diluted in DMEM media, $5\times10^5$ cells were added to 6 well-plates, incubated at 37° C. for 3 hours and 400 µl of the PSVs (diluted 1:1, 1:10. 1:100 and 1:1000 in DMEM) were dropped into the cells. The plates were incubated at 37° C. for 3 days. SEAP activity was assessed in the HEK293TT cells by assessing alkaline phosphate activity using dot blots. The inventors were able to detect AP in the supernatant of cells infected with mSEAP+ and mSEAP+-SV40+ori. A SEAP kit was then used to determine the amount of SEAP in supernatant (Table 2, FIG. 20). No significant increase in activity was detected in the mSEAP+-SV40ori PSVs.

TABLE 2

Determination of SEAP levels in relative light units (RLU) per dilution of plant produced PsVs added to HEK293TTcells. Negative control is no DNA and positive control is mSEAP + DNA only.

| mSEAP+ | | mSEAP + -SV40ori | |
| --- | --- | --- | --- |
| Dilution of PsVs | RLU | Dilution of PsVs | RLU |
| 1 | 970,000 | 1 | 1,140,000 |
| 10 | 1,080,000 | 10 | 12,300 |
| 100 | 9,200 | 100 | 9,080 |
| 1000 | 8,500 | 1000 | 4,660 |
| Neg | 3,380 | | |
| DNA 1 µg | 33,900,000 | | |

REFERENCES

Bakker et al., 2006. Proc Natl Acad Sci USA 103, 7577-7582.
Biemelt et al., 2003. Journal of virology 77, 9211-9220.
Bird et al., 2008. Journal of virology 82, 9848-9857.
Bousarghin et al., 2002. Journal of clinical microbiology 40, 926-932.
Brondyk., 2009. Methods in enzymology 463, 131-147.
Buck et al., 2008. Journal of virology 82, 5190-5197.
Buck et al., 2004. Journal of virology 78, 751-757.
Buck et al., 2005a. Methods in molecular medicine 119, 445-462.
Buck et al., 2005b. Journal of virology 79, 2839-2846.
Christensen et al., 1996. Virology 223, 174-184.
Christensen et al., 1990. Journal of virology 64, 5678-5681.
Christensen et al., 1992. The Journal of general virology 73 (Pt 5), 1261-1267.
Chromy et al., 2006. Journal of virology 80, 5086-5091.
Daniell et al., 2009. Trends in plant science 14, 669-679.
Dessy et al., 2008. Human vaccines 4, 425-434.
Durrani et al., 1998. Journal of immunological methods 220, 93-103.
Dvoretzky et al., 1980. Virology 103, 369-375.
Fay et al., 2004. Journal of virology 78, 13447-13454.
Ferlay et al., 2010. International journal of cancer. 127, 2893-2917.
Fleury et al., 2008. Clinical and vaccine immunology: CVI 15, 172-175.
Garcea and Gissmann., 2004. Current opinion in biotechnology 15, 513-517.
Giorgi et al., 2010. Expert. Rev. Vaccines. 9, 913-924.
Gleba et al., 2007. Current opinion in biotechnology 18, 134-141.
Harper et al., 2006. Lancet 367, 1247-1255.
Holmgren et al., 2005. Journal of virology 79, 3938-3948.
Huang et al., 2009. Biotechnology and bioengineering 103, 706-714.
Kapila et al., 1997. Plant Science 122, 101-108.
Kawana et al., 1998. Journal of virology 72, 10298-10300.
Kellogg., 1927. International Critical Tables. Science 65, 273.
Kohl et al., 2006. Clinical and vaccine immunology: CVI 13, 845-853.
Kreider et al., 1987. Journal of virology 61, 590-593.
Kunik et al., 1999. Journal of experimental botany 50, 731-732.
Li et al., 1997. Journal of virology 71, 2988-2995.
Ma et al., 2011. Therapeutic delivery 2, 427-430.
Ma et al., 2005. Trends in plant science 10, 580-585.
Mach et al., 2006. Journal of pharmaceutical sciences 95, 2195-2206.
Maclean et al., 2007. The Journal of general virology 88, 1460-1469.
Matic et al., 2012. Plant biotechnology journal.
Muller et al., 1995. Journal of virology 69, 948-954.
Nuttall et al., 2002. European journal of biochemistry/FEBS 269, 6042-6051.
Ochsenbauer and Kappes., 2009. Current opinion in HIV and AIDS 4, 418-425.
Ogle., 2008. University of Cape Town, Cape Town.
Oh et al., 2004. Virology 328, 266-273.
Okun et al., 2001. Journal of virology 75, 4332-4342.
Pastrana et al., 2004. Virology 321, 205-216.
Peng et al., 2011. Cell & bioscience 1, 26.
Pereira., 2008. University of Cape Town, Cape Town.
Pereira et al., 2009. Arch Virol 154, 187-197.
Regnard et al., 2010. Plant biotechnology journal 8, 38-46.
Robbins et al., 1995. The Journal of infectious diseases 171, 1387-1398.
Roden et al., 1996. Journal of virology 70, 5875-5883.
Rossi et al., 2000. Human gene therapy 11, 1165-1176.
Rybicki., 2010. Plant biotechnology journal 8, 620-637.

Santi et al., 2006. Methods 40, 66-76.
Schillberg et al., 2005. Vaccine 23, 1764-1769.
Shen and Forde 1989. Nucleic acids research 17, 8385.
Shi et al., 2001. Journal of virology 75, 10139-10148.
Smith et al., 1995. The Journal of investigative dermatology 105, 438-444.
Stanley at al., 2008. Vaccine 26 Suppl 10, K62-67.
Stauffer at al., 1998. Journal of molecular biology 283, 529-536.
SuUivan and Pipas, 2001. Virology 287, 1-8.
Tiwari et al., 2009. Biotechnology advances 27, 449-467.
Touze and Coursaget., 1998. Nucleic acids research 26, 1317-1323.
Turpen et al., 1995. Biotechnology (N Y) 13, 53-57.
Unckell et al., 1997. Journal of virology 71, 2934-2939.
Varsani et al., 2003. Journal of virology 77, 8386-8393.
Varsani at al., 2006. Virus research 120, 91-96.
Warzecha et al, 2003. Journal of virology 77, 8702-8711.
Waymouth, 1970. In vitro 6, 109-127.
Yeager et al., 2000. Virology 278, 570-577.
Zhang and Mason. 2006. Biotechnol. Bioeng. 93, 271-279.
Zhou et al., 1993. Virology 194, 210-218.
Zupan et al., 2000. The plant journal: for cell and molecular biology 23, 11-28.

The invention claimed is:

1. A method for producing a human papillomavirus (HPV) pseudovirion in a plant cell, the method comprising the steps of:
   (i) introducing into the plant cell:
   (a) a first nucleic acid encoding a HPV L1 polypeptide,
   (b) a second nucleic acid encoding a HPV L2 polypeptide, wherein the first and second nucleic acids are contained on at least one expression vector, and
   (c) a replicating vector comprising a third nucleic acid encoding a heterologous polypeptide;
   (ii) expressing the HPV L1 polypeptide and the HPV L2 polypeptide in the plant cell, and
   (iii) replicating the replicating vector in the plant cell, in order to produce a high copy number of the replicating vector in the plant cell,
   wherein the expressed HPV L1 and HPV L2 polypeptides assemble, together with a copy of the replicating vector and encapsidate the replicating vector to produce a HPV pseudovirion.

2. The method of claim 1, wherein the first and second nucleic acids are operably linked to regulatory sequences that allow for expression of the HPV L1 and HPV L2 polypeptides.

3. The method of claim 1, wherein replication of the replicating vector is initiated by a regulatory protein.

4. The method of claim 3, wherein the regulatory protein is encoded by a fourth nucleic acid operably linked to a regulatory sequence that allows for the expression of the regulatory protein, wherein the fourth nucleic acid is expressed from at least one from the group consisting of: (i) a nucleic acid sequence contained on the replicating vector; (ii) a nucleic acid sequence contained on the at least one expression vector; (iii) a nucleic acid sequence contained on an independent vector, not being the vector of (i) or (ii) above; and (iv) a nucleic acid sequence integrated into the genomic DNA of the plant cell; wherein expression of the regulatory protein in the presence of the replicating vector results in replication of the replicating vector.

5. The method of claim 1, wherein the third nucleic acid sequence is operably linked to a regulatory sequence that allows for expression of the heterologous polypeptide in a mammalian cell.

6. The method of claim 1, wherein the third nucleic acid encoding the heterologous polypeptide comprises a gene selected from the group consisting of a reporter gene, a therapeutic gene and a gene encoding an antigenic polypeptide.

7. The method of claim 6, wherein the gene encoding a heterologous polypeptide is a reporter gene selected from the group consisting of a luciferase gene and a secreted alkaline phosphatase gene.

8. The method of claim 1, further comprising a step of recovering the HPV pseudovirion from the plant cell.

9. An assay for detecting the presence of a neutralising antibody to HPV in a subject, the assay comprising the steps of:
   (i) combining a HPV pseudovirion produced according to the method of claim 1, with a biological sample from the subject to form a biological sample composition, wherein the heterologous polypeptide is a reporter polypeptide;
   (ii) combining a HPV pseudovirion produced according to the method of claim 1, with a control sample, wherein the control sample does not contain a HPV neutralising antibody, to form a control sample composition, wherein the heterologous polypeptide is a reporter polypeptide;
   (iii) contacting and incubating a mammalian cell capable of being infected with HPV with the biological sample composition of (i) or the control sample composition of (ii); and
   (iv) assaying the expression of the reporter polypeptide;
   wherein decreased expression of the reporter polypeptide in the mammalian cells contacted with the biological sample composition, as compared to mammalian cells contacted with the control sample composition is indicative of the presence of a HPV neutralising antibody in the biological sample.

10. The assay of claim 9 wherein the reporter polypeptide is either a luciferase or a secreted alkaline phosphatase polypeptide.

11. The assay of claim 9 wherein the subject is a human.

12. A HPV pseudovirion comprising a capsid, wherein the capsid comprises a HPV L1 and a HPV L2 polypeptide, wherein the capsid encapsidates a pseudogenome comprising a sequence encoding a heterologous polypeptide, the sequence encoding the heterologous polypeptide being operably linked to a regulatory sequence that allows its expression in a mammalian cell, wherein the pseudogenome is capable of replicating in plant cells, and wherein replication of the pseudogenome is initiated by a plant virus-derived Rep protein expressed from a plant-specific promoter sequence, and wherein the HPV pseudovirion is produced in and recovered from a plant cell.

13. The HPV pseudovirion of claim 12, wherein replication of the pseudogenome can be initiated, in a mammalian cell infected by the HPV pseudovirion, in the presence of a regulatory protein.

14. The HPV pseudovirion of claim 13, wherein the regulatory protein is encoded by a nucleic acid sequence operably linked to a regulatory sequence that allows for the expression of the regulatory protein in the mammalian cell, where in the regulatory protein may be expressed from any one selected from the group consisting of: (i) a nucleic acid sequence contained on the pseudogenome; (ii) a nucleic acid sequence contained on an independent vector; and (iii) a nucleic acid sequence integrated into the genomic DNA of the mammalian cell, wherein expression of the regulatory protein in the mammalian cell results in the replication of the pseudogenome.

15. The HPV pseudovirion of claim 12, wherein the heterologous polypeptide is selected from the group consisting of a reporter polypeptide, a therapeutic polypeptide and an antigenic polypeptide.

16. A pharmaceutical composition comprising a HPV pseudovirion produced by the method of claim 1 and a pharmaceutically acceptable carrier or adjuvant.

17. A pharmaceutical composition comprising the HPV pseudovirion of claim 12 and a pharmaceutically acceptable carrier or adjuvant.

* * * * *